United States Patent
Heintz

(10) Patent No.: US 6,903,077 B1
(45) Date of Patent: Jun. 7, 2005

(54) METHODS AND PRODUCTS FOR DELIVERING NUCLEIC ACIDS

(75) Inventor: Nicholas H. Heintz, Jericho, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 09/477,391

(22) Filed: Jan. 4, 2000

Related U.S. Application Data
(60) Provisional application No. 60/114,745, filed on Jan. 4, 1999, and provisional application No. 60/114,743, filed on Jan. 4, 1999.

(51) Int. Cl.$^7$ .............................................. A61K 48/00
(52) U.S. Cl. ...................... 514/44; 435/320.1; 435/455; 435/325
(58) Field of Search .................... 514/44; 424/93.2, 424/450; 435/320.1, 455, 458; 536/23.1

(56) References Cited

U.S. PATENT DOCUMENTS

| | | | |
|---|---|---|---|
| 5,217,864 A | | 6/1993 | Heintz et al. .................... 435/6 |
| 5,504,192 A | * | 4/1996 | Gill et al. ..................... 530/350 |
| 5,661,025 A | | 8/1997 | Szoka, Jr. et al. |
| 5,721,118 A | * | 2/1998 | Scheffler ..................... 435/69.1 |
| 5,770,222 A | * | 6/1998 | Unger et al. ................. 424/450 |
| 5,830,880 A | | 11/1998 | Sedlacek et al. .............. 514/44 |
| 5,863,737 A | * | 1/1999 | Maki et al. .................... 435/7.1 |
| 5,976,567 A | * | 11/1999 | Wheeler et al. ............. 424/450 |
| 6,130,313 A | * | 10/2000 | Li et al. ....................... 530/324 |

FOREIGN PATENT DOCUMENTS

| | | |
|---|---|---|
| WO | WO 92/03479 | 5/1992 |
| WO | WO 94/23751 | 10/1994 |
| WO | WO 96/13599 | 5/1996 |
| WO | WO 96/36362 | 11/1996 |
| WO | 96-40958 | * 12/1996 |
| WO | 96-40961 | * 12/1996 |
| WO | WO 97/46100 | 12/1997 |
| WO | WO 98/22140 | 5/1998 |

OTHER PUBLICATIONS

Chiu et al., Optimizing energy potentials for success in protein tertiary structure prediction, May 7, 1998, Folding & Design, vol. 3, pp. 223–228.*
Wells et al., The chemokine information source: identification and characterization of novel chemokines using the WorldWideWed and Expessed Sequence Tag Databases, May 1997, Journal of Leukocyte Biology, vol. 61, pp. 545–550.*
Gerhold et al., It's the genes! EST access to human genome content, Oct. 18, 1996, BioEssays, vol. 18, No. 12, pp. 973–981.*
Russell et al., Structual Features can be Unconserved in Proteins with Similar Fold, 1994, J. Mol. Biol., vol. 244, pp. 332–350.*
Dunlap et al., Nanoscopic structure of DNA condensed for gene delivery, 1997, Nucleic Acids Research, vol. 25, No. 15, pp. 3095–3101.*
Barker et al., Delivery of bacterial artificial chromosomes into mammalian cells with psoralen–inactivated adenovirou carrier, 1997, Nucleic Acid Research, vol. 25, No. 10, pp. 1950–1956.*
Marschall et al., Transfer of YACs up to 2.3 Mb intact in human cells with polyethylenimine, 1996, Gene Therapy, vol. 6, pp. 1634–1637.*
Verma et al., Gene therapy–promises, problems and prospects, Sep. 18, 1997, Nature, vol. 389, pp. 239–242.*
Ngo et al., Computational Complexity Protein Structure Prediction, and the Levinthal Paradox, 1994, Birkhauser Boston, vol. 14, pp. 492–495.*
Brahcn, A good antisense molecule is hard to find, Feb. 1998, Elsecier Science Ltd., TIBS, vol. 23, pp. 45–50.*
Anderson, Human gene therapy, Apr. 30, 1998, Nature, vol. 392, pp. 25–30.*
The Sanger Centre, et al. (Genome Research, vol. 8 No. 11, 1998, pp. 1097–1108).
GenBank Accession No. AC 005586, Sep. 2000.
Boulikas, et al., "Histones, Protamine and Polylysine But Not Poly(E:K) Enhance Transfection Efficiency" *Int'l J. Oncol.*, 10:2, pp. 317–322 (1997).
Yang, et al., "Homologous recombination based modification in *Escherichia coli* and germline transmission in transgenic mice of a bacterial artificial chromosome" *Nature Biotechnology,* vol. 15, pp. 859–865 (1997).
Houchens, et al., "The dhrf ori–beta–binding protein RIP60 contains 15 zinc fingers: DNA binding and looping by the central three fingers and an associated proline–rich region" *Nucleic Acid Res.,* 28:2, pp. 570–581 (2000).
Wels, et al., "Biotechnological and gene therapeutic strategies in cancer treatment", *Gene,* 159(1):73–80 (1995) (Abstract).
Cooper, M.J., "Noninfectious gene transfer and expression systems for cancer gene therapy", *Semin. Oncol.,* 23(1):172–87 (1996) (Abstract).
Cristiano, R.J., "Targeted, non–viral gene delivery for cancer gene therapy", *Front Biosci,* 3:D116–70 (1998) (Abstract).
Harris, et al., "Receptor–mediated gene transfer to airway epithelial cells in primary culture", *Am. J. Respir. Cell Mol. Biol.,* 9(4):441–7 (1993) (Abstract).
wolfert, et al., "Chloroquine and amphipathic peptide helices show synergistic transfection in vitro", *Gene Ther.,* 5(3):409–14 (1998) (Abstract).

(Continued)

Primary Examiner—Dave T. Nguyen
(74) Attorney, Agent, or Firm—Wolf, Greenfield & Sacks, P.C.

(57) ABSTRACT

The invention relates to products and methods for delivering nucleic acids of various sizes and preferably greater than 50 kilobases into cells. The nucleic acids are delivered as part of a nucleic acid delivery complex which is composed of at least a nucleic acid binding and condensation domain.

68 Claims, 6 Drawing Sheets

OTHER PUBLICATIONS

Figure 1:
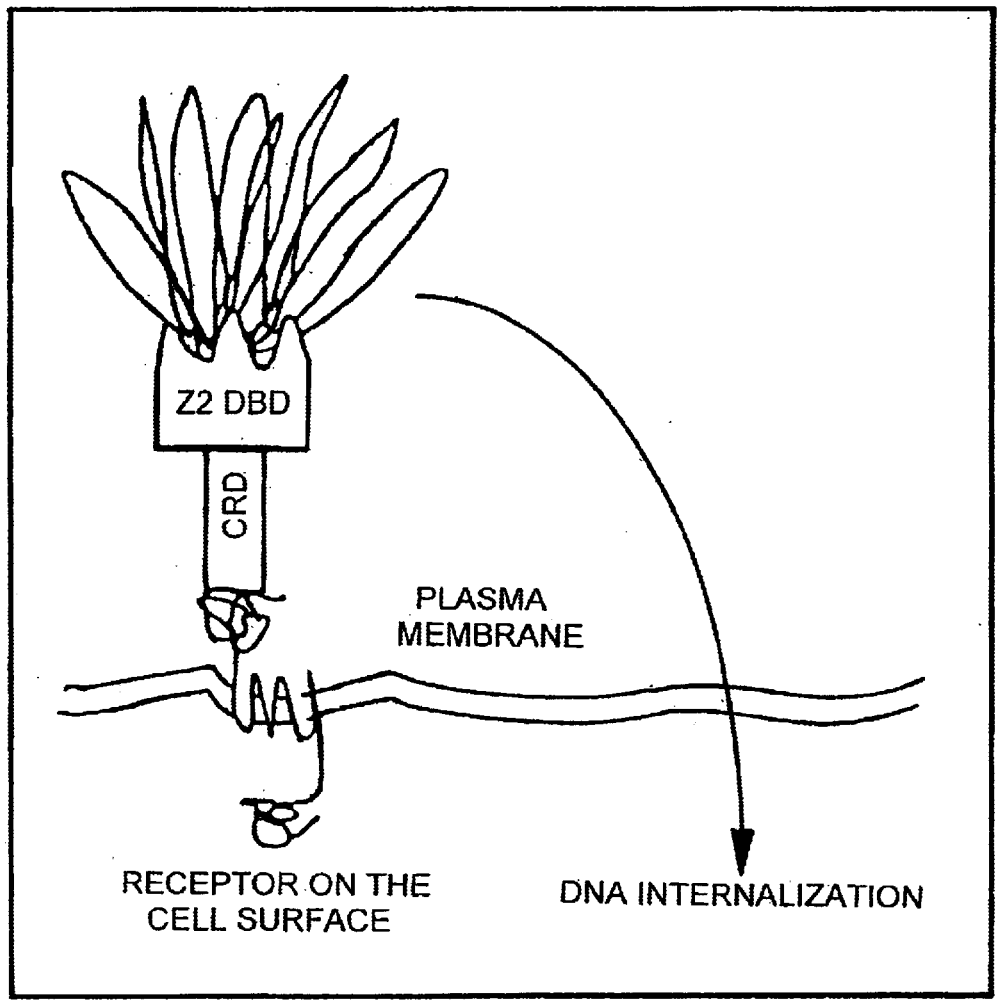

Baker, et al., "Polyethylenimine (PEI) is a simple, inexpensive and effective reagent for condensing and linking plasmid DNA to adenovirus for gene delivery", *Gene Ther.*, 4(8):773–82 (1997) (Abstract).

Perales, et al., "An evaluation of receptor–mediated gene transfer using synthetic DNA–ligand complexes", *Eur. J. Biochem.*, 226(2):255–66 (1994) (Abstract).

Miller, et al, "Targeted vectors for gene therapy", *FASEB J.*, 9(2):190–9 (1995) (Abstract).

Perales, et al., "Gene transfer in vivo: sustained expression and regulation of genes introduced into the liver by receptor–targeted uptake", *Proc. Natl. Acad. Sci. USA*, 91(9):4086–90 (1994) (Abstract).

Schaffer, et al., "Optimization of cell surface binding enhances efficiency and specificity of molecular conjugate gene delivery", *J. Biol. Chem.*, 273(43):28004–8 (1998) (Abstract).

Kim, et al., "Getting a handhold on DNA: Design of poly–zinc finger proteins with femtomolar dissociation constants", *Proc. Natl. Acad. Sci. USA* 95(6):2812–7 (1998) (Abstract).

Liu, et al., "Design of polydactyl zinc–finger proteins for unique addressing within complex genomes", *Proc. Natl. Acad. Sci. USA*, 94(11):5525–30 (1997) (Abstract).

Wu, et al., "Building zinc fingers by selection: toward a therapeutic application", *Proc. Natl. Acad. USA*, 92(2):344–8 (1995) (Abstract).

Schwarzenberger, et al., "Targeted gene transfer for human hematopoietic progenitor cell lines through the c–kit receptor", *Blood*, 87(2):472–8 (1996) (Abstract).

Buschle, et al., "Receptor–mediated gene transfer into human T lymphocytes via binding of DNA/CD3 antibody particles to the CD3 T cell receptor complex", *Hum. Gene Ther.*, 6(6):753–61 (1995) (Abstract).

Fisher, et al., "Biochemical and functional analysis of an adenovirus–based ligand complex for gene transfer", *Biochem. J.*, 299 (Pt. 1):49–58 (1994) (Abstract).

Thurnher, et al., "Carbohydrate receptor–mediated gene transfer to human T leukaemic cells", *Glycobiology*, 4(4):429–35 (1994) (Abstract).

Mahato, et al., "Nonviral vectors for in vivo gene delivery: physicochemical and pharmacokinetic considerations", *Crit. Rev. Ther. Carrier Syst.*, 14(2):133–72 (1997) (Abstract).

Leong, et al., "DNA–polycation nanospheres as non–viral gene delivery vehicles", *J. Controlled Release*, 53(1–3):183–93 (1998) (Abstract).

Carpenter, et al., "Targeting of a cholecystokinin–DNA complex to pancreatic cells in vitro and in vivo", *Gene Ther.*, 5(6):848–54 (1998) (Abstract).

Ding, et al., "Malarial circumsporozoite protein is a novel gene delivery vehicle to primary hepatocyte cultures and cultured cells", *J. Biol. Chem.*, 270(8):3667–76 (1995) (Abstract).

Ferkol, et al., "Gene transfer into the airway epithelium of animals by targeting the polymeric immunoglobulin receptor", *J. Clin. Invest.*, 95(2):493–502 (1995) (Abstract).

Simoes, et al., "Gene delivery by negatively charged ternary complexes of DNA, cationic liposomes and transferrin or fusigenic peptides", *Gene Ther.*, 5(7):955–64 (1998) (Abstract).

Batra, et al., "Receptor–mediated gene delivery employing lectin–binding specificity", *Gene Ther.*, 1(4):255–60 (1994) (Abstract).

Phillips, S.C., "Receptor–mediated DNA delivery approaches to human gene therapy", *Biologicals*, 23(1):13–6 (1995) (Abstract).

Curiel, D.T., "High–efficiency gene transfer employing adenovirus–polylysine–DNA complexes", *Nat. Immun.*, 13(2–3):141–64 (1994) (Abstract).

Morris, et al., "A new peptide vector for efficient delivery of oligonucleotides into mammalian cells", *Nucleic Acids Res.*, 25(14):2730–6 (1997) (Abstract).

Gottschalk, et al., "A novel DNA–peptide complex for efficient gene transfer and expression in mammalian cells", *Gene Ther.*, 3(5):48–57 (1996) (Abstract).

Fominaya, et al., "Target cell–specific DNA transfer mediated by a chimeric multidomain protein. Novel non–viral gene delivery system", *J. Biol. Chem.*, 271(18):10560–8 (1996) (Abstract).

Uherek, et al., "A modular DNA carrier protein based on the structure of diphtheria toxin mediates target cell–specific gene delivery", *J. Biol. Chem.*, 273(15):8835–41 (1998).

Guy, et al., "Delivery of DNA into mammalian cells by receptor–mediated endocytosis and gene therapy", *Mol. Biotechnol.*, 3(3):237–48 (1995) (Abstract).

Takayanagi et al., "Targeting delivery of therapeutic genes using monoclonal antibody; immunogene approach", *Nippon Rinsho*, 56(3):731–6 (1998) (Abstract).

Vidal, et al., "New strategy for RNA vectorization in mammalian cells. Use of a peptide vector", *C.R.Acad. Sci. III*, 320(4):279–87 (1997) (Abstract).

Duguid, et al., "A physicochemical approach for predicting the effectiveness of peptide–based gene delivery systems for use in plasmid–based gene therapy", *Biophys. J.*, 74(6):280214 (1998) (Abstract).

Plank, et al., "The influence of endosome–disruptive peptides on gene transfer using synthetic virus–like gene transfer systems", *J. Biol. Chem.*, 269(17):12918–24 (1994) (Abstract).

Adami, et al., "Stability of peptide–condensed plasmid DNA formulations", *J. Pharm. Sci.*, 87(6):678–83 (1998) (Abstract).

Hart, et al., "Gene delivery and expression mediated by an integrin–binding peptide", *Gene Ther.*, 2(8):552–4 (1995) (Abstract).

Harbottle, et al., "An RGD–oligolysine peptide: a prototype construct for integrin–mediated gene delivery", *Hum. Gene Ther.*, 9(7):1037–47 (1998) (Abstract).

Paul, et al., "Gene transfer using a novel fusion protein, GAL4/invasin", *Hum. Gene Ther.*, 8(10):1253–62 (1997) (Abstract).

Mastrangelo, et al., "RIP60 dimers and multiples of dimers assemble link structures at an origin of bidirectional replication in the dihydrofolate reductase amplicon of Chinese hamster ovary cells", *J. Mol. Biol.*, 232(3):766–78 (1993).

Fominaya, et al., "A chimeric fusion protein containing transforming growth factor–α mediates gene transfer via binding to the EGF receptor", *Gene Ther.*, 5:521–530 (1998).

Wagner, et al., "Coupling of adenovirus to transferrin–polylysine/DNA complexes greatly enhances receptor–mediated gene delivery and expression of transfected genes", *Proc. Natl. Acad Sci. USA*, 89:6099–6103 (1992).

Dunlap, et al., "Nanoscopic structure of DNA condensed for gene delivery", *Nucleic Acids Research* 25(15):3095–3101 (1997).

Cotten, et al., "High–efficiency receptor–mediated delivery of small and large (48 kilobase gene constructs using the endosome–disruption activity of defective of chemically inactivated adenovirus particles", *Proc. Natl. Acad. Sci. USA*, 89:6094–6098 (1992).

Caddle, et al., "RIP60, a Mammalian Origin–Binding Protein, Enhances DNA Bending near the Dihydrofolate Reductase Origin of Replication", *Mol. and Cell. Biol.*, 10(12):6236–6242 (1990).

Edgell, et al., "Efficient Gene Transfer to Human Endothelial Cells using DNA Complexed to Adenovirus Particles", *BioTechniques*, 25:264–272 (1998).

Held, et al., "Protein–Induced Alternations in DNA Structure at the dhfr Origin of Replication", *43. Colloquium Mosbach 1992 DNA Replication and the Cell Cycle* ©Springer–Verlag Berlin Heidelberg (1992).

Houchens, C.R., "Distinct Domains Mediate RIP60 Protein–Protein and Protein–DNA Interactions", A Dissertation Presented to the Faculty of the Graduate College of the University of Vermont, (1988).

Dailey, et al., "Purification of RIP60 and RIP100, Mammalian Proteins with Origin–Specific DNA–Binding and ATP–Dependent DNA Helicase Activities", *Mol. Cell Biol.*, 10(12):6225–6235.

Berg, et al., "Galvanization of Biology: A Growing Appreciation for the Roles of Zinc", *Science*, 271(5252):1081–1085 (1996) (Abstract).

Clarke, et al., "Zinc Fingers in *Caenorhabditis elegans*: Finding Families and Probing Pathways", *Science*, 282(5396):2018–2022 (1998).

Erbacher, et al., "Gene Transfer with Synthetic Virus–Like Particles Via the Integrin–Mediated Endocytosis Pathway", *Gene Therapy*, 6:138–145 (1999).

Kichler, et al., "Influence of the DNA Complexation Medium on the Transfection Efficiency of Lipospermine/DNA Particles", *Gene Therapy*, 5:855–860 (1998).

Crook, et al., "Inclusion of Cholesterol in DOTAP Transfection Complexes Increases the Delivery of DNA to Cells in vitro in the Presence of Serum", *Gene Therapy*, 5:137–143 (1998).

Lambert, et al., "Protein–Mediated DNA Transfer Into Liposomes", *Molecular Microbiology*, 30(4):761–765 (1998).

Wagner, et al., "DNA–Binding Transferrin Conjugates as Functional Gene–Delivery Agents: Synthesis by Linkage of Polylysine or Ethidium Homodimer to the Transferrin Carbohydrate Moiety", *Bioconjugate Chem.*, 2:226–231 (1991).

Nakanishi, et al., "Association with Capsid Proteins Promotes Nuclear Targeting of Simiam Virus 40 DNA", *Proc. Natl. Acad. Sci. USA* 93:96–100 (1996).

Wychowski, et al., "A Domain of SV40 Capsid Polypeptide VP1 That Specifies Migration into the Cell Nucleus", *EMBO J.* Oct.;5(10):2569–76 (1986).

Cotten, et al., "Receptor–Mediated Transport of DNA into Eukaryotic Cells", *Methods Enzymol.*, 217:618–44 (1993).

Rosenfeld, M. A., "Human Artificial Chromosomes Get Real", *Nature Genetics*, 15:333–335 (1997).

Westphal, et al., "A System for Shuttling 200–kb BAC–PAC Clones into Human Cells: Stable Extrachromosomal Persistance and Long–Term Ectopic Gene Activation", *Human Gene Therapy*, 9:1863–1873 (1998).

Böttger, et al., "Condensation of Vector DNA by the Chromosomal Protein HMG1 Results in Efficient Transfection", *Biochimica et Biophysica Acta.*, 950:221–228 (1988).

Barthel, et al., "Laboratory Methods: Gene Transfer Optimization with Lipospermine–Coated DNA", *DNA and Cell Biology*, 12(6):553–560 (1993).

Hansma, et al., "DNA Condensation for Gene Therapy As Monitored by Atomic Force Microscopy", *Nucl. Acids Res.*, 26(10):2481–2487 (1998).

Trubetskoy, et al., "Self–assembly of DNA–Polymer Complexes Using Template Polymerization", *Nucl. Acids Res.*, 26(18):4178–4185 (1998).

Perales, et al., "Biochemical and Functional Characterization of DNA Complexes Capable of Targeting Genes to Hepatocytes via the Asialoglycoprotein Receptor", *J. of Biol. Chem.*, 272(11):7398–7407 (Issue of Mar. 14) (1997).

Boukhnikachvili, et al, "Structure of In–serum Transfecting DNA–Cationic Lipid Complexes", *FEBS Letters*, 409:188–194 (1997).

Wagner, et al., "Transferrin–Polycation–DNA Complexes: The Effect of Polycations on the Structure of the Complex and DNA Delivery Cells", *Proc. Natl. Acad. Sci. USA* 88:4255–4259 (1991).

Mahato, et al., "Pharmaceutical Perspectives of Nonviral Gene Therapy", *Advances In Genetics*, 41:95–157 (1999).

* cited by examiner

SEQUENCE LISTING

<160> NUMBER OF SEQ ID NOS: 68

<210> SEQ ID NO 1
<211> LENGTH: 2954
<212> TYPE: DNA
<213> ORGANISM: Homo Sapiens
<220> FEATURE:
<221> NAME/KEY: CDS
<222> LOCATION: (130)...(1831)

<400> SEQUENCE: 1
cgctgtttgt ccagcttctc agagttgctg tgcagctcgg atgtggcata ggaaacagca    60

-continued

```
gacacaggga gagggcagca taaggcactg tagggagcag tggccacatt ttctgcagag      120 gaagaaccg atg ctg gaa cgt cgt tgc agg ggc ccc ctg gcc atg ggc ctg      171
          Met Leu Glu Arg Arg Cys Arg Gly Pro Leu Ala Met Gly Leu
            1               5                  10 gcc cag ccc cga ctc ctt tct ggg ccc tcc cag gag tca ccc cag acc        219
Ala Gln Pro Arg Leu Leu Ser Gly Pro Ser Gln Glu Ser Pro Gln Thr
 15                  20                  25                  30 ctg ggg aag gag tcc cgc ggg ctg agg caa caa ggc acg tca gtg gcc        267
Leu Gly Lys Glu Ser Arg Gly Leu Arg Gln Gln Gly Thr Ser Val Ala
                 35                  40                  45 cag tct ggt gcc caa gcc cca ggc agg gcc cat cgc tgt gcc cac tgt        315
Gln Ser Gly Ala Gln Ala Pro Gly Arg Ala His Arg Cys Ala His Cys
 50                  55                  60 cga agg cac ttc cct ggc tgg gtg gct ctg tgg ctt cac acc cgc cgg        363
Arg Arg His Phe Pro Gly Trp Val Ala Leu Trp Leu His Thr Arg Arg
             65                  70                  75 tgc cag gcc cgg ctg ccc ttg ccc tgc cct gag tgt ggc cgt cgc ttt        411
Cys Gln Ala Arg Leu Pro Leu Pro Cys Pro Glu Cys Gly Arg Arg Phe
 80                  85                  90 cgc cat gcc ccc ttc tta gca ctg cac cgc cag gtc cat gct gct gcc        459
Arg His Ala Pro Phe Leu Ala Leu His Arg Gln Val His Ala Ala Ala
 95                 100                 105                 110 acc cca gac ctg ggc ttt gcc tgc cac ctc tgt ggg cag agc ttc cga        507
Thr Pro Asp Leu Gly Phe Ala Cys His Leu Cys Gly Gln Ser Phe Arg
                115                 120                 125 ggc tgg gtg gcc ctg gtt ctg cat ctg ctg gcc cat tca gct gca aag        555
Gly Trp Val Ala Leu Val Leu His Leu Leu Ala His Ser Ala Ala Lys
            130                 135                 140 caa ccc atc gct tgt ccc aaa tgc gag aga cgc ttc tgg cga cga aag        603
Gln Pro Ile Ala Cys Pro Lys Cys Glu Arg Arg Phe Trp Arg Arg Lys
                145                 150                 155 cag ctt cga gct cat ctg cgg cgg tgc cac cct ccc gcc ccg gag gcc        651
Gln Leu Arg Ala His Leu Arg Arg Cys His Pro Pro Ala Pro Glu Ala
160                 165                 170 cgg ccc ttc ata tgc ggc aac tgt ggc cgg agc ttt gcc cag tgg gac        699
Arg Pro Phe Ile Cys Gly Asn Cys Gly Arg Ser Phe Ala Gln Trp Asp
175                 180                 185                 190 cag cta gtt gcc cac aag cgg gtg cac gta gct gag gcc ctg gag gag        747
Gln Leu Val Ala His Lys Arg Val His Val Ala Glu Ala Leu Glu Glu
                195                 200                 205 gcc gca gcc aag gct ctg ggg ccc cgg ccc agg ggc cgc ccc gcg gtg        795
Ala Ala Ala Lys Ala Leu Gly Pro Arg Pro Arg Gly Arg Pro Ala Val
            210                 215                 220 acc gcc ccc cgg ccc ggt gga gat gcc gtc gac cgc ccc ttc cag tgt        843
Thr Ala Pro Arg Pro Gly Gly Asp Ala Val Asp Arg Pro Phe Gln Cys
                225                 230                 235 gcc tgt tgt ggc aag cgc ttc cgg cac aag ccc aac ttg atc gct cac        891
Ala Cys Cys Gly Lys Arg Phe Arg His Lys Pro Asn Leu Ile Ala His
240                 245                 250 cgc cgc gtg cac acg ggc gag cgg ccc cac cag tgc ccc gag tgc ggg        939
Arg Arg Val His Thr Gly Glu Arg Pro His Gln Cys Pro Glu Cys Gly
255                 260                 265                 270 aag cgc ttt acc aat aag ccc tat ctg act tcg cac cgg cgc atc cac        987
Lys Arg Phe Thr Asn Lys Pro Tyr Leu Thr Ser His Arg Arg Ile His
                275                 280                 285 acc ggc gag aag ccc tac ccg tgc aaa gag tgc ggc cgc cgc ttc cgg       1035
Thr Gly Glu Lys Pro Tyr Pro Cys Lys Glu Cys Gly Arg Arg Phe Arg
            290                 295                 300 cac aaa ccc aac ctg ctg tct cac agc aag att cac aag cga tcc gag       1083
```

```
                His Lys Pro Asn Leu Leu Ser His Ser Lys Ile His Lys Arg Ser Glu
                    305                 310                 315 ggg tcg gcc cag gcc gcc ccc ggc ccg ggg agc ccc cag ctg cca gcc     1131
Gly Ser Ala Gln Ala Ala Pro Gly Pro Gly Ser Pro Gln Leu Pro Ala
320                 325                 330 ggc ccc cag gag tcc gcg gcc gag ccc acc ccg gcg gta cct ctg aaa     1179
Gly Pro Gln Glu Ser Ala Ala Glu Pro Thr Pro Ala Val Pro Leu Lys
335                 340                 345                 350 ccg gcc cag gag ccg ccg cca ggg gcc ccg cca gag cac ccg cag gac     1227
Pro Ala Gln Glu Pro Pro Pro Gly Ala Pro Pro Glu His Pro Gln Asp
                355                 360                 365 ccg atc gaa gcc ccc ccc tcc ctc tac agc tgc gac gac tgc ggc agg     1275
Pro Ile Glu Ala Pro Pro Ser Leu Tyr Ser Cys Asp Asp Cys Gly Arg
            370                 375                 380 agc ttc cgg ctg gag cgc ttc ctg cgg gcc cac cag cgg cac gac acc     1323
Ser Phe Arg Leu Glu Arg Phe Leu Arg Ala His Gln Arg His Asp Thr
        385                 390                 395 ggg gag cgg ccc ttc acc tgc gcc gag tgc ggg aag aac ttc ggc aag     1371
Gly Glu Arg Pro Phe Thr Cys Ala Glu Cys Gly Lys Asn Phe Gly Lys
    400                 405                 410 aag acg cac ctg gtg gcg cac tcg ccg gtg cac tcc ggc gag cgg ccc     1419
Lys Thr His Leu Val Ala His Ser Pro Val His Ser Gly Glu Arg Pro
415                 420                 425                 430 ttc gcc tgc gag gag tgc ggc cgc cgc ttc tcc cag ggc agc cat ctg     1467
Phe Ala Cys Glu Glu Cys Gly Arg Arg Phe Ser Gln Gly Ser His Leu
                435                 440                 445 gcg gcg cat cgg ccg gac cac gcc ccc gat cgg ccc ttc gtg tgt ccc     1515
Ala Ala His Arg Pro Asp His Ala Pro Asp Arg Pro Phe Val Cys Pro
            450                 455                 460 gac tgc ggc aag gcc ttc cgc cac aaa ccc tac ctg gcg cgg cac cgg     1563
Asp Cys Gly Lys Ala Phe Arg His Lys Pro Tyr Leu Ala Arg His Arg
        465                 470                 475 cgc atc cac acc ggc gag aag ccc tac gtc tgc ccc gac tgc ggc aaa     1611
Arg Ile His Thr Gly Glu Lys Pro Tyr Val Cys Pro Asp Cys Gly Lys
    480                 485                 490 gcc ttc agc cag aag tcc aac ctg gtg tcg cac cgg cgc atc cac acg     1659
Ala Phe Ser Gln Lys Ser Asn Leu Val Ser His Arg Arg Ile His Thr
495                 500                 505                 510 ggc gag cgg ccc tac gcc tgt ccc gac tgc gac cgc agc ttc agc cag     1707
Gly Glu Arg Pro Tyr Ala Cys Pro Asp Cys Asp Arg Ser Phe Ser Gln
                515                 520                 525 aag tcc aac ctc atc acc cac cgc aag agc cac atc cgg gac ggc gcc     1755
Lys Ser Asn Leu Ile Thr His Arg Lys Ser His Ile Arg Asp Gly Ala
            530                 535                 540 ttc tgc tgt gcc atc tgt ggc cag acc ttc gac gac gag gag aga ctc     1803
Phe Cys Cys Ala Ile Cys Gly Gln Thr Phe Asp Asp Glu Glu Arg Leu
        545                 550                 555 ctg gcc cac cag aag aag cac gat gtc t gagacggtgg gcggggccgt         1851
Leu Ala His Gln Lys Lys His Asp Val
        560                 565 gttggctgag agagggctgg ggtccttcgt ggtgggagtc gcagtgggct ggggggtgcct  1911 gcctagtgct ggagtagggg acaatgggaa tcctagaggg gatggaagat gcggggagtg   1971
agctgggtgg gccctgctag cgagagaggt caacccggt ggccagggaa cccacttcca    2031
agcgcaggga cgccggcctc cagctggtgt gtgctaaggc tccgtcctga ctgccctgtg   2091
ccctggaaaa gcagcaatac atccgcccct tacagccctc tggctagagg agccaccagt   2151
ggaaaggaag ccctccatcc tctggtatta acgccttaat gccctgtct tttactgtaa    2211
```

-continued

```
gttacttaga tcattttggg aagcaggcgt ggtagagtcc tgtaaatgaa tgctctgggc     2271
tagatacagc ttggagaacc tgctggcctt gttagacaga acttgggcct ttgccagcag     2331
caagaggtga agcgaagcca ctcttacctc tcccttcccc tcccacctgc ccctgcgta     2391 ggcacccaga cttggagaga cccgtctgct gttaatactt ccatcctctt ccttcccaaa     2451
gagcagatcc caaggcattt actccttggt ctgtctcgct ttatctgtcg ccctcccag     2511 cgctgagagc ctcccctggc tgtcagcagc actgtgtcca ggctcttgtc tgaacaccgc     2571 agccctcct tcgctccttc cacagctcag catgtcacgg caaggactgc cgcattggtg      2631
atggagggcc agctgagggg aagttgctgg tgagtttcct ttctccattt ctagcatatg     2691
acacctggcc tctgcttgag cacttaggtg acaggaactt ccgcacctcc tgaggccctg     2751
gatgattcta attgttagaa attctaattg ttagaaatcc ttccttataa tgaatgaatt     2811
ctgctttcct ataatttcta cctattgggc cttgttctgt tctctggaac taaacagaac     2871
aaccatttac ccctcctttt caaactagag aataaacatt tggttttaga aaaaaaaaa     2931 aaaaaaaaaa aaaaaaaaaa aaa                                              2954
```

<210> SEQ ID NO 2
<211> LENGTH: 567
<212> TYPE: PRT
<213> ORGANISM: Homo Sapiens

<400> SEQUENCE: 2

```
Met Leu Glu Arg Arg Cys Arg Gly Pro Leu Ala Met Gly Leu Ala Gln
 1               5                  10                  15

Pro Arg Leu Leu Ser Gly Pro Ser Gln Glu Ser Pro Gln Thr Leu Gly
            20                  25                  30

Lys Glu Ser Arg Gly Leu Arg Gln Gln Gly Thr Ser Val Ala Gln Ser
        35                  40                  45

Gly Ala Gln Ala Pro Gly Arg Ala His Arg Cys Ala His Cys Arg Arg
    50                  55                  60

His Phe Pro Gly Trp Val Ala Leu Trp Leu His Thr Arg Arg Cys Gln
65                  70                  75                  80

Ala Arg Leu Pro Leu Pro Cys Pro Glu Cys Gly Arg Arg Phe Arg His
                85                  90                  95

Ala Pro Phe Leu Ala Leu His Arg Gln Val His Ala Ala Thr Pro
            100                 105                 110

Asp Leu Gly Phe Ala Cys His Leu Cys Gly Gln Ser Phe Arg Gly Trp
        115                 120                 125

Val Ala Leu Val Leu His Leu Leu Ala His Ser Ala Ala Lys Gln Pro
    130                 135                 140

Ile Ala Cys Pro Lys Cys Glu Arg Arg Phe Trp Arg Arg Lys Gln Leu
145                 150                 155                 160

Arg Ala His Leu Arg Arg Cys His Pro Ala Pro Glu Ala Arg Pro
                165                 170                 175

Phe Ile Cys Gly Asn Cys Gly Arg Ser Phe Ala Gln Trp Asp Gln Leu
            180                 185                 190

Val Ala His Lys Arg Val His Val Ala Glu Ala Leu Glu Glu Ala Ala
        195                 200                 205

Ala Lys Ala Leu Gly Pro Arg Pro Arg Gly Arg Pro Ala Val Thr Ala
    210                 215                 220

Pro Arg Pro Gly Gly Asp Ala Val Asp Arg Pro Phe Gln Cys Ala Cys
225                 230                 235                 240
```

```
Cys Gly Lys Arg Phe Arg His Lys Pro Asn Leu Ile Ala His Arg Arg
                245                 250                 255

Val His Thr Gly Glu Arg Pro His Gln Cys Pro Glu Cys Gly Lys Arg
                260                 265                 270

Phe Thr Asn Lys Pro Tyr Leu Thr Ser His Arg Ile His Thr Gly
                275                 280                 285

Glu Lys Pro Tyr Pro Cys Lys Glu Cys Gly Arg Arg Phe Arg His Lys
                290                 295                 300

Pro Asn Leu Leu Ser His Ser Lys Ile His Lys Arg Ser Glu Gly Ser
305                 310                 315                 320

Ala Gln Ala Ala Pro Gly Pro Ser Pro Gln Leu Pro Ala Gly Pro
                325                 330                 335

Gln Glu Ser Ala Ala Glu Pro Thr Pro Ala Val Pro Leu Lys Pro Ala
                340                 345                 350

Gln Glu Pro Pro Pro Gly Ala Pro Pro Glu His Pro Gln Asp Pro Ile
                355                 360                 365

Glu Ala Pro Pro Ser Leu Tyr Ser Cys Asp Asp Cys Gly Arg Ser Phe
370                 375                 380

Arg Leu Glu Arg Phe Leu Arg Ala His Gln Arg His Asp Thr Gly Glu
385                 390                 395                 400

Arg Pro Phe Thr Cys Ala Glu Cys Gly Lys Asn Phe Gly Lys Thr
                405                 410                 415

His Leu Val Ala His Ser Pro Val His Ser Gly Glu Arg Pro Phe Ala
                420                 425                 430

Cys Glu Glu Cys Gly Arg Arg Phe Ser Gln Gly Ser His Leu Ala Ala
                435                 440                 445

His Arg Pro Asp His Ala Pro Asp Arg Pro Phe Val Cys Pro Asp Cys
                450                 455                 460

Gly Lys Ala Phe Arg His Lys Pro Tyr Leu Ala Arg His Arg Arg Ile
465                 470                 475                 480

His Thr Gly Glu Lys Pro Tyr Val Cys Pro Asp Cys Gly Lys Ala Phe
                485                 490                 495

Ser Gln Lys Ser Asn Leu Val Ser His Arg Ile His Thr Gly Glu
                500                 505                 510

Arg Pro Tyr Ala Cys Pro Asp Cys Asp Arg Ser Phe Ser Gln Lys Ser
                515                 520                 525

Asn Leu Ile Thr His Arg Lys Ser His Ile Arg Asp Gly Ala Phe Cys
                530                 535                 540

Cys Ala Ile Cys Gly Gln Thr Phe Asp Asp Glu Arg Leu Leu Ala
545                 550                 555                 560

His Gln Lys Lys His Asp Val
                565
```

<210> SEQ ID NO 3
<211> LENGTH: 378
<212> TYPE: DNA
<213> ORGANISM: Homo Sapiens
<220> FEATURE:
<221> NAME/KEY: CDS
<222> LOCATION: (1)...(378)

<400> SEQUENCE: 3

```
ggt gga gat gcc gtc gac cgc ccc ttc cag tgt gcc tgt tgt ggc aag    48
Gly Gly Asp Ala Val Asp Arg Pro Phe Gln Cys Ala Cys Cys Gly Lys
 1               5                  10                  15 cgc ttc cgg cac aag ccc aac ttg atc gct cac cgc cgc gtg cac acg    96
```

```
Arg Phe Arg His Lys Pro Asn Leu Ile Ala His Arg Arg Val His Thr
        20                  25                  30 ggc gag cgg ccc cac cag tgc ccc gag tgc ggg aag cgc ttt acc aat    144
Gly Glu Arg Pro His Gln Cys Pro Glu Cys Gly Lys Arg Phe Thr Asn
        35                  40                  45 aag ccc tat ctg act tcg cac cgg cgc atc cac acc ggc gag aag ccc    192
Lys Pro Tyr Leu Thr Ser His Arg Arg Ile His Thr Gly Glu Lys Pro
 50                  55                  60 tac ccg tgc aaa gag tgc ggc cgc cgc ttc cgg cac aaa ccc aac ctg    240
Tyr Pro Cys Lys Glu Cys Gly Arg Arg Phe Arg His Lys Pro Asn Leu
65                  70                  75                  80 ctg tct cac agc aag att cac aag cga tcc gag ggg tcg gcc cag gcc    288
Leu Ser His Ser Lys Ile His Lys Arg Ser Glu Gly Ser Ala Gln Ala
            85                  90                  95 gcc ccc ggc ccg ggg agc ccc cag ctg cca gcc ggc ccc cag gag tcc    336
Ala Pro Gly Pro Gly Ser Pro Gln Leu Pro Ala Gly Pro Gln Glu Ser
                100                 105                 110 gcg gcc gag ccc acc ccg gcg gta cct ctg aaa ccg gcc cag                378
Ala Ala Glu Pro Thr Pro Ala Val Pro Leu Lys Pro Ala Gln
            115                 120                 125
```

<210> SEQ ID NO 4
<211> LENGTH: 126
<212> TYPE: PRT
<213> ORGANISM: Homo Sapiens

<400> SEQUENCE: 4

```
Gly Gly Asp Ala Val Asp Arg Pro Phe Gln Cys Ala Cys Cys Gly Lys
1               5                   10                  15

Arg Phe Arg His Lys Pro Asn Leu Ile Ala His Arg Arg Val His Thr
        20                  25                  30

Gly Glu Arg Pro His Gln Cys Pro Glu Cys Gly Lys Arg Phe Thr Asn
        35                  40                  45

Lys Pro Tyr Leu Thr Ser His Arg Arg Ile His Thr Gly Glu Lys Pro
 50                  55                  60

Tyr Pro Cys Lys Glu Cys Gly Arg Arg Phe Arg His Lys Pro Asn Leu
65                  70                  75                  80

Leu Ser His Ser Lys Ile His Lys Arg Ser Glu Gly Ser Ala Gln Ala
            85                  90                  95

Ala Pro Gly Pro Gly Ser Pro Gln Leu Pro Ala Gly Pro Gln Glu Ser
                100                 105                 110

Ala Ala Glu Pro Thr Pro Ala Val Pro Leu Lys Pro Ala Gln
            115                 120                 125
```

<210> SEQ ID NO 5
<211> LENGTH: 177
<212> TYPE: DNA
<213> ORGANISM: Homo Sapiens
<220> FEATURE:
<221> NAME/KEY: CDS
<222> LOCATION: (1)...(177)

<400> SEQUENCE: 5

```
cga tcc gag ggg tcg gcc cag gcc gcc ccc ggc ccg ggg agc ccc cag     48
Arg Ser Glu Gly Ser Ala Gln Ala Ala Pro Gly Pro Gly Ser Pro Gln
1               5                   10                  15 ctg cca gcc ggc ccc cag gag tcc gcg gcc gag ccc acc ccg gcg gta     96
Leu Pro Ala Gly Pro Gln Glu Ser Ala Ala Glu Pro Thr Pro Ala Val
        20                  25                  30 cct ctg aaa ccg gcc cag gag ccg ccg cca ggg gcc ccg cca gag cac    144
Pro Leu Lys Pro Ala Gln Glu Pro Pro Pro Gly Ala Pro Pro Glu His
```

```
Pro Leu Lys Pro Ala Gln Glu Pro Pro Gly Ala Pro Pro Glu His
        35                  40                  45 ccg cag gac ccg atc gaa gcc ccc ccc tcc ctc                     177
Pro Gln Asp Pro Ile Glu Ala Pro Pro Ser Leu
        50                  55

<210> SEQ ID NO 6
<211> LENGTH: 59
<212> TYPE: PRT
<213> ORGANISM: Homo Sapiens

<400> SEQUENCE: 6

Arg Ser Glu Gly Ser Ala Gln Ala Ala Pro Gly Gly Ser Pro Gln
 1               5                  10                  15

Leu Pro Ala Gly Pro Gln Glu Ser Ala Ala Glu Pro Thr Pro Ala Val
        20                  25                  30

Pro Leu Lys Pro Ala Gln Glu Pro Pro Gly Ala Pro Pro Glu His
        35                  40                  45

Pro Gln Asp Pro Ile Glu Ala Pro Pro Ser Leu
        50                  55

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
ggcagatctg gcctgtctgt gaat                                      24

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
cctctagatc tgttctatat cagattg                                   27

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
ggtccggatc cctagttttg atgaggg                                   27

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
gatcttttat tattattatt agttcg                                    26

<210> SEQ ID NO 11
<211> LENGTH: 26
<212> TYPE: DNA
```

-continued

<213> ORGANISM: Artificial Sequence
<220> FEATURE:
<223> OTHER INFORMATION: Synthetic

<400> SEQUENCE: 11
gatccgaact aataataata ataaaa                                              26

<210> SEQ ID NO 12
<211> LENGTH: 48
<212> TYPE: DNA
<213> ORGANISM: Artificial Sequence
<220> FEATURE:
<223> OTHER INFORMATION: Synthetic

<400> SEQUENCE: 12
gatccgggaa ggcgggcgct gggggcgctg cggcgctgcg ctccacct                      48

<210> SEQ ID NO 13
<211> LENGTH: 49
<212> TYPE: DNA
<213> ORGANISM: Artificial Sequence
<220> FEATURE:
<223> OTHER INFORMATION: Synthetic

<400> SEQUENCE: 13
gatctaggtg gagcgcagcg ccgcagcgcc cccagcgccc gccttcccg                     49

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gcataataaa aaaaattagt                                                     20

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
actaattttt tttatttatg c                                                   21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
ctgttttttt tagtattaag c                                                   21

<210> SEQ ID NO 17
<211> LENGTH: 21
<212> TYPE: DNA
<213> ORGANISM: c
<220> FEATURE:
<223> OTHER INFORMATION: Synthetic

<400> SEQUENCE: 17
gcttaatact aaaaaaaaca g                                                   21

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
gatcttaaca gtaataataa atatct                                    26

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
gatcagatat ttattattac tgttaa                                    26

<210> SEQ ID NO 20
<211> LENGTH: 33
<212> TYPE: DNA
<213> ORGANISM: Artificial Sequence
<220> FEATURE:
<223> OTHER INFORMATION: Synthetic

<400> SEQUENCE: 20
gacccgggat ccatgctgga acgtcgttgc agg                            33

<210> SEQ ID NO 21
<211> LENGTH: 31
<212> TYPE: DNA
<213> ORGANISM: Artificial Sequence
<220> FEATURE:
<223> OTHER INFORMATION: Synthetic

<400> SEQUENCE: 21
gacccgggat ccgggagatg ccgtcgaccg c                              31

<210> SEQ ID NO 22
<211> LENGTH: 33
<212> TYPE: DNA
<213> ORGANISM: Artificial Sequence
<220> FEATURE:
<223> OTHER INFORMATION: Synthetic

<400> SEQUENCE: 22
gacccgggat ccgtacctct gaaaccggcc cag                            33

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
gacccgggat cctcagacat cgtgcttctt ctg                            33

<210> SEQ ID NO 24
<211> LENGTH: 33
<212> TYPE: DNA
<213> ORGANISM: Artificial Sequence
<220> FEATURE:

<223> OTHER INFORMATION: Synthetic

<400> SEQUENCE: 24
gacccgggat cctgggccgg ttccagaggt acc        33

<210> SEQ ID NO 25
<211> LENGTH: 33
<212> TYPE: DNA
<213> ORGANISM: Artificial Sequence
<220> FEATURE:
<223> OTHER INFORMATION: Synthetic

<400> SEQUENCE: 25
gacccgggat ccgcggtcga cggcatctcc acc        33

<210> SEQ ID NO 26
<211> LENGTH: 46
<212> TYPE: DNA
<213> ORGANISM: Artificial Sequence
<220> FEATURE:
<223> OTHER INFORMATION: Synthetic

<400> SEQUENCE: 26
gacccgggat ccgaattctc gcttgtgaat cttgctgtga gacagc        46

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
gacccgggat cctccgaggg gtcggcccag gcg        33

<210> SEQ ID NO 28
<211> LENGTH: 36
<212> TYPE: DNA
<213> ORGANISM: Artificial Sequence
<220> FEATURE:
<223> OTHER INFORMATION: Synthetic

<400> SEQUENCE: 28
gacccgggat ccgagggagg gggggcttc gatcgg        36

<210> SEQ ID NO 29
<211> LENGTH: 45
<212> TYPE: DNA
<213> ORGANISM: Artificial Sequence
<220> FEATURE:
<223> OTHER INFORMATION: Synthetic

<400> SEQUENCE: 29
gacccgggat ccgaattcta cagctgcgac gactgcggca ggagc        45

<210> SEQ ID NO 30
<211> LENGTH: 11
<212> TYPE: PRT
<213> ORGANISM: Homo Sapiens

<400> SEQUENCE: 30

Val Ala Glu Ala Leu Glu Glu Ala Ala Ala Lys
 1               5                  10

<210> SEQ ID NO 31

-continued

```
<211> LENGTH: 16
<212> TYPE: PRT
<213> ORGANISM: Homo Sapiens

<400> SEQUENCE: 31

Asn Leu Val Ser His Arg Arg Ile His Thr Gly Glu Arg Pro Tyr Ala
 1               5                   10                  15

<210> SEQ ID NO 32
<211> LENGTH: 24
<212> TYPE: PRT
<213> ORGANISM: Homo Sapiens

<400> SEQUENCE: 32

His Arg Cys Ala His Cys Arg Arg His Phe Pro Gly Trp Val Ala Leu
 1               5                   10                  15

Trp Leu His Thr Arg Arg Cys Gln
            20

<210> SEQ ID NO 33
<211> LENGTH: 24
<212> TYPE: PRT
<213> ORGANISM: Homo Sapiens

<400> SEQUENCE: 33

Leu Pro Cys Pro Glu Cys Gly Arg Arg Phe Arg His Ala Pro Phe Leu
 1               5                   10                  15

Ala Leu His Arg Gln Val His Ala
            20

<210> SEQ ID NO 34
<211> LENGTH: 24
<212> TYPE: PRT
<213> ORGANISM: Homo Sapiens

<400> SEQUENCE: 34

Phe Ala Cys His Leu Cys Gly Gln Ser Phe Arg Gly Trp Val Ala Leu
 1               5                   10                  15

Val Leu His Leu Leu Ala His Ser
            20

<210> SEQ ID NO 35
<211> LENGTH: 24
<212> TYPE: PRT
<213> ORGANISM: Homo Sapiens

<400> SEQUENCE: 35

Ile Ala Cys Pro Lys Cys Glu Arg Arg Phe Trp Arg Arg Lys Gln Leu
 1               5                   10                  15

Arg Ala His Leu Arg Arg Cys His
            20

<210> SEQ ID NO 36
<211> LENGTH: 24
<212> TYPE: PRT
<213> ORGANISM: Homo Sapiens

<400> SEQUENCE: 36

Phe Ile Cys Gly Asn Cys Gly Arg Ser Phe Ala Gln Trp Asp Gln Leu
 1               5                   10                  15

Val Ala His Lys Arg Val His Val
            20
```

<210> SEQ ID NO 37
<211> LENGTH: 24
<212> TYPE: PRT
<213> ORGANISM: Homo Sapiens

<400> SEQUENCE: 37

Phe Gln Cys Ala Cys Cys Gly Lys Arg Phe Arg His Lys Pro Asn Leu
 1               5                  10                  15

Ile Ala His Arg Arg Val His Thr
            20

<210> SEQ ID NO 38
<211> LENGTH: 24
<212> TYPE: PRT
<213> ORGANISM: Homo Sapiens

<400> SEQUENCE: 38

His Gln Cys Pro Glu Cys Gly Lys Arg Phe Thr Asn Lys Pro Tyr Leu
 1               5                  10                  15

Thr Ser His Arg Arg Ile His Thr
            20

<210> SEQ ID NO 39
<211> LENGTH: 24
<212> TYPE: PRT
<213> ORGANISM: Homo Sapiens

<400> SEQUENCE: 39

Tyr Pro Cys Lys Glu Cys Gly Arg Arg Phe Arg His Lys Pro Asn Leu
 1               5                  10                  15

Leu Ser His Ser Lys Ile His Lys
            20

<210> SEQ ID NO 40
<211> LENGTH: 23
<212> TYPE: PRT
<213> ORGANISM: Homo Sapiens

<400> SEQUENCE: 40

Tyr Ser Cys Asp Asp Cys Gly Arg Ser Phe Arg Leu Glu Arg Phe Leu
 1               5                  10                  15

Arg Ala His Gln Arg His Asp
            20

<210> SEQ ID NO 41
<211> LENGTH: 24
<212> TYPE: PRT
<213> ORGANISM: Homo Sapiens

<400> SEQUENCE: 41

Phe Thr Cys Ala Glu Cys Gly Lys Asn Phe Gly Lys Lys Thr His Leu
 1               5                  10                  15

Val Ala His Ser Pro Val His Ser
            20

<210> SEQ ID NO 42
<211> LENGTH: 24
<212> TYPE: PRT
<213> ORGANISM: Homo Sapiens

<400> SEQUENCE: 42

Phe Ala Cys Glu Glu Cys Gly Arg Arg Phe Ser Gln Gly Ser His Leu

```
                1               5              10              15
Ala Ala His Arg Pro Asp His Ala
            20

<210> SEQ ID NO 43
<211> LENGTH: 24
<212> TYPE: PRT
<213> ORGANISM: Homo Sapiens

<400> SEQUENCE: 43

Phe Val Cys Pro Asp Cys Gly Lys Ala Phe Arg His Lys Pro Tyr Leu
  1               5                  10                  15

Ala Arg His Arg Arg Ile His Thr
            20

<210> SEQ ID NO 44
<211> LENGTH: 24
<212> TYPE: PRT
<213> ORGANISM: Homo Sapiens

<400> SEQUENCE: 44

Tyr Val Cys Pro Asp Cys Gly Lys Ala Phe Ser Gln Lys Ser Asn Leu
  1               5                  10                  15

Val Ser His Arg Arg Ile His Thr
            20

<210> SEQ ID NO 45
<211> LENGTH: 24
<212> TYPE: PRT
<213> ORGANISM: Homo Sapiens

<400> SEQUENCE: 45

Tyr Ala Cys Pro Asp Cys Asp Arg Ser Phe Ser Gln Lys Ser Asn Leu
  1               5                  10                  15

Ile Thr His Arg Lys Ser His Ile
            20

<210> SEQ ID NO 46
<211> LENGTH: 24
<212> TYPE: PRT
<213> ORGANISM: Homo Sapiens

<400> SEQUENCE: 46

Phe Cys Cys Ala Ile Cys Gly Gln Thr Phe Asp Asp Glu Glu Arg Leu
  1               5                  10                  15

Leu Ala His Gln Lys Lys His Asp
            20

<210> SEQ ID NO 47
<211> LENGTH: 24
<212> TYPE: PRT
<213> ORGANISM: Homo Sapiens
<220> FEATURE:
<221> NAME/KEY: VARIANT
<222> LOCATION: (1)...(2)
<223> OTHER INFORMATION: Xaa is any amino acid.
<220> FEATURE:
<221> NAME/KEY: VARIANT
<222> LOCATION: (4)...(5)
<223> OTHER INFORMATION: Xaa is any amino acid.
<220> FEATURE:
<221> NAME/KEY: VARIANT
<222> LOCATION: (7)...(9)
<223> OTHER INFORMATION: Xaa is any amino acid.
<220> FEATURE:
```

-continued

```
<221> NAME/KEY: VARIANT
<222> LOCATION: (11)...(15)
<223> OTHER INFORMATION: Xaa is any amino acid.
<220> FEATURE:
<221> NAME/KEY: VARIANT
<222> LOCATION: (17)...(18)
<223> OTHER INFORMATION: Xaa is any amino acid.
<220> FEATURE:
<221> NAME/KEY: VARIANT
<222> LOCATION: (20)...(22)
<223> OTHER INFORMATION: Xaa is any amino acid.
<220> FEATURE:
<221> NAME/KEY: VARIANT
<222> LOCATION: (24)...(24)
<223> OTHER INFORMATION: Xaa is any amino acid.

<400> SEQUENCE: 47

Xaa Xaa Cys Xaa Xaa Cys Xaa Xaa Phe Xaa Xaa Xaa Xaa Xaa Leu
 1               5                  10                  15

Xaa Xaa His Xaa Xaa Xaa His Xaa
             20

<210> SEQ ID NO 48
<211> LENGTH: 702
<212> TYPE: DNA
<213> ORGANISM: Homo Sapiens
<220> FEATURE:
<221> NAME/KEY: CDS
<222> LOCATION: (1)...(702)

<400> SEQUENCE: 48 atg ctg gaa cgt cgt tgc agg ggc ccc ctg gcc atg ggc ctg gcc cag      48
Met Leu Glu Arg Arg Cys Arg Gly Pro Leu Ala Met Gly Leu Ala Gln
 1               5                  10                  15 ccc cga ctc ctt tct ggg ccc tcc cag gag tca ccc cag acc ctg ggg      96
Pro Arg Leu Leu Ser Gly Pro Ser Gln Glu Ser Pro Gln Thr Leu Gly
             20                  25                  30 aag gag tcc cgc ggg ctg agg caa caa ggc acg tca gtg gcc cag tct     144
Lys Glu Ser Arg Gly Leu Arg Gln Gln Gly Thr Ser Val Ala Gln Ser
         35                  40                  45 ggt gcc caa gcc cca ggc agg gcc cat cgc tgt gcc cac tgt cga agg     192
Gly Ala Gln Ala Pro Gly Arg Ala His Arg Cys Ala His Cys Arg Arg
     50                  55                  60 cac ttc cct ggc tgg gtg gct ctg tgg ctt cac acc cgc cgg tgc cag     240
His Phe Pro Gly Trp Val Ala Leu Trp Leu His Thr Arg Arg Cys Gln
 65                  70                  75                  80 gcc cgg ctg ccc ttg ccc tgc cct gag tgt ggc cgt cgc ttt cgc cat     288
Ala Arg Leu Pro Leu Pro Cys Pro Glu Cys Gly Arg Arg Phe Arg His
                 85                  90                  95 gcc ccc ttc tta gca ctg cac cgc cag gtc cat gct gct gcc acc cca     336
Ala Pro Phe Leu Ala Leu His Arg Gln Val His Ala Ala Ala Thr Pro
                100                 105                 110 gac ctg ggc ttt gcc tgc cac ctc tgt ggg cag agc ttc cga ggc tgg     384
Asp Leu Gly Phe Ala Cys His Leu Cys Gly Gln Ser Phe Arg Gly Trp
            115                 120                 125 gtg gcc ctg gtt ctg cat ctg ctg gcc cat tca gct gca aag caa ccc     432
Val Ala Leu Val Leu His Leu Leu Ala His Ser Ala Ala Lys Gln Pro
        130                 135                 140 atc gct tgt ccc aaa tgc gag aga cgc ttc tgg cga cga aag cag ctt     480
Ile Ala Cys Pro Lys Cys Glu Arg Arg Phe Trp Arg Arg Lys Gln Leu
145                 150                 155                 160 cga gct cat ctg cgg cgg tgc cac cct ccc gcc ccg gag gcc cgg ccc     528
Arg Ala His Leu Arg Arg Cys His Pro Pro Ala Pro Glu Ala Arg Pro
                165                 170                 175
```

| | | |
|---|---|---|
| ttc ata tgc ggc aac tgt ggc cgg agc ttt gcc cag tgg gac cag cta<br>Phe Ile Cys Gly Asn Cys Gly Arg Ser Phe Ala Gln Trp Asp Gln Leu<br>                180                            185                          190 | | 576 |
| gtt gcc cac aag cgg gtg cac gta gct gag gcc ctg gag gag gcc gca<br>Val Ala His Lys Arg Val His Val Ala Glu Ala Leu Glu Glu Ala Ala<br>                195                            200                          205 | | 624 |
| gcc aag gct ctg ggg ccc cgg ccc agg ggc cgc ccc gcg gtg acc gcc<br>Ala Lys Ala Leu Gly Pro Arg Pro Arg Gly Arg Pro Ala Val Thr Ala<br>                210                            215                          220 | | 672 |
| ccc cgg ccc ggt gga gat gcc gtc gac cgc<br>Pro Arg Pro Gly Gly Asp Ala Val Asp Arg<br>225                            230 | | 702 |

<210> SEQ ID NO 49
<211> LENGTH: 234
<212> TYPE: PRT
<213> ORGANISM: Homo Sapiens

<400> SEQUENCE: 49

Met Leu Glu Arg Arg Cys Arg Gly Pro Leu Ala Met Gly Leu Ala Gln
 1               5                  10                  15

Pro Arg Leu Leu Ser Gly Pro Ser Gln Glu Ser Pro Gln Thr Leu Gly
            20                  25                  30

Lys Glu Ser Arg Gly Leu Arg Gln Gln Gly Thr Ser Val Ala Gln Ser
        35                  40                  45

Gly Ala Gln Ala Pro Gly Arg Ala His Arg Cys Ala His Cys Arg Arg
    50                  55                  60

His Phe Pro Gly Trp Val Ala Leu Trp Leu His Thr Arg Arg Cys Gln
65                  70                  75                  80

Ala Arg Leu Pro Leu Pro Cys Pro Glu Cys Gly Arg Arg Phe Arg His
                85                  90                  95

Ala Pro Phe Leu Ala Leu His Arg Gln Val His Ala Ala Ala Thr Pro
            100                 105                 110

Asp Leu Gly Phe Ala Cys His Leu Cys Gly Gln Ser Phe Arg Gly Trp
        115                 120                 125

Val Ala Leu Val Leu His Leu Ala His Ser Ala Lys Gln Pro
    130                 135                 140

Ile Ala Cys Pro Lys Cys Glu Arg Arg Phe Trp Arg Arg Lys Gln Leu
145                 150                 155                 160

Arg Ala His Leu Arg Arg Cys His Pro Pro Ala Pro Glu Ala Arg Pro
                165                 170                 175

Phe Ile Cys Gly Asn Cys Gly Arg Ser Phe Ala Gln Trp Asp Gln Leu
            180                 185                 190

Val Ala His Lys Arg Val His Val Ala Glu Ala Leu Glu Glu Ala Ala
        195                 200                 205

Ala Lys Ala Leu Gly Pro Arg Pro Arg Gly Arg Pro Ala Val Thr Ala
    210                 215                 220

Pro Arg Pro Gly Gly Asp Ala Val Asp Arg
225                 230

<210> SEQ ID NO 50
<211> LENGTH: 441
<212> TYPE: DNA
<213> ORGANISM: Homo Sapiens
<220> FEATURE:
<221> NAME/KEY: CDS
<222> LOCATION: (1)...(441)

<400> SEQUENCE: 50

```
ggt gga gat gcc gtc gac cgc ccc ttc cag tgt gcc tgt tgt ggc aag      48
Gly Gly Asp Ala Val Asp Arg Pro Phe Gln Cys Ala Cys Cys Gly Lys
 1               5                  10                  15 cgc ttc cgg cac aag ccc aac ttg atc gct cac cgc gcc gtg cac acg      96
Arg Phe Arg His Lys Pro Asn Leu Ile Ala His Arg Arg Val His Thr
                 20                  25                  30 ggc gag cgg ccc cac cag tgc ccc gag tgc ggg aag cgc ttt acc aat     144
Gly Glu Arg Pro His Gln Cys Pro Glu Cys Gly Lys Arg Phe Thr Asn
             35                  40                  45 aag ccc tat ctg act tcg cac cgg cgc atc cac acc ggc gag aag ccc     192
Lys Pro Tyr Leu Thr Ser His Arg Arg Ile His Thr Gly Glu Lys Pro
         50                  55                  60 tac ccg tgc aaa gag tgc ggc cgc cgc ttc cgg cac aaa ccc aac ctg     240
Tyr Pro Cys Lys Glu Cys Gly Arg Arg Phe Arg His Lys Pro Asn Leu
 65                  70                  75                  80 ctg tct cac agc aag att cac aag cga tcc gag ggg tcg gcc cag gcc     288
Leu Ser His Ser Lys Ile His Lys Arg Ser Glu Gly Ser Ala Gln Ala
                 85                  90                  95 gcc ccc ggc ccg ggg agc ccc cag ctg cca gcc ggc ccc cag gag tcc     336
Ala Pro Gly Pro Gly Ser Pro Gln Leu Pro Ala Gly Pro Gln Glu Ser
            100                 105                 110 gcg gcc gag ccc acc ccg gcg gta cct ctg aaa ccg gcc cag gag ccg     384
Ala Ala Glu Pro Thr Pro Ala Val Pro Leu Lys Pro Ala Gln Glu Pro
        115                 120                 125 ccg cca ggg gcc ccg cca gag cac ccg cag gac ccg atc gaa gcc ccc     432
Pro Pro Gly Ala Pro Pro Glu His Pro Gln Asp Pro Ile Glu Ala Pro
    130                 135                 140 ccc tcc ctc                                                         441
Pro Ser Leu
145

<210> SEQ ID NO 51
<211> LENGTH: 147
<212> TYPE: PRT
<213> ORGANISM: Homo Sapiens

<400> SEQUENCE: 51

Gly Gly Asp Ala Val Asp Arg Pro Phe Gln Cys Ala Cys Cys Gly Lys
 1               5                  10                  15

Arg Phe Arg His Lys Pro Asn Leu Ile Ala His Arg Arg Val His Thr
                 20                  25                  30

Gly Glu Arg Pro His Gln Cys Pro Glu Cys Gly Lys Arg Phe Thr Asn
             35                  40                  45

Lys Pro Tyr Leu Thr Ser His Arg Arg Ile His Thr Gly Glu Lys Pro
         50                  55                  60

Tyr Pro Cys Lys Glu Cys Gly Arg Arg Phe Arg His Lys Pro Asn Leu
 65                  70                  75                  80

Leu Ser His Ser Lys Ile His Lys Arg Ser Glu Gly Ser Ala Gln Ala
                 85                  90                  95

Ala Pro Gly Pro Gly Ser Pro Gln Leu Pro Ala Gly Pro Gln Glu Ser
            100                 105                 110

Ala Ala Glu Pro Thr Pro Ala Val Pro Leu Lys Pro Ala Gln Glu Pro
        115                 120                 125

Pro Pro Gly Ala Pro Pro Glu His Pro Gln Asp Pro Ile Glu Ala Pro
    130                 135                 140

Pro Ser Leu
145
```

<210> SEQ ID NO 52
<211> LENGTH: 16
<212> TYPE: DNA
<213> ORGANISM: Artificial Sequence
<220> FEATURE:
<223> OTHER INFORMATION: Synthetic

<400> SEQUENCE: 52
aatttaccgt ttctat                                                    16

<210> SEQ ID NO 53
<211> LENGTH: 16
<212> TYPE: DNA
<213> ORGANISM: Artificial Sequence
<220> FEATURE:
<223> OTHER INFORMATION: Synthetic

<400> SEQUENCE: 53
ccttccttct tattca                                                    16

<210> SEQ ID NO 54
<211> LENGTH: 16
<212> TYPE: DNA
<213> ORGANISM: Artificial Sequence
<220> FEATURE:
<223> OTHER INFORMATION: Synthetic

<400> SEQUENCE: 54
ttcatttgat tttatt                                                    16

<210> SEQ ID NO 55
<211> LENGTH: 16
<212> TYPE: DNA
<213> ORGANISM: Artificial Sequence
<220> FEATURE:
<223> OTHER INFORMATION: Synthetic

<400> SEQUENCE: 55
ttttataatt cctatt                                                    16

<210> SEQ ID NO 56
<211> LENGTH: 16
<212> TYPE: DNA
<213> ORGANISM: Artificial Sequence
<220> FEATURE:
<223> OTHER INFORMATION: Synthetic

<400> SEQUENCE: 56
tctaattttc ttttta                                                    16

<210> SEQ ID NO 57
<211> LENGTH: 16
<212> TYPE: DNA
<213> ORGANISM: Artificial Sequence
<220> FEATURE:
<223> OTHER INFORMATION: Synthetic

<400> SEQUENCE: 57
tgttttgatt ttttat                                                    16

<210> SEQ ID NO 58
<211> LENGTH: 16
<212> TYPE: DNA
<213> ORGANISM: Artificial Sequence
<220> FEATURE:
<223> OTHER INFORMATION: Synthetic

```
<400> SEQUENCE: 58
tattttattt attaat                                              16

<210> SEQ ID NO 59
<211> LENGTH: 16
<212> TYPE: DNA
<213> ORGANISM: Artificial Sequence
<220> FEATURE:
<223> OTHER INFORMATION: Synthetic

<400> SEQUENCE: 59
ttcttttttc ataaat                                              16

<210> SEQ ID NO 60
<211> LENGTH: 16
<212> TYPE: DNA
<213> ORGANISM: Artificial Sequence
<220> FEATURE:
<223> OTHER INFORMATION: Synthetic

<400> SEQUENCE: 60
tattatttta tgttga                                              16

<210> SEQ ID NO 61
<211> LENGTH: 16
<212> TYPE: DNA
<213> ORGANISM: Artificial Sequence
<220> FEATURE:
<223> OTHER INFORMATION: Synthetic

<400> SEQUENCE: 61
tttttaaatt tttta                                               16

<210> SEQ ID NO 62
<211> LENGTH: 16
<212> TYPE: DNA
<213> ORGANISM: Artificial Sequence
<220> FEATURE:
<223> OTHER INFORMATION: Synthetic

<400> SEQUENCE: 62
gatgaatttt tttta                                               16

<210> SEQ ID NO 63
<211> LENGTH: 16
<212> TYPE: DNA
<213> ORGANISM: Artificial Sequence
<220> FEATURE:
<223> OTHER INFORMATION: Synthetic

<400> SEQUENCE: 63
tactttatgg ttaagc                                              16

<210> SEQ ID NO 64
<211> LENGTH: 16
<212> TYPE: DNA
<213> ORGANISM: Artificial Sequence
<220> FEATURE:
<223> OTHER INFORMATION: Synthetic

<400> SEQUENCE: 64
ctattactgt tttctg                                              16

<210> SEQ ID NO 65
```

-continued

```
<211> LENGTH: 16
<212> TYPE: DNA
<213> ORGANISM: Artificial Sequence
<220> FEATURE:
<223> OTHER INFORMATION: Synthetic

<400> SEQUENCE: 65 ttttttagt ttctta                                                    16

<210> SEQ ID NO 66
<211> LENGTH: 16
<212> TYPE: DNA
<213> ORGANISM: Artificial Sequence
<220> FEATURE:
<223> OTHER INFORMATION: Synthetic

<400> SEQUENCE: 66
tactttatgg ttaacg                                                   16

<210> SEQ ID NO 67
<211> LENGTH: 22
<212> TYPE: DNA
<213> ORGANISM: Cricetulus sp.

<400> SEQUENCE: 67
tttttttatt attattatta gt                                            22

<210> SEQ ID NO 68
<211> LENGTH: 72
<212> TYPE: PRT
<213> ORGANISM: Homo Sapiens

<400> SEQUENCE: 68

His Ser Lys Ile His Lys Arg Ser Glu Gly Ser Ala Gln Ala Ala Pro
 1               5                  10                  15

Gly Pro Gly Ser Pro Gln Leu Pro Ala Gly Pro Gln Glu Ser Ala Ala
            20                  25                  30

Glu Pro Thr Pro Ala Val Pro Leu Lys Pro Ala Gln Glu Pro Pro Pro
        35                  40                  45

Gly Ala Pro Pro Glu His Pro Gln Asp Pro Ile Glu Ala Pro Pro Ser
    50                  55                  60

Leu Tyr Ser Cys Asp Asp Cys Gly
 65                 70
```

METHODS AND PRODUCTS FOR DELIVERING NUCLEIC ACIDS

RELATED APPLICATIONS

This application claims priority to U.S. Provisional Patent Application filed Jan. 4, 1999, entitled "METHODS AND PRODUCTS FOR DELIVERING NUCLEIC ACIDS", Ser. No. 60/114,745, and related U.S. Provisional Patent Application filed Jan. 4, 1999, entitled "RIP60 NUCLEIC ACID AND POLYPEPTIDE SEQUENCES AND USES THEREFORE", Ser. No. 60/114,743.

BACKGROUND OF THE INVENTION

The ability to transfer nucleic acids into cells has vast experimental and therapeutic implications. Many different chemical, electrochemical and biological approaches have been used for this purpose. In vitro chemical methods include osmotic shock transformation of prokaryotic cells and calcium phosphate transfection and liposome-mediated transfer for eukaryotic cells. Nucleic acids, namely DNA, have also been delivered to cells by electroporation. While this latter approach is amenable to nucleic acid transfer in vitro, it is inherently unsuitable for in vivo use. Biological approaches have focused on viral strategies which include retroviral and most recently adenoviral mediated gene transfer into cells in culture and, in some instances, cells in vivo. A common disadvantage of the above-mentioned strategies is their inability to specifically target cells for nucleic acid delivery. Targeting of cell subsets usually requires the selective harvesting of cells followed by in vitro delivery and re-introduction in vivo.

Viral mediated gene transfer requires the in vitro production of defective viral particles which encapsulate a nucleic acid of a finite size. The encapsulated nucleic acid, usually referred to as a viral vector, is a recombinant nucleic acid which contains a gene(s) of interest cloned between 5' and 3' flanking viral cis elements. The cis elements are required for integration into the host genome yet they are also capable of transcriptional regulation. As a result, these elements have the potential to interfere with the transcriptional activity of the cloned gene(s). Another limitation of viral mediated gene transfer is the need for and the difficulty in achieving high titre viral stocks. In vivo infection with viruses, when applicable, is generally not effective given the in vivo dilution of viral particles. Additionally, although both retroviral and adenoviral methods employ replication-defective viral particles, the possibility of producing replication-competent viruses and thereby causing active infection in vivo is an inherent danger of both systems.

For retroviral mediated gene transfer to occur, target cells whether in vitro or in vivo must be in a cycling status. Since retroviruses package nucleic acid in the form of RNA, reverse transcription of the RNA to DNA is required for integration into the host genome from where the gene exerts its effects. Cells which divide infrequently or never at all, such as some classes of stem cells or terminally differentiated end cells, are usually less amenable to gene transfer via retroviral infection as compared to rapidly dividing cells. Thus diseases for which a long-term cure is dependent upon stem cell or end cell manipulation are poor candidates for gene therapy treatment using retroviral transfection. Retroviral use is also limited to the restricted range of host infectivity specific to each strain of virus. In contrast adenoviruses which contain double stranded DNA do not require target cells to be cycling for infection, integration and propagation.

DNA has also been delivered to cells using receptor-mediated endocytosis. In this approach, DNA is initially complexed with polycations such as polylysine for condensation and charge neutralization purposes. Ligands for cell surface receptors, such as transferrin, are then coupled either biochemically or enzymatically to the polylysine moieties. In a further modification, the transferrin molecules are coupled to the outer surface of inactivated adenoviral particles. The adenoviral particles can effect the release of the DNA/polylysine/transferrin complex from endosomes prior to lysosome mediated degradation. The transfer of up to 48 kilobases (kb) of DNA has been reported using this approach. Cotten et al., PNAS v. 89, p.6094–6098 (1992).

In contrast to the use of polycations for complexing DNA, other approaches have incorporated specific DNA binding domains which recognize and bind distinct nucleic acid consensus sequences. An example of this is the use of the GAL4 DNA binding domain of yeast which selectively binds to a 17 bp sequence. Thus a nucleic acid to be delivered must usually be modified to incorporate artificial GAL4 binding sites. Likewise, other approaches which rely on a consensus sequence dependent DNA binding domain will similarly require modification of the transferred nucleic acid.

SUMMARY OF THE INVENTION

The invention relates to products and methods for delivering nucleic acids of various sizes into cells either in vitro or in vivo. The invention involves a modular polypeptide which binds and condenses nucleic acid molecules and, depending on its particular composition, can perform various other functions either prior to or after delivery to a cell.

One aspect of the invention concerns a non-viral nucleic acid delivery complex comprising a modular polypeptide. The modular polypeptide comprises a nucleic acid binding domain and a nucleic acid condensation domain that respectively bind and condense a nucleic acid molecule of more than 50 kilobases in length. The modular polypeptide further comprises one or more of the following polypeptides: a cell recognition domain, a protein transduction domain, a protein degradation domain, an intracellular targeting domain, a protein interaction domain, an epitope domain, and a protein purification domain. Depending on the embodiment of the invention, the modular polypeptide can contain one, two, three, four, five, six, seven or more of the above-listed polypeptide domains. In some embodiments several copies of the same type of domain may be included in the modular polypeptide.

According to one embodiment of the invention, the modular polypeptide delivers to a cell a nucleic acid equal to or more than 100 kilobases in length. In a preferred embodiment, the nucleic acid delivered to a cell is equal to or more than 200 kilobases in length. In another embodiment the nucleic acid delivered to the cell is equal to or more than 300 to 400 kilobases in length. In yet other embodiments the nucleic acid delivered to the cell is equal to every integer length between 50 and 500 kilobases.

In another embodiment, the invention relates to a modular polypeptide with a nucleic acid binding domain that recognizes and binds a nucleic acid molecule in a sequence independent manner. In a further embodiment, the nucleic acid binding domain interacts with an ATT-rich sequence of a nucleic acid. In important embodiments, the nucleic acid binding domain recognizes common nucleic acid sequences such as ATT triplets or T-rich tracts of nucleic acids. In these latter embodiments, no modification of the nucleic acid to be complexed with the nucleic acid binding domain is necessary since the nucleic acid will invariably contain such ATT-rich or T-rich sequences.

In one embodiment of the invention, the modular polypeptide is complexed with a nucleic acid. The nucleic acid can be a sense or an antisense nucleic acid molecule. Depending on the embodiment, the nucleic acid can be a DNA, RNA or a DNA/RNA hybrid molecule. In a further embodiment, the nucleic acid molecule is an unmodified fragment of chromosomal DNA. In another embodiment, the nucleic acid is a bacterial artificial chromosome (BAC). In still another embodiment, the nucleic acid is a yeast artificial chromosome (YAC). The nucleic acid can be single or double stranded.

In yet another embodiment, the nucleic acid binding domain of the invention is selected from the group consisting of a zinc finger domain, a basic helix-loop-helix domain, a homeodomain, and a native or modified antibody or a fragment thereof. In a preferred embodiment, the nucleic acid binding domain is a zinc finger domain. The zinc finger domain may be the Z1 or Z3 zinc finger domain of the human zinc finger protein RIP60. In an even more preferred embodiment, the nucleic acid binding domain is the Z2 zinc finger domain of the human zinc finger protein RIP60.

In still another embodiment of the invention, the nucleic acid condensation domain is a multimerization domain. In yet another embodiment, the nucleic acid condensation domain is selected from the group consisting of a zinc finger domain, a homeodomain, a paired amphipathic helices domain, or a proline-rich domain. In a preferred embodiment, the condensation domain is a proline-rich domain. In an even more preferred embodiment, the proline rich domain is the proline rich region of human zinc finger protein RIP60.

In another embodiment the nucleic acid binding and condensation domains are located within the same domain. In a preferred embodiment, the nucleic acid binding domain and the condensation domain are the Z2 domain of the human zinc finger protein RIP60. In another embodiment, the nucleic acid binding domain and the condensation domain are the Z2 domain and the proline rich region of the human zinc finger protein RIP60.

In another embodiment, a phosphorylation site is present in the nucleic acid binding domain and/or the nucleic acid condensation domain. In a preferred embodiment, the nucleic acid condensation domain further comprises a phosphorylation site. In an important embodiment, the phosphorylation site is a casein kinase II phosphorylation site. In an even more preferred embodiment, the phosphorylation site, the nucleic acid binding domain and the condensation domain are the Z2 domain and the proline rich region of human zinc finger protein RIP60.

In one embodiment of the invention, the modular polypeptide contains a cell recognition domain. In another embodiment, the invention provides for a cell recognition domain which binds to a cell surface molecule, which can include but is not limited to a cell surface receptor, such as an Fc or cytokine receptor. In another embodiment, the cell recognition domain binds to an extracellular matrix molecule. In yet another embodiment, the cell recognition domain binds to a carbohydrate moiety. In still a further embodiment, the cell recognition domain is an antibody or an antibody fragment.

In one embodiment of the invention, the modular polypeptide contains a protein degradation domain. In a further embodiment, the protein degradation domain is a PEST sequence.

In another embodiment of the invention, the modular polypeptide contains an intracellular targeting domain. In a further embodiment, the intracellular targeting domain is a nuclear localization signal sequence. In yet a further embodiment, the intracellular targeting domain causes the release of the nucleic acid delivery complex from an endosome prior to lysosomal degradation.

In still another embodiment of the invention, the modular polypeptide contains a protein interaction domain. In a further embodiment, the protein interaction domain associates with one or more of the following polypeptides: a signal transduction molecule, a carbohydrate expressing polypeptide, a hormone, a hormone receptor, or a transcription factor. In an important embodiment, the protein interaction domain is a proline rich domain or an SH3 binding domain. In another important embodiment, the protein interaction domain is the proline rich region of human zinc finger protein RIP60.

In another embodiment of the invention, the modular polypeptide contains an epitope domain. The epitope domain can be, but is not limited to, a hemaglutinnin tag, a FLAG tag, a V5 tag, a myc tag, or a T7 tag. In one preferred embodiment, the epitope domain is a hemaglutinnin tag. In another preferred embodiment, the epitope domain is a FLAG tag.

In a further embodiment of the invention, the modular polypeptide contains a protein purification domain. The protein purification domain can be, but is not limited to, a GST sequence tag, a hexahistidine or polyhistidine tag, a Protein A tag, a biotin tag, a chitin tag, or a maltose binding domain. In a preferred embodiment, the protein purification domain is a GST sequence tag. In another preferred embodiment, the protein purification domain is a hexahistidine tag.

In one aspect, the invention provides for a pharmaceutical composition comprising a pharmaceutically effective amount of an agent which comprises the nucleic acid delivery complex of the invention and a pharmaceutically acceptable carrier. In another aspect, the invention relates to a kit which comprises the foregoing pharmaceutical composition and instructions for use thereof.

In yet another aspect, a method is provided for delivering to a cell a non-viral nucleic acid molecule encoding one or more polypeptides. The method involves delivering to a cell a non-viral nucleic acid in a nucleic acid delivery complex in an amount effective to deliver the nucleic acid to the cell. The nucleic acid comprises two or more native regulatory and structural nucleic acid elements for at least one of the encoded polypeptides selected from the group consisting of locus control regions, 5' and 3' flanking sequences, introns, promoters, enhancers, and coding sequences. In one embodiment, the nucleic acid contains three or more native regulatory and structural nucleic acid elements. In a further embodiment, the nucleic acid contains four or more native regulatory and structural nucleic acid elements. In yet a further embodiment, the nucleic acid contains five or more native regulatory and structural nucleic acid elements. In a preferred embodiment, the nucleic acid contains six native regulatory and structural nucleic acid elements. In a further embodiment, the nucleic acid is equal to or more than 50 kilobases in length. In a preferred embodiment, the nucleic acid is delivered to the cell using the foregoing nucleic acid delivery complex of the invention.

In yet another aspect, the invention relates to a method for delivering a nucleic acid into a cell comprising delivering to a cell a modular polypeptide complexed with a nucleic acid of more than 50 kilobases in length, in an amount effective to deliver the nucleic acid into the cell. In important embodiments, the modular polypeptide is the modular polypeptide of the invention. In important embodiments, the nucleic acid to be delivered to the cell is selected from the foregoing nucleic acids. In a further embodiment of the invention, the cell into which the nucleic acid is delivered is a eukaryotic cell, including but not limited to an animal cell, a human cell, an insect cell, a plant cell, a mouse cell, or a Drosophila cell. In another embodiment, the cell is a prokaryotic cell. In a further embodiment, the cell is in a suspension, a tissue or fragment thereof, or an organ or fragment thereof, in vitro or in vivo. In a further embodiment, the cell is derived from a subject with one or more genetic mutations. In yet another embodiment, the nucleic acid is delivered to the cell by passive or active transport. In yet a further embodiment of the invention, once in the cell, the nucleic acid can be acted upon by repair, transcription, replication or recombination machinery.

The invention also relates to the molecular cloning and characterization of RIP60, a zinc finger protein involved in cell division and nucleic acid replication.

The invention provides isolated RIP60 nucleic acid molecules, unique fragments of those molecules, expression vectors containing the foregoing, and host cells transfected with those molecules. The invention also provides isolated RIP60 polypeptides, and agents which bind RIP60 polypeptides, including antibodies.

According to one aspect of the invention, isolated nucleic acid molecules are provided that comprise: (a) nucleic acid molecules which hybridize under stringent conditions to a molecule consisting of a nucleic acid of SEQ ID NO:1, SEQ ID NO:3, SEQ ID NO:5 and SEQ ID NO:50 and which code for a polypeptide having RIP60 activity, (b) deletions, additions and substitutions of (a) which code for a polypeptide having RIP60 activity, (c) nucleic acid molecules that differ from the nucleic acid molecules of (a) or (b) in codon sequence due to the degeneracy of the genetic code, and (d) complements of (a), (b) or (c). In certain embodiments, the isolated nucleic acid molecule comprises SEQ ID NO:1. In other embodiments, the isolated nucleic acid molecule comprises SEQ ID NO:3, SEQ ID NO:5 or SEQ ID NO:50. In some embodiments, the isolated nucleic acid molecules are those that code for a polypeptide comprising SEQ ID NO:2. In some embodiments, the isolated nucleic acid molecules are those that code for a polypeptide comprising SEQ ID NO:4, SEQ ID NO:6 or SEQ ID NO:51. In an important embodiment, the nucleic acid molecules code for a native RIP60 polypeptide, including homologs and alleles. A native RIP60 polypeptide is one which possesses a native RIP60 function or activity, such as but not limited to DNA binding or protein multimerization. Another function or activity of a native RIP60 polypeptide is the ability to bind to either itself or to other proline rich region containing proteins, specifically through its proline rich region.

The invention in another aspect provides an isolated nucleic acid molecule selected from the group consisting of (a) a unique fragment of nucleic acid molecule of SEQ ID NO:1 of sufficient length to represent a sequence unique within the human genome, and (b) complements of (a), provided that the unique fragment includes a sequence of contiguous nucleotides which is not identical to a sequence selected from the sequence group consisting of (1) sequences having the GenBank and EMBL database accession numbers of Table 1, (2) complements of (1), and (3) fragments of (1) and (2).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, and (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween as if fully cited herein.

In other embodiments, the unique fragment encodes a peptide which is a fragment of a polypeptide consisting of SEQ ID NO:2.

According to another aspect, the invention provides expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules of the invention. In important embodiments, the isolated polypeptide is encoded by the nucleic acid of SEQ ID NO:1, giving rise to a ~62 kD polypeptide having the sequence of SEQ ID NO:2 that can bind to nucleic acids, preferably at ATT-rich regions and even more preferably at USR and DSR sequences, and form multimers on such nucleic acids. In certain embodiments, the isolated polypeptide is a polypeptide having RIP60 activity. Preferably, the polypeptide is a native RIP60 polypeptide. In important embodiments, the isolated polypeptide comprises SEQ ID NO:2. In still other embodiments, the isolated polypeptide comprises SEQ ID NO:4, SEQ ID NO:6 or SEQ ID NO:51.

In other embodiments, an isolated peptide is provided which comprises a fragment or variant of the foregoing polypeptides of sufficient length to represent a sequence unique within the human genome, and to identify a polypeptide having RIP60 activity or, in other embodiments, a native RIP60 polypeptide. The isolated peptide may comprise at least 6, at least 8, at least 9, at least 10, at least 11, at least 12, at least 14, at least 16, at least 18, least 20 contiguous amino acids having a sequence of a fragment of SEQ ID NO:2. Isolated peptides which are immunogenic are also provided.

According to another aspect of the invention, compositions are provided which comprise an isolated agent that binds selectively to a polypeptide having RIP60 activity, including a native RIP60 polypeptide, encoded by the foregoing isolated nucleic acid molecules of the invention. Preferably, the isolated agent binds selectively to a polypeptide comprising SEQ ID NO:2, SEQ ID NO:4, SEQ ID NO:6 or SEQ ID NO:51, or to a fragment thereof. In important embodiments, the isolated agent is a peptide. In a further embodiment, the peptide is an antibody or a fragment thereof (e.g., Fab, F(ab)$_2$, Fd and antibody fragments which include a CDR3 region which binds selectively to a polypeptide having RIP60 activity). In even more preferred embodiments, the antibody is a humanized antibody or a chimeric antibody. The isolated agent may be conjugated to a detectable label. The detectable label may be selected from the group consisting of a radioactive label, an enzyme, a biotin molecule, an avidin molecule or a fluorochrome.

In yet another aspect, the invention relates to a kit comprising a package including an agent that selectively binds the isolated nucleic acid molecules and polypeptides of the invention, a control for comparing with a measured or test value, instructions and optionally related materials. In a further embodiment, the kit contains a control which has a predetermined value for comparing to the measured or test value.

Another aspect of the invention is a method for determining the level of RIP60 expression in a sample from a subject. RIP60 expression is defined either as RIP60 mRNA expression or RIP60 polypeptide expression. Various methods can be used to measure expression. Preferred embodiments of the invention include PCR and Northern blotting for measuring RIP60 mRNA expression, and monoclonal or polyclonal antisera to RIP60 as reagents to measure RIP60 polypeptide expression. In certain embodiments, test samples are biopsy samples, and biological fluids such as blood. The method involves measuring a test level of RIP60 expression in a test sample and comparing the test level of RIP60 expression to a control.

Each of the limitations of the invention can encompass various embodiments of the invention. It is therefore anticipated that each of the limitations of the invention involving any one element or combinations of elements can be included in each aspect of the invention.

Sequence Listing

SEQ ID NO:1 is the nucleotide sequence of human RIP60 cDNA.
SEQ ID NO:2 is the amino acid sequence of human RIP60 polypeptide.
SEQ ID NO:3 is the nucleotide sequence of the Z2 domain of the human RIP60.
SEQ ID NO:4 is the amino acid sequence of the Z2 domain of the human RIP60.
SEQ ID NO:5 is the nucleotide sequence of the proline rich region of human RIP60.
SEQ ID NO:6 is the amino acid sequence of the proline rich region of human RIP60.
SEQ ID NO:7 is the nucleotide sequence of the primer p512.
SEQ ID NO:8 is the nucleotide sequence of the primer p520.
SEQ ID NO:9 is the nucleotide sequence of the primer p521.
SEQ ID NO:10 is the nucleotide sequence of the primer OCH7.
SEQ ID NO:11 is the nucleotide sequence of the primer OCH8.
SEQ ID NO:12 is the nucleotide sequence of the primer OCH13.
SEQ ID NO:13 is the nucleotide sequence of the primer OCH14.
SEQ ID NO:14 is the nucleotide sequence of the primer OCH35.
SEQ ID NO:15 is the nucleotide sequence of the primer OCH36.
SEQ ID NO:16 is the nucleotide sequence of the primer OCH37.
SEQ ID NO:17 is the nucleotide sequence of the primer OCH38.
SEQ ID NO:18 is the nucleotide sequence of the primer OCH39.
SEQ ID NO:19 is the nucleotide sequence of the primer OCH40.
SEQ ID NO:20 is the nucleotide sequence of the primer RIP1.
SEQ ID NO:21 is the nucleotide sequence of the primer RIP2.
SEQ ID NO:22 is the nucleotide sequence of the primer RIP3.
SEQ ID NO:23 is the nucleotide sequence of the primer RIP4.
SEQ ID NO:24 is the nucleotide sequence of the primer RIP5.
SEQ ID NO:25 is the nucleotide sequence of the primer RIP6.
SEQ ID NO:26 is the nucleotide sequence of the primer RIP7.
SEQ ID NO:27 is the nucleotide sequence of the primer RIP8.
SEQ ID NO:28 is the nucleotide sequence of the primer RIP9.
SEQ ID NO:29 is the nucleotide sequence of the primer RIP10.
SEQ ID NO:30 is the amino acid sequence of a tryptic fragment from RIP60.
SEQ ID NO:31 is the amino acid sequence of a tryptic fragment from RIP60.
SEQ ID NO:32 is the amino acid sequence of RIP60 zinc finger 1.
SEQ ID NO 33 is the amino acid sequence of RIP60 zinc finger 2.
SEQ ID NO:34 is the amino acid sequence of RIP60 zinc finger 3.
SEQ ID NO:35 is the amino acid sequence of RIP60 zinc finger 4.
SEQ ID NO:36 is the amino acid sequence of RIP60 zinc finger 5.
SEQ ID NO:37 is the amino acid sequence of RIP60 zinc finger 6.
SEQ ID NO:38 is the amino acid sequence of RIP60 zinc finger 7.
SEQ ID NO:39 is the amino acid sequence of RIP60 zinc finger 8.
SEQ ID NO:40 is the amino acid sequence of RIP60 zinc finger 9.
SEQ ID NO:41 is the amino acid sequence of RIP60 zinc finger 10.
SEQ ID NO:42 is the amino acid sequence of RIP60 zinc finger 11.
SEQ ID NO:43 is the amino acid sequence of RIP60 zinc finger 12.
SEQ ID NO:44 is the amino acid sequence of RIP60 zinc finger 13.
SEQ ID NO:45 is the amino acid sequence of RIP60 zinc finger 14.
SEQ ID NO:46 is the amino acid sequence of RIP60 zinc finger 15.
SEQ ID NO:47 is the amino acid consensus sequence for RIP60 zinc fingers.
SEQ ID NO:48 is the nucleotide sequence of the Z1 domain of RIP60.
SEQ ID NO:49 is the amino acid sequence of the Z1 domain of RIP60.
SEQ ID NO:50 is the nucleotide sequence of the Z2 and the PRR domain of RIP60.
SEQ ID NO:51 is the amino acid sequence of the Z2 and the PRR domain of RIP60.
SEQ ID NO:52 is the nucleotide sequence of a molecule which Z2 binds.
SEQ ID NO:53 is the nucleotide sequence of a molecule which Z2 binds.
SEQ ID NO:54 is the nucleotide sequence of a molecule which Z2 binds.
SEQ ID NO:55 is the nucleotide sequence of a molecule which Z2 binds.

SEQ ID NO:56 is the nucleotide sequence of a molecule which Z2 binds.
SEQ ID NO:57 is the nucleotide sequence of a molecule which Z2 binds.
SEQ ID NO:58 is the nucleotide sequence of a molecule which Z2 binds.
SEQ ID NO:59 is the nucleotide sequence of a molecule which Z2 binds.
SEQ ID NO:60 is the nucleotide sequence of a molecule which Z2 binds.
SEQ ID NO:61 is the nucleotide sequence of a molecule which Z2 binds.
SEQ ID NO:62 is the nucleotide sequence of a molecule which Z2 binds.
SEQ ID NO:63 is the nucleotide sequence of a molecule which Z2 binds.
SEQ ID NO:64 is the nucleotide sequence of a molecule which Z2 binds.
SEQ ID NO:65 is the nucleotide sequence of a molecule which Z2 binds.
SEQ ID NO:66 is the nucleotide sequence of a molecule which Z2 binds.
SEQ ID NO:67 is the nucleotide sequence of the DSR site.
SEQ ID NO:68 is the amino acid sequence of the proline rich region of RIP60 and adjacent regions.

DETAILED DESCRIPTION OF THE DRAWINGS

FIG. 1 is a schematic diagram depicting nucleic acid delivery to a cell via a modular polypeptide. In this example, the modular polypeptide is comprised of a nucleic acid binding domain, namely the Z2 DNA binding domain (DBD), and a cell recognition domain (CRD). As shown, the nucleic acid to be transferred is complexed by the DBD and the CRD is contacting a moiety on the target cell surface. In this instance, the nucleic acid delivery complex along with the cell surface receptor would be internalized e.g., via endocytosis.

Figure 2:
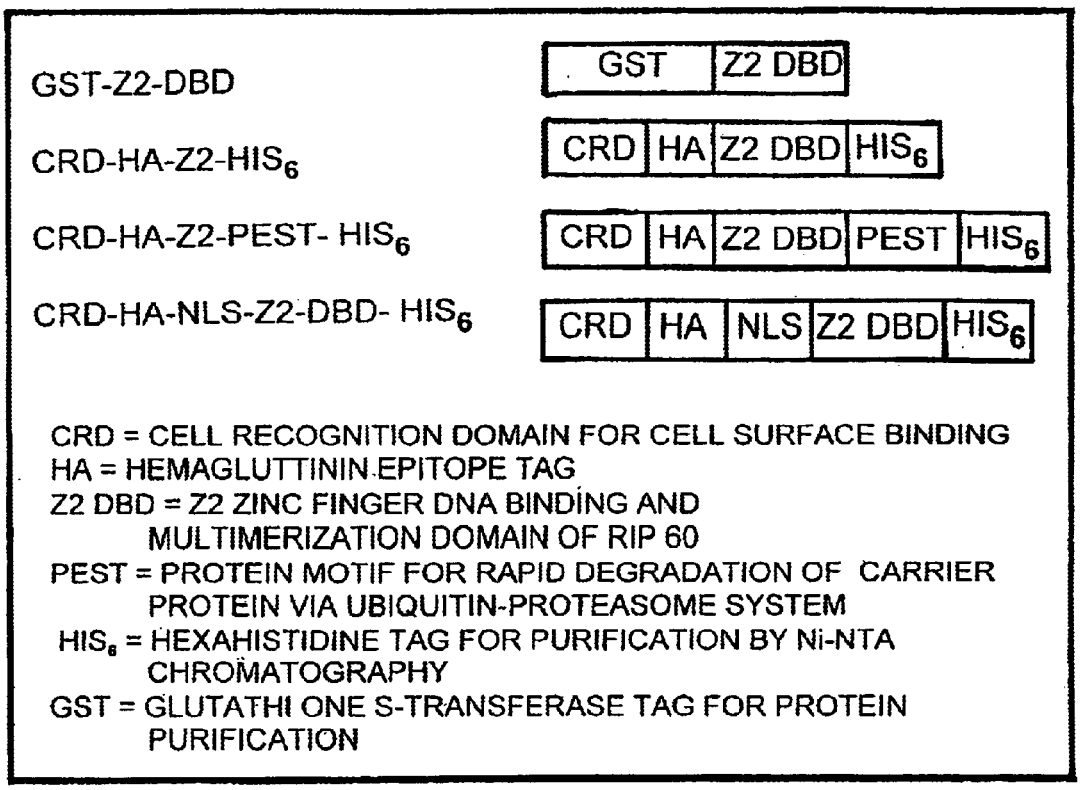

FIG. 2 illustrates examples of modular polypeptides which can be used for nucleic acid transfer. As shown, various combinations of functional domains can be used in any order.

Figure 3:
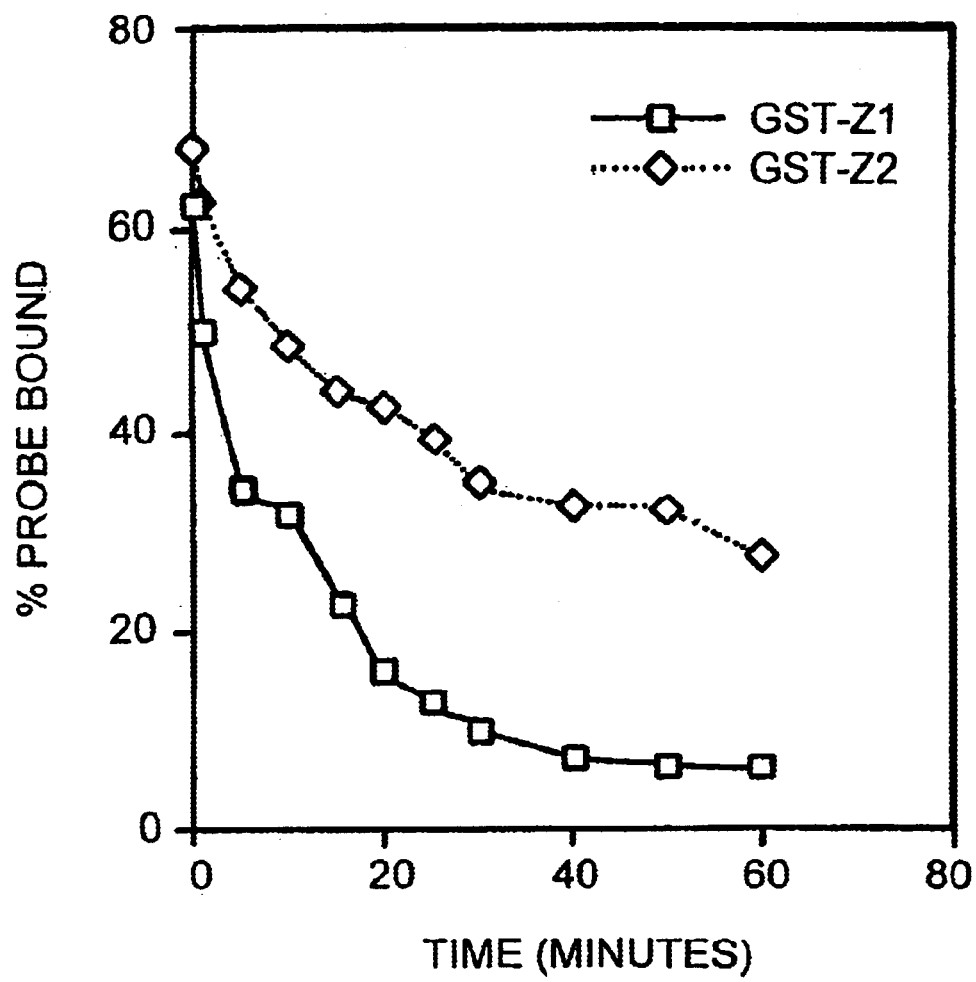
Figure 4:
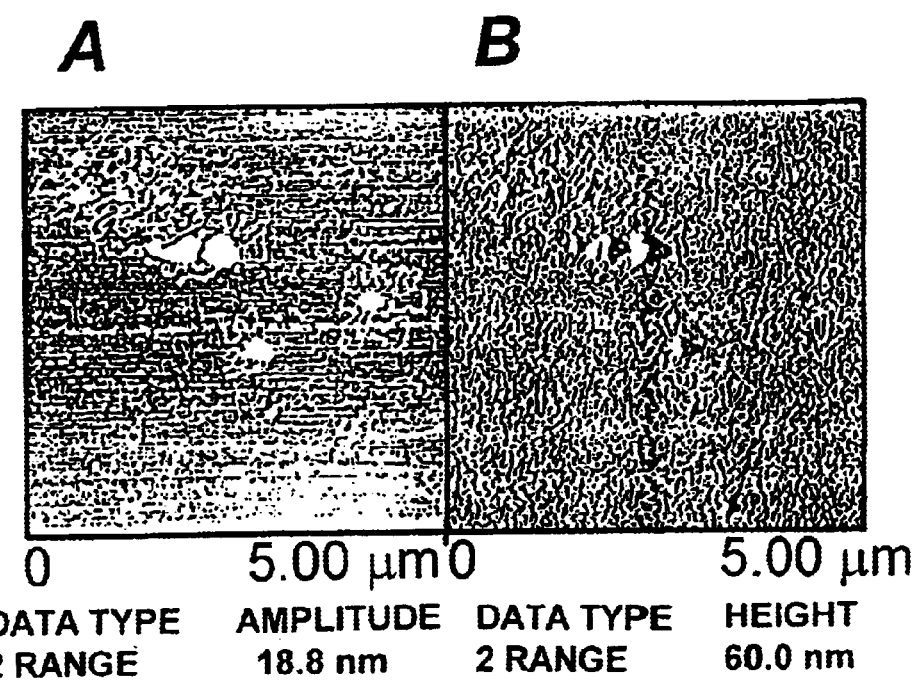

FIG. 3 is a graph of the percent specific probe bound to either GST-Z1 or GST-Z2 as a function of time after the addition of unlabeled probe. FIG. 4 (Panel A) is an atomic force microscopy image of uncomplexed BAC269 DNA. FIG. 4 (Panel B) is an atomic force microscopy image of BAC269 DNA complexed to GST-Z2.

Figure 5:
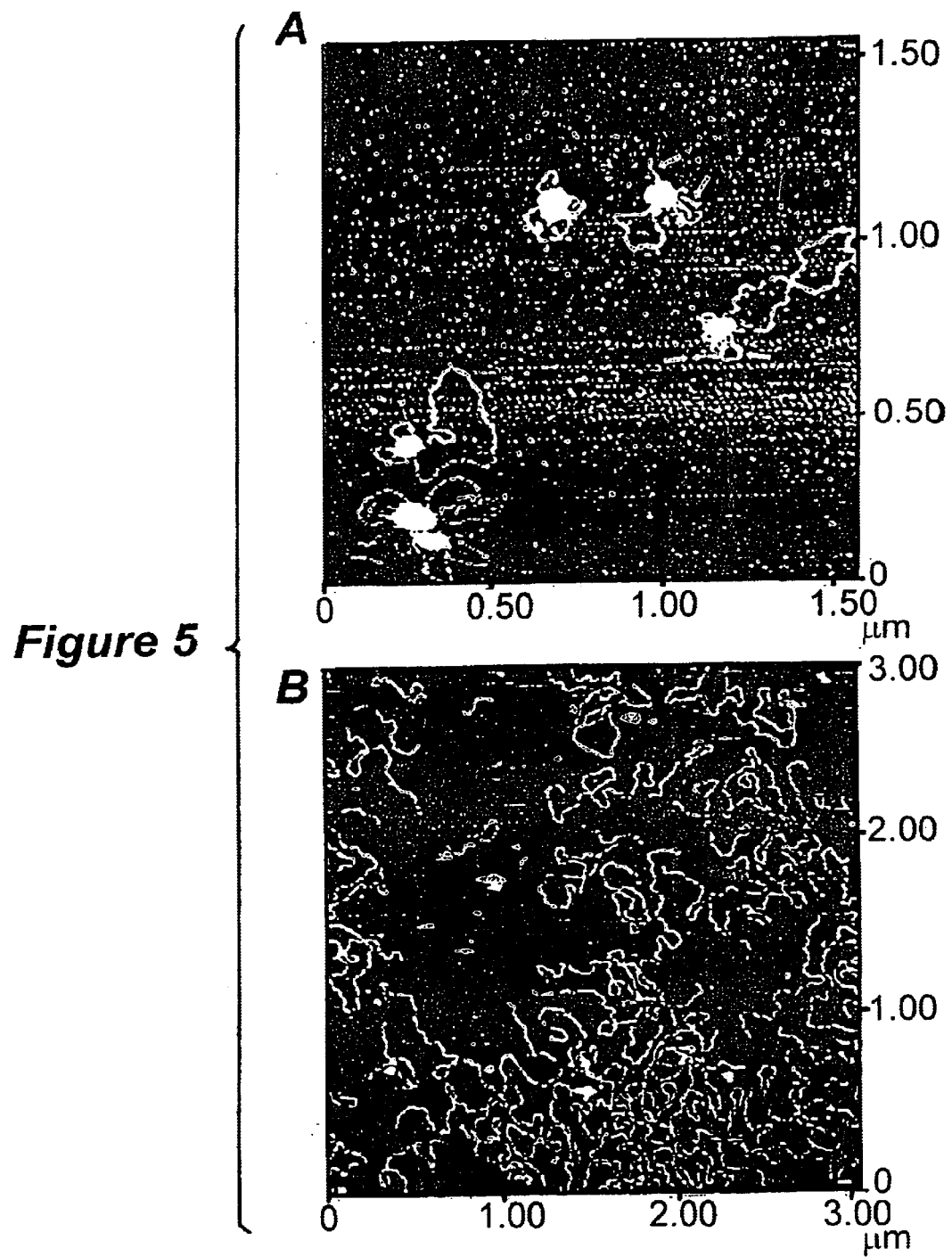

FIG. 5 (Panel A) is an atomic force microscopy image of DNA looping between the USR and the DSR by GST-Z2. Free ends of pCH127 protrude from the loop complex. FIG. 5 (Panel A) is an atomic force microscopy image of DNA containing both the USR and the DSR following incubation with GST-Z2ΔP. Looping between the USR and DSR is not observed in the absence of the PRR.

Figure 6:
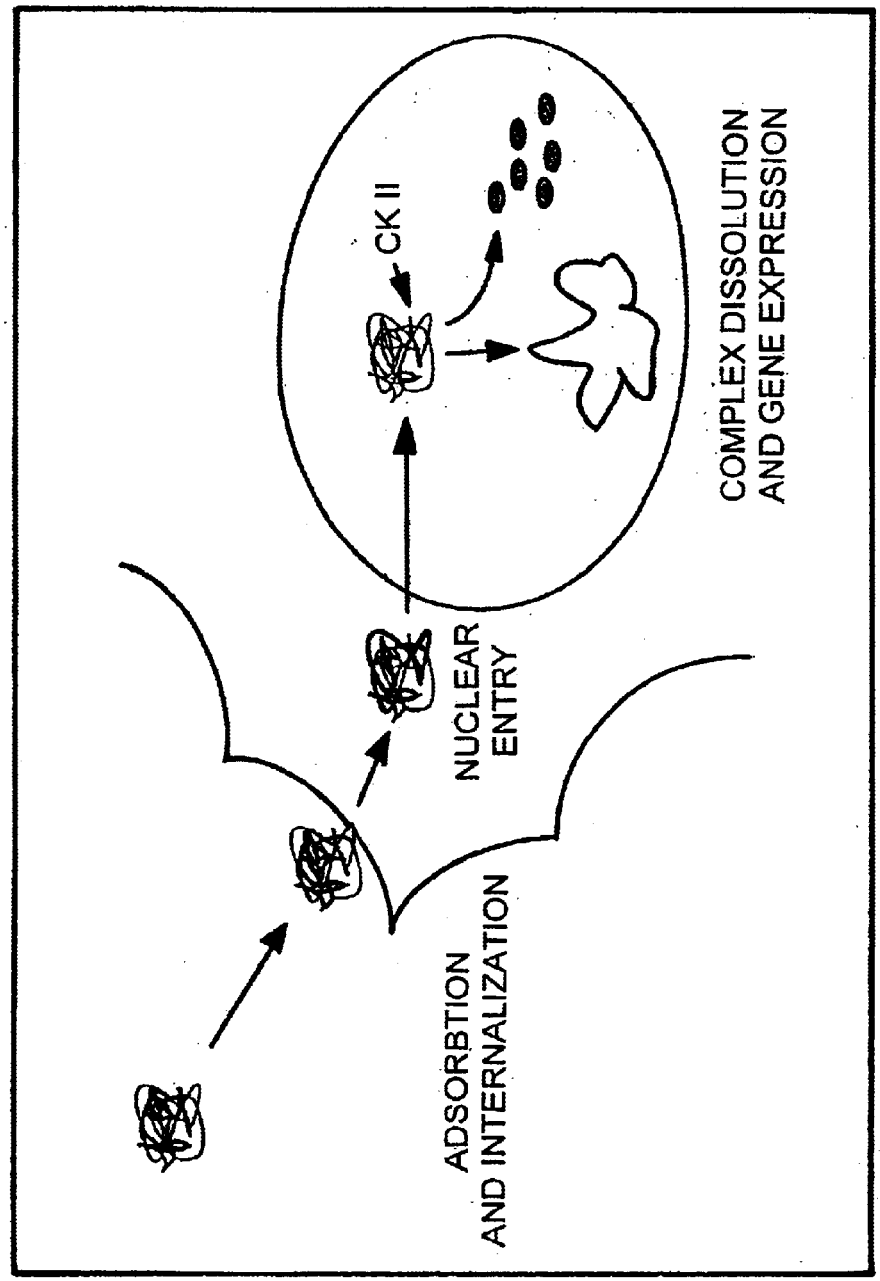

FIG. 6 is a schematic diagram depicting a model of phosphorylation of Z2-PRR by casein kinase II in gene delivery. Protein-DNA complexes (denoted by a ball of string) may be adsorbed to the cell surface, internalized, and shuttled to the nucleus. Upon nuclear entry, phosphorylation of the SAAE casein kinase II site in the proline-rich region of RIP60 or its derivatives by DNA, thereby facilitating the release of the DNA for transcription and other steps in gene expression.

DETAILED DESCRIPTION OF THE INVENTION

The invention relates to a nucleic acid delivery complex consisting of a modular polypeptide of varying composition, that binds and condenses large nucleic acids and then associates with the cell surface by simple absorption, or through one or more specific cell recognition domains. An illustrative example of a method of the invention is shown in FIG. 1. The complex may be actively engulfed or passively transported in the cell, at which point the delivered nucleic acid can be repaired if necessary, transcribed, replicated, or even recombined with other cellular nucleic acids.

The methods and products of the invention may be used for a variety of in vitro and in vivo purposes. The method is rapid, simple, inexpensive, and efficient. Studies indicate the method is not cytotoxic, unlike many prior art transfection techniques. The in vitro transfection of nucleic acids into cells commonly used in research laboratories which are generally cumbersome, expensive, inefficient and time-consuming can be replaced by the simple, efficient and inexpensive method of the invention. As a result of the broad flexibility of the methods, the invention can be used in numerous applications such as gene delivery in vitro, ex vivo and in vivo in animals or other organisms.

The invention in one aspect relates to products and methods for delivering nucleic acids of at least 50 kilobases (kb) in size to cells in vitro and in vivo. In accordance with the invention, the products and methods rely on the use of a nucleic acid delivery complex in the form of a multifunctional modular polypeptide. The modular polypeptide of the invention contains a nucleic acid binding domain and a nucleic acid condensation domain. As used herein, the terms "condensation domain" and "nucleic acid condensation domain" are used interchangeably. In addition to the nucleic acid binding domain and the condensation domain, the modular polypeptide can contain multiple functional entities, including but not limited to cell recognition domains, protein transduction domains, protein degradation domains, intracellular trafficking domains, protein interaction domains, protein purification domains and epitope domains.

Illustrative examples of modular polypeptides for the transduction of nucleic acids into cells are shown in FIG. 2. In these examples, the functional elements include a joint nucleic acid binding and condensation domain in the form of the Z2 zinc finger DNA binding and multimerization domain of RIP60, a cell recognition domain, a protein transduction domain, an epitope domain for protein tracking, and a protein purification domain. It is important to note that this approach allows one to organize these and other protein domains in a variety of configurations in order to optimize delivery of nucleic acids to specific cell types or tissues.

The nucleic acid binding domain is a domain which recognizes and binds nucleic acids. The nucleic acid binding domain of the invention can be any nucleic acid binding domain including but not limited to zinc finger domains, basic helix-loop-helix domains, and native or modified antibodies or fragments thereof. In a preferred embodiment, the nucleic acid binding domain is a zinc finger domain. Antibodies or fragments thereof may be modified such that the Fc portion is replaced with other domains including a protein interaction domain which can function as a condensation domain. In one embodiment of the invention, the nucleic acid binding domain recognizes and binds nucleic acids in a sequence independent manner. In another embodiment, the nucleic acid binding domain recognizes and binds nucleic acids in regions which are enriched in adenosine and thymidine nucleotides (e.g., ATT-rich sequences).

The modular polypeptide of the invention is also able to condense large nucleic acid fragments via a nucleic acid condensation domain. As used herein, the term condensation refers to compaction or reduction in size of a substance. Thus, a nucleic acid condensation domain is a domain which is able to compact or reduce the size of a nucleic acid molecule. Preferably, the nucleic acid molecule is greater than 50 kb in length. The nucleic acid condensation domain of the invention may be a protein multimerization domain. A multimerization domain is a domain which effects the association of two or more monomers of a given type. For example. A multimerization domain can effect the formation of a multimer consisting of 2, 3, 4, 5, 10, 20, 50, 100 or more monomers of, for example, the proline rich region of RIP60. The multimerization domain may also induce the formation of protein complexes consisting of different monomer subunits. As an example, the proline rich region of RIP60 may interact with one or more non-RIP60 polypeptides. The condensation domain can also include but is not limited to proline-rich regions, homeodomains, zinc finger domains and paired amphipathic helices. The nucleic acid condensation domain may be a protein interaction domain, such as a proline rich region. In preferred embodiments, the nucleic acid condensation domain is the Z2 domain of RIP60. In this latter embodiment, the Z2 domain may also function as the nucleic acid binding domain. In more preferred embodiments, the condensation domain is the proline rich region of RIP60, the amino terminus of which is incorporated into the Z2 region of RIP60. The proline rich region of RIP60 consists of three polyproline helices and a casein kinase II phosphorylation site.

Although not intending to be bound by any particular theory, it is postulated that the phosphorylation site functions to control the multimerization of the proline rich region and the ability of adjacent protein domains (such as the Z2 domain) to bind nucleic acid. As illustrated in FIG. 6, in an unphosphorylated form, the proline rich region, in association with a DNA binding domain, is capable of looping DNA. However, once the proline rich region has been phosphorylated, for example upon entry into the cell, the DNA dissociates from the protein complex, possibly as a consequence of a disruption of protein multimers. The DNA is then free to enter the nucleus and can be acted upon by transcriptional machinery, for example.

In some embodiments of the invention, the nucleic acid binding and condensation domains are distinct entities which can be fused together to form the common element of the modular polypeptide. For example, a zinc finger DNA binding domain can be fused to a proline rich region which is capable of multimerization. Examples of such nucleic acid binding domains which would be useful in the invention are the Z1, Z2, Z2ΔP and Z3 domains of RIP60. As used herein, the Z2ΔP domain consists of the zinc fingers 6, 7 and 8 but is lacking the amino terminus of the proline rich domain. As such, this domain is capable of nucleic acid binding but is not capable of significant multimerization. In still other variations, the Z1 or Z3 domains of RIP60 can be used as the nucleic acid binding domain. The Z1 domain is lacking any region of the proline rich region and thus, like Z2ΔP, is not capable of multimerization to any significant degree. Z3 on the other hand does contain the carboxy terminus of the proline rich region and is capable of some multimerization activity, albeit to a lesser extent than Z2.

In an important embodiment, the nucleic acid binding and condensation domains are derived from the Z2 domain of the polydactyl zinc finger RIP60 protein. Since the Z2 domain consists of zinc fingers 6, 7 and 8 as well as a region of the proline rich region of RIP60, it is capable of both binding to nucleic acids and multimerization, and thus can effectively condense large nucleic acids.

In another important embodiment, the Z1, Z2, Z2ΔP, Z3 or Z3ΔP domain of RIP60 can be used as the nucleic acid binding domain and the proline rich region of RIP60, in whole or in part, can be used as the condensation domain. In a preferred embodiment, the Z2 domain of RIP60 is the nucleic acid binding domain. In another embodiment, the Z2 domain and the proline rich region are used as the nucleic acid binding domain and the nucleic acid condensation domain.

According to one aspect of the invention, nucleic acid molecules are looped onto the nucleic acid binding and condensation domains. The nucleic acid binding domain contacts the nucleic acid while the condensation domains are able to self-interact. As a result, the condensation domains function as scaffolding for the multiple nucleic acid loops which are formed. The ability of the condensation domain to multimerize with itself (via protein-protein interaction domains) allows the compaction of large nucleic acids and thereby facilitates the uptake of the nucleic acid delivery complex into a variety of cell types. This is in contrast to other nucleic acid binding moieties such as polylysine that do not multimerize via protein-protein interactions, and thus do not compact such large pieces of DNA. Preferably, the condensation domain also contains a consensus target sequence for an intracellular kinase (i.e., a phosphorylation site). More preferably, the phosphorylation site is positioned such that it weakens and/or precludes multimerization once phosphorylated. An example of this is the casein kinase II phosphorylation site located in the proline rich region of RIP60 between the first and second polyproline helices of this domain.

The ability of a putative nucleic acid binding and condensation domain to function according the invention can be assessed using atomic force microscopy as described in detail in the Examples. Briefly, the putative domain is incubated with a nucleic acid molecule of 50 kb or greater and the resultant complex is observed using atomic force microscopy. A putative domain that interacts with a nucleic acid molecule to produce from a large contiguous circular or linear nucleic acid mass a compacted nucleic acid associated with the domain is a nucleic acid binding/condensation domain of the invention.

In one embodiment, the invention is the first instance of a multifunctional modular polypeptide which is able to bind and condense nucleic acids in manner which is relatively independent of sequence. It was discovered according to the invention that while the full length RIP60 polypeptide (i.e., SEQ ID NO:2) recognizes and binds sequences within the oriβ site of the dhfr gene (namely, the DSR and USR sequences), the Z2 domain exhibits a more relaxed binding preference. The Z2 domain has been shown to interact with all nucleic acids, although it prefers to bind nucleic acids which contain ATT, TAA and TTT stretches. Since these triplet motifs are common in the genome, with each occurring on average once every 64 nucleotides, it is expected that a nucleic acid which is 50 kb in length will have more than 700 of each binding site. As a result, a nucleic acid molecule to be complexed with the Z2 domain would not require any modification prior to complexing in order to be recognized by the Z2 domain. Thus Z2 provides an added benefit over other previously documented nucleic acid binding domains such as the GAL4 DNA binding domain which binds specifically to an extended target sequence of roughly 17 bases in length.

The invention relies on the discovery that large nucleic acids on the order of 200 kb can be bound and condensed by the Z2 DNA binding and multimerization domain of RIP60.

Using atomic force microscopy (AFM), it was discovered that a recombinant protein containing a GST purification tag fused to the Z2 DNA binding domain of RIP60 was able to condense DNA ranging in size from greater than 4 kb and surprisingly, even DNA greater than 50 kb and even 200 kb were condensed. An AFM image showing GST-Z2 binding as multimers to DNA is provided as an illustrative example in FIGS. 4 and 5. As described in the Examples, GST-Z2 lacking the proline rich region (i.e., GST-Z2ΔP) is capable of binding nucleic acids but is unable to induce multimers and thus is not capable of condensing the same DNA (FIG. 5).

Supercoiled, linear and circular DNA from a wide variety of sources can be bound, condensed and thereby delivered to cells using the Z2 domain. Moreover, since zinc finger motifs bind RNA/DNA hybrids and RNA in addition to DNA, zinc finger DNA binding domains of proteins like RIP60 can be used to deliver multiple, various nucleic acids. Many other zinc finger motifs can be identified through databases on the Internet such as GenBank and through the published literature. Many of these zinc finger motifs although they have been sequenced, have not been characterized. Any of these zinc finger motifs can be screened, alone or in combination with a condensation domain such as the proline rich region of RIP60, for the ability to bind and condense DNA greater in size than 50 kb.

One important aspect of the invention is its broad flexibility since both the modular polypeptide and the nucleic acid to be delivered can be endowed with a wide variety of properties. According to the invention, the modular polypeptide can be engineered to contain multiple functional entities, including cell recognition domains, protein transduction domains, protein degradation domains, intracellular trafficking domains, protein interaction domains, protein purification domains and epitopes. The modular polypeptide may contain one, two, three, four, five, six or seven or more of these domains in any combination and order specific to the practice of the invention. For example, the inclusion of a purification domain and a cell recognition domain would allow isolation and subsequent targeting of the polypeptide to a particular cell type. The modular polypeptide may also include several copies of the same type of domain.

The terms "modular polypeptide", "recombinant modular polypeptide", "multidomain polypeptide", "recombinant multidomain polypeptide", "fusion protein", "recombinant fusion protein", and "recombinant protein" may be used herein interchangeably, and as used throughout the present application and claims refer to a multifunctional polypeptide which binds and condenses nucleic acids in excess of 50 kb. In one aspect, the modular polypeptide is encoded by a single nucleic acid molecule. The modular polypeptide may also be encoded by more than one recombinant nucleic acid molecule. The polypeptides produced by the more than one recombinant nucleic acid molecule can then be assembled to produce the modular polypeptide.

As used herein, a cell recognition domain refers to any moiety which directly or indirectly associates with the extracellular surface of a cell and which can be used to specifically target the modular polypeptide to a particular cell type or tissue. A moiety that directly associates with the extracellular surface of a cell is one that contacts a cell surface molecule. A moiety that indirectly associates with the extracellular surface of a cell is one that contacts one or more moieties which in turn contacts a cell surface molecule. The cell recognition domain can be modified in order to target nucleic acid delivery to specific cell types. Cell recognition domains include but are not limited to cell surface receptors, receptor ligands, antibodies or fragments thereof, extracellular matrix binding peptides, carbohydrate moieties, lectins or other ligands for specific cell surface molecules. One or more of these can be incorporated within, conjugated to, or bound by the recombinant protein in order to target the nucleic acid to specific cell types. The specific cell recognition domain selected will depend on the type of cell to be targeted. One of ordinary skill in the art can easily identify a desired cell recognition domain by reviewing literature to determine what molecules bind to a particular cell type.

Protein transduction domains are protein domains which contact the extracellular surface of a cell and facilitate the nonspecific delivery of proteins into cells. Examples of protein transduction domains include but are not limited to HIV tat protein, and herpesvirus protein VP22.

Intracellular protein targeting domains are domains which specifically facilitate the transport of a protein or other moiety to a particular compartment or region within a cell. Intracellular protein targeting domains can be incorporated into the modular polypeptide of the invention to direct or release the nucleic acid from specific subcellular compartments. A subset of intracellular protein targeting domains is the intracellular localization signals, an example of which is a nuclear localization sequence. A nuclear localization sequence is one which directs a polypeptide from the cytoplasm to the nuclear membrane and hence the nucleus. Another example of an intracellular protein targeting domain is an endosomal release domain. An endosomal release domain is a domain which stimulates the release of endosome contents prior to endosome fusion with lysosomes. The examples listed herein are illustrative and are not intended to limit the range of intracellular protein targeting domains which can be incorporated into the modular polypeptide. Other intracellular protein targeting domains well known to those skilled in the art can also be used.

One or more protein interaction domains or other binding sequences can be incorporated into the modular polypeptide in order to noncovalently attach other cargo such as peptides, proteins, hormones, hormone receptors, signal transduction proteins and small molecules to the complex. In this latter variation, through the association with extracellular or intracellular moieties, the protein interaction domain can be used for cell targeting or intracellular targeting of the nucleic acid complex. The protein interaction domain in some embodiments can also be a proline rich domain or region such as that found in RIP60 protein.

In some embodiments, protein purification domains can be incorporated into the modular polypeptide. A protein purification domain as used herein is a compound preferably an amino acid sequence which when present in the modular polypeptide can be used to isolate or purify the modular polypeptide by interacting with a binding partner which may in turn be attached to a support. Any compound having a binding partner which forms a strong enough binding interaction to withstand separation procedures can be used as a protein purification domain. Suitable protein purification domains are well known in the art and include, but are not limited to, a glutathione-S-transferase (GST) tag, a hexahistidine or polyhistidine tag, a Protein A tag, a biotin tag, a chitin tag, and a maltose binding protein. One or more of these domains may be incorporated into the modular polypeptide of the invention. The determination of which purification domain to use depends on the specific modular polypeptide used, the binding partner, etc. Such a determination would be apparent to one of ordinary skill in the art. A procedure for producing and purifying fusion proteins is described in the Examples.

Epitope domains can be included in the modular polypeptide in order to track adsorption of the complex to the cell surface, entry of the protein into the cell, and metabolism or modification of the internalized protein. Suitable epitope domains include a hemaglutinnin (HA) tag, a FLAG tag, a V5 tag, a myc tag, and a T7 sequence. The determination of which epitope domain or combination of epitope domains to use for a particular purpose depends on the experimental conditions and will be apparent to an ordinarily skilled artisan.

Protein degradation domains such as proline-glutamic acid-serine-threonine (PEST) sequences can be incorporated into the recombinant protein in order to induce degradation of the protein upon cellular entry, thereby obviating untoward effects on cellular metabolism due to the delivery protein. Other protein degradation sequences known to those skilled in the art can also be used. For instance, by manipulating phosphorylation sites on specific proteins, it is well known that it is possible to prevent degradation or to mark the protein for degradation. Certain proteins such as CDD6 can be phosphorylated to cause degradation once the protein is in an intracellular environment.

According to one embodiment of the invention, the modular polypeptide can complex with a nucleic acid in order to deliver the nucleic acid to a cell. As used herein, the term complex refers to the physical association or connection between two distinct, separable moieties. As an illustrative example, the stable interaction between a nucleic acid and a polypeptide such as the modular polypeptide of the invention is considered a complex. Similarly, it can be said that a nucleic acid is complexed with a polypeptide. A complex can contain more than two moieties and the nature of these moieties, for instance, can be but is not limited to nucleic acid, peptide and carbohydrate when a carbohydrate is included in the modular polypeptide.

As used herein, a nucleic acid refers to DNA, RNA and DNA/RNA hybrid molecules composed of native and/or modified nucleotides. In some embodiments of the invention, the nucleic acid is a sense DNA or RNA molecule, in a single or double stranded form depending on the intended application of the invention. In other embodiments, the nucleic acid is an antisense DNA or RNA molecule. In yet other embodiments, the nucleic acid is a unmodified fragment of chromosomal DNA. In yet a further embodiment, the nucleic acid can be a bacterial artificial chromosome (BAC) or a yeast artificial chromosome (YAC). In a preferred embodiment the nucleic acid is a unmodified fragment of human chromosomal DNA. As used herein, an unmodified fragment of DNA is a fragment of DNA which has not undergone sequence changes in vivo or in vitro for the purpose of introducing an exogenous DNA sequence. Thus an unmodified fragment of DNA has the same sequence as when it was originally harvested from a cell, tissue or subject. The invention embraces the delivery of nucleic acids which are equal to or greater than 50 kb, 75 kb, 100 kb, 125 kb, 150 kb and 200 kb in length.

The nucleic acid once it is delivered to the cell can provide a variety of functions such as promoting or inhibiting the synthesis of additional nucleic acids, such as RNA molecules or antisense molecules, or polypeptide upon cell entry. The end result of the nucleic acid transfer may be to alter gene expression which in turn could influence cell growth, cell differentiation or cell death, depending on the nature and function of the encoded polypeptide(s) and the specific application. The nucleic acid may encode one or more native polypeptides which may be absent or defective due to mutation in the wild type gene. For example, the nucleic acid may comprise homologous sequences which facilitate its recombination with host cell sequences in order to repair damaged or mutant genes or to simply increase the number of copies of a normal gene such as might be desirable for tumor suppressor genes which are invariably inactivated in cancerous lesions. Examples of tumor suppressor genes include but are not limited to p53, Rb and WT-1. Other genetic mutations which can be targeted are well known in the art and include CF and MD mutations. In another embodiment, the nucleic acid may encode a polypeptide which acts to inactivate dominant negative proteins which result from mutation. As used herein, the term transduced nucleic acid is used interchangeably with delivered nucleic acid, transferred nucleic acid and nucleic acid to be delivered. Similarly the term transduction is meant to be used interchangeably with delivery, transfection and transfer.

According to one embodiment of the invention, the nucleic acid binding domain recognizes and binds nucleic acid in a sequence independent manner. It was discovered according to the invention that although the Z2 DNA binding domain tends to preferentially bind adenosine and thymidine rich regions of a nucleic acid, it is also capable, in some instances, of binding nucleic acids without preference for a particular sequence or composition (i.e., in a sequence independent manner). This discovery indicates that transduced nucleic acids do not require any modification, such as cloning or ligation with artificial consensus sequences, in order to be recognized and bound by the nucleic acid binding domain of the invention. As discussed in the Examples, the Z2 domain binds nucleic acids which contain ATT, TAA and TTT stretches.

The invention also embraces cell recognition domains and nucleic acid binding domains in the form of antibodies or fragments of antibodies. When used as cell recognition domains, the antibodies useful according to the invention recognize molecules on the extracellular surface of cells. When used as nucleic acid binding domains, the antibodies recognize nucleic acids. An example of antibodies that recognize nucleic acids are those produced in the autoimmune disorder systemic lupus erythematosus. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The nucleic acid delivery complex and its method of use are amenable to nucleic acid transduction in any type of cell including but not limited to animal, plant, insect, and other eukaryotic cells, in both in vitro and in vivo settings. In vitro, cells in suspension, or tissue or organ cultures can be used as targets for nucleic acid delivery. In another embodiment, prokaryotic cells can be targeted for nucleic acid delivery. When used in vivo the modular polypeptide can mimic the mechanism of viral entry without the use of viral proteins, capsids, or the generation of recombinant viruses. This inherently prevents the risk of viral infection within a subject. In vivo, the nucleic acids can be targeted to cells, tissue or organs as necessary.

The methods of the invention are also useful for the ex vivo gene transfer into cells. An example of an ex vivo gene therapy method is outlined in U.S. Pat. No. 5,399,346 and in exhibits submitted in the file history of that patent, all of which are publicly available documents. In general, ex vivo nucleic acid delivery involves introduction in vitro of a functional copy of a gene into a cell(s) of a subject which contains a defective or absent copy of the wild type gene, and returning the genetically engineered cell(s) to the subject. In some embodiments, the functional copy of the gene is under operable control of regulatory elements which permit expression of the gene in the genetically engineered cell(s). In still other embodiments, the gene is under the control of native regulatory elements as described below.

The methods of the invention can be used for genetic screening based on phenotype or complementation assay following the introduction of large fragments of nucleic acid into a cell or organism.

The methods of the invention are also useful for introducing entire native genetic loci of one or more polypeptides into cells. This aspect of the invention is useful since the combined regulatory and structural elements for many human genes span more than 50 kb and in some cases more than 100 kb, 150 kb or 200 kb. The products and methods of the invention allow intact loci including locus control regions, enhancers, 5' flanking untranslated sequences, promoters, coding sequences, introns and 3' flanking untranslated sequences in their native organization to be transferred to cells. This should effectively function in a manner identical to the endogenous locus. In one embodiment any combination of two, three, four, five, six or more of these elements can be used. In a preferred embodiment the nucleic acid contains the minimal number of elements to mimic the expression pattern of the endogenous locus. In a more preferred embodiment, the nucleic acid is delivered to cells of a subject with one or more genetic mutations. Such genetic mutations are well known in the art and include mutations to tumor suppressor genes such as Rb, p53 and WT-1, as well as mutations to other genetic loci including but not limited to the ADA, CF and the MD gene loci. Previous prior art approaches have not been reported to effectively transfer large DNA molecules in excess of 50 kb.

The methods of the invention are also useful for testing whether the modular polypeptide may have a specific regulatory function upon cell entry. This could facilitate a screen for peptide sequences that permit introduction of selected reporter genes into specific tissues, cells, or intracellular locations. This method could be further adapted for introducing reporter genes to detect specific cellular defects associated with cancer or other diseases, or for introducing suicidal genes into diseased cells.

In yet another aspect, the invention provides pharmaceutical compositions which comprise pharmaceutically effective amounts of the nucleic acid delivery complex of the invention along with a pharmaceutically acceptable carrier. A pharmaceutically effective amount of the nucleic acid delivery complex is that amount which results in the delivery of a nucleic acid to a cell. An example of such an effective amount is that amount which is required to deliver a desired nucleic acid to a cell or a tissue. Kits comprising the foregoing pharmaceutical composition are also provided. Such kits also contain instructions for the use of the composition. In either or both of these latter aspects of the invention, a nucleic acid molecule may also be provided.

As used herein, a subject is a human, non-human primate, cow, horse, pig, sheep, goat, dog, cat or rodent. In all embodiments human RIP60 and human subjects are preferred, however given the teachings herein of human RIP60 nucleic acids and polypeptides, it would be routine to screen and clone RIP60 molecules from another species and use these in the methods and compositions of the present invention.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Other embodiments of the invention relate to the isolated nucleic acid molecules which encode the modular polypeptide variants envisioned in the invention, vectors containing these nucleic acid molecules and host cells for the propagation of these vectors.

The invention also relates to nucleic acid and polypeptides encoding the zinc finger protein RIP60. RIP60 is useful for a variety of in vitro and in vivo purposes described herein and in co-pending U.S. Patent Application, having common inventorship, entitled "RIP60 Nucleic Acid and Polypeptide Sequences and Uses Therefor" and filed concurrently herewith. The invention also involves in another aspect an isolated RIP60 polypeptide, the cDNA encoding this polypeptide, functional modifications and variants of the foregoing, useful fragments of the foregoing and binding partners of the foregoing. Thus, one aspect of the invention involves the cloning of a human cDNA, 2954 bp in size encoding RIP60, represented by SEQ ID NO:1. RIP60 was identified as a protein capable of interacting with the dhfr orip site and was named Replication Initiation Region Protein 60 kD. The human RIP60 polypeptide is predicted to be a 62 kD protein, believed to function in the regulation of cell growth via nucleic acid replication and transcription. Although not intending to be bound by any particular theory, it is possible that RIP60 is present or induces replication and/or transcriptional complexes, perhaps functioning to recognize nucleic acid sequences or stabilize the binding of such complexes on nucleic acids. The predicted amino acid sequence of the encoded human protein product is presented as SEQ ID NO:2. "RIP60 activity" intends a wide variety of activities and can include one or more of the following: DNA binding, protein multimerization and nucleic acid looping (as a result of DNA binding and protein multimerization). As used herein, protein multimerization refers to the ability of proteins to interact and thus form complexes with more than one monomer or unit. Full length RIP60 preferentially binds to DSR and USR sequences as described herein and such as those located in the orip site in the dhfr locus. Other RIP60 polypeptides such as the Z2 domain are less stringent in their DNA binding specificity and are capable of binding in a relatively sequence independent manner, although a preference for ATT, TAA and TTT rich sequences has been observed.

According to the invention, isolated RIP60 nucleic acid molecules are provided that include: (a) nucleic acid molecules which hybridize under stringent conditions to a molecule consisting of a nucleic acid of SEQ ID NO:1, SEQ ID NO:3, SEQ ID NO:5 or SEQ ID NO:50 and which code for a polypeptide with RIP60 activity, (b) deletions, additions and substitutions of (a) which code for a polypeptide having RIP60 activity, (c) nucleic acid molecules that differ from the nucleic acid molecules of (a) or (b) in codon sequence due to the degeneracy of the genetic code, and (d) complements of (a), (b) or (c). In some important embodiments, the polypeptide with RIP60 activity is a native RIP60 polypeptide.

Homologs and alleles of the RIP60 nucleic acids of the invention can be identified by conventional techniques. Thus, an aspect of the invention is those nucleic acid sequences which code for RIP60 polypeptides and which hybridize to a nucleic acid molecule consisting of the coding region of SEQ ID NO:1, SEQ ID NO:3, SEQ ID NO:5 or SEQ ID NO:50 under stringent conditions. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of RIP60 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity to SEQ ID NO:1, SEQ ID NO:3, SEQ ID NO:5 or SEQ ID NO:50, and/or at least 80% amino acid identity to SEQ ID NO:2, SEQ ID NO:4, SEQ ID NO:6 or SEQ ID NO:51. Preferably, homologs and alleles will share at least 85% nucleotide identity and/or at least 90% amino acid identity and, even more preferably, at least 90% nucleotide identity and/or at least 95% amino acid identity will be shared. In a most preferred embodiment, homologs and alleles will share at least 95% nucleotide identity and/or at least 99% amino acid identity. The homology can be calculated using various, publicly available software tools developed by NCBI (Bethesda, Md.) that can be obtained through the internet at the website of the NCBI/NIH. Exemplary tools include the BLAST system available at the website of the NCBI/NIH. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for RIP60 related genes, such as homologs and alleles of RIP60, a Southern blot may be performed using the foregoing conditions, together with a radioactive probe. After washing the membrane to which the DNA is finally transferred, the membrane can be placed against X-ray film or a phosphoimager plate to detect the radioactive signal.

Given the teachings herein of a full-length human RIP60 cDNA clone, other mammalian sequences such as the mouse cDNA clone corresponding to the murine RIP60 gene can be isolated from a cDNA library prepared from one or more of the tissues in which RIP60 expression is abundant, using standard colony hybridization techniques. Accordingly, RIP60 nucleic acids and polypeptides and fragments thereof from species other than humans can also be used in the methods and compositions of the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating RIP60 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1, SEQ ID NO:3, SEQ ID NO:5 or SEQ ID NO:50 or complements thereof. A unique fragment is one that is a 'signature' for the larger nucleic acid. For example, the unique fragment is long enough to assure that its precise sequence is not found in molecules within the human genome outside of the RIP60 nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank and EMBL database accession numbers listed in Table 1 (see below) or other previously published sequences as of the priority filing date of this application.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of RIP60 polypeptides, useful, for example, in the preparation of antibodies, immunoassays or therapeutic applications. Unique fragments further can be used as antisense molecules to inhibit the expression of RIP60 nucleic acids and polypeptides respectively.

As will be recognized by those skilled in the art, the size of the unique fragment will depend upon its conservancy in the genetic code. Thus, some regions of SEQ ID NO:1, SEQ ID NO:3, SEQ ID NO:5 or SEQ ID NO:50 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, provided the sequence is unique as described above. Taking into account the exclusion described above, virtually any segment of the region of SEQ ID NO:1 beginning at nucleotide 1 and ending at nucleotide 2954, or SEQ ID NO:3 beginning at nucleotide 1 and ending at nucleotide 378, or SEQ ID NO:5 beginning at nucleotide 1 and ending at nucleotide 177, or SEQ ID NO:50 beginning at nucleotide 1 and ending at nucleotide 441, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

The invention also involves expression vectors coding for RIP60 proteins and fragments and variants thereof. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., 3-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for or conducive to the transcription of a nucleotide sequence which encodes a desired peptide and/or which are necessary for or conducive to the translation of the resulting transcript into the desired peptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (or RNA) encoding RIP60 polypeptide or fragment or variant thereof. The heterologous DNA is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710–4716, 1996). Still another preferred expression vector is an adenovirus, described by Stratford-Perricaudet, which is defective for E1 and E3 proteins (J. Clin. Invest. 90:626–630, 1992). The use of the adenovirus as an Adeno.P1A recombinant is disclosed by Warnier et al., in intradermal injection in mice for immunization against P1A (Int. J. Cancer, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described RIP60 cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). The invention also embraces host cells containing those expression vectors coding for RIP60 proteins and fragments and variants thereof. Virtually any cells, prokaryotic or eukaryotic, which can be transformed with heterologous DNA or RNA and which can be grown or maintained in culture, may be used in the practice of the invention. Especially useful are mammalian cells such as mouse, hamster, pig, goat, primate, etc. They may be of a wide variety of tissue types, and may also include primary cells and cell lines. Specific examples include dendritic cells, U293 cells, peripheral blood leukocytes, bone marrow stem cells and embryonic stem cells, mast cells, fibroblasts, oocytes and lymphocytes. Cell-free transcription systems also may be used in lieu of cells.

The invention also permits the construction of a RIP60 gene "knock-outs" in cells and in animals, providing materials for studying certain aspects of RIP60 activity.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, SEQ ID NO:3, SEQ ID NO:5 or SEQ ID NO:50 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nat. Med. 1(11):1116–1118, 1995). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439–457, 1994) and at which proteins are not expected to bind. Finally, although, SEQ ID NO:1 discloses a cDNA sequence, one of ordinary skill in the art may easily derive the genomic DNA corresponding to this sequence. Thus, the present invention also provides for antisense oligonucleotides which are complementary to a genomic DNA corresponding to SEQ ID NO:1, SEQ ID NO:3, SEQ ID NO:5 or SEQ ID NO:50. Similarly, antisense to allelic or homologous RIP60 cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acids encoding RIP60 polypeptides, together with pharmaceutically acceptable carriers. Antisense oligonucleotides may be administered as part of a pharmaceutical composition, for instance, when it is desirable to inhibit cell division. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient.

The invention also embraces expression vectors coding for RIP60 proteins and fragments (including unique fragments) and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E.coli, insect cells (using baculovirus expression vectors), yeast cells and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion protein. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40, pMAL (New England Biolabs, Beverly, Mass.) and pRIT5 (Pharmacia, Piscataway, N.J.) which fuse glutathione-S-transferase (GST), maltose E binding protein, or protein A, respectively, to the target recombinant protein. Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trc-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111–2118). Such alteration of nucleic acid sequences of the invention can be carried out by standard DNA synthesis techniques.

Examples of vectors for expression in yeast *S. cerevisiae* include pYepSec1 (Baldari, et al., (1987) EMBO 6:229–234), pMFa (Durjan and Herskowitz, (1982) Cell 30:933–943), pJRY88 (Schultz et al., (1987) Gene 54:113–123), pYES2 (Invitrogen Corporation, San Diego, Calif.), and picZ (InVitrogen Corp, San Diego, Calif.).

Alternatively, vectors can be expressed in insect cells using baculovirus expression vectors. Baculovirus vectors available for expression of protein in cultured insect cells (e.g., Sf9 cells) include the pAc series (Smith et al. (1983) Mol. Cell Biol. 3:2156–2165) and the pVL series (Lucklow and Summers (1989) Virology 170:31–39).

In yet another embodiment, vectors are expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187–195). The invention also provides isolated polypeptides (including whole proteins and partial proteins), encoded by the foregoing RIP60 nucleic acids, and including the polypeptides of SEQ ID NO:2, SEQ ID NO:4, SEQ ID NO:6 and SEQ ID NO:51 and unique fragments thereof. As used herein, a RIP60 polypeptide refers to a polypeptide having RIP60 activity. RIP60 activity as used herein refers to one or more of the following activities: DNA binding (e.g., to a DSR or USR sequence), protein multimerization, and/or DNA looping ability. Full length RIP60 polypeptide is capable of binding to the USR and DSR of the dhfr oriβ site and can form multimers via its proline rich region. RIP60 activity as used herein also encompasses binding of nucleic acids which are ATT-rich or T-rich, a property exhibited by the Z2 domain of RIP60. Preferably, the RIP60 polypeptide is a native RIP60 polypeptide. Such polypeptides are useful, for example, alone, in combination with other domains as the modular polypeptides of the invention, or as fusion proteins to transfer nucleic acids into a cell, to regulate cellular growth, differentiation and proliferation, to generate antibodies, as components of an immunoassay, or as a binding partner in a binding assay. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of a RIP60 polypeptide, in general, has the features and characteristics of unique fragments as discussed above in connection with nucleic acids as discussed above. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 567 amino acids long). Virtually any segment of SEQ ID NO:2, excluding the ones that share identity with it that is 9 or more amino acids in length will be unique. Similarly, unique fragments of SEQ ID NO:4, SEQ ID NO:6 and SEQ ID NO:51 are also provided.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof including other RIP60 polypeptides or other proline rich region containing polypeptides or fragments thereof. A subset of unique fragments will possess the ability to effect protein interaction and thus cause protein multimerization. One important activity is the ability to act as a signature for identifying the polypeptide. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is typically required. Preferably, the unique fragment is unique in humans, i.e., it is long enough to assure that its precise sequence is not found in molecules encoded by the human genome outside of RIP60 polypeptides including alleles.

The invention embraces variants of the RIP60 polypeptides described above. As used herein, a "variant" of a RIP60 polypeptide is a polypeptide which contains one or more modifications to the primary amino acid sequence of a RIP60 polypeptide. Modifications which create a RIP60 polypeptide variant are typically made to the nucleic acid which encodes the RIP60 polypeptide, and can include deletions, point mutations, truncations, amino acid substitutions and addition of amino acids or non-amino acid moieties to: 1) reduce or eliminate an activity of a RIP60 polypeptide; 2) enhance a property of a RIP60 polypeptide, such as protein stability in an expression system, DNA binding potential, and/or the stability of protein-protein binding; 3) provide a novel activity or property to a RIP60 polypeptide, such as addition of an antigenic epitope or addition of a detectable moiety; or 4) to provide equivalent or better binding to a RIP60 polypeptide receptor or other molecule (e.g., an anti-RIP60 antibody). Alternatively, modifications can be made directly to the polypeptide, such as by cleavage, addition of a linker molecule, addition of a detectable moiety, such as biotin, addition of a fatty acid, and the like or addition of other domains of the modular polypeptide of the invention. Modifications also embrace fusion proteins comprising all or part of the RIP60 amino acid sequence. One of skill in the art will be familiar with methods for predicting the effect on protein conformation of a change in protein sequence, and can thus "design" a variant RIP60 polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

Variants can include RIP60 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a RIP60 polypeptide by eliminating proteolysis by proteases in an expression system (e.g., dibasic amino acid residues in yeast expression systems in which KEX2 protease activity is present).

Mutations of a nucleic acid which encodes a RIP60 polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide. Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant RIP60 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a RIP60 gene or cDNA clone to enhance expression of the polypeptide.

The skilled artisan will realize that conservative amino acid substitutions may be made in RIP60 polypeptides to provide functionally equivalent variants of the foregoing polypeptides, i.e., the variants retain the functional capabilities of the RIP60 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the RIP60 polypeptides include conservative amino acid substitutions of SEQ ID NO:2, SEQ ID NO:4, SEQ ID NO:6 and SEQ ID NO:51. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of RIP60 polypeptides, i.e., variants of RIP60 polypeptides which retain the function of the natural RIP60 polypeptides (such as binding and multimerization on USR or DSR nucleic acid sequences), are contemplated by the invention. Conservative amino-acid substitutions in the amino acid sequence of RIP60 polypeptides to produce functionally equivalent variants of RIP60 polypeptides typically are made by alteration of a nucleic acid encoding RIP60 polypeptides (SEQ ID NO:1, SEQ ID NO:3, SEQ ID NO:5 and SEQ ID NO:51). Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488–492, 1985), or by chemical synthesis of a gene encoding a RIP60 polypeptide. The activity of functionally equivalent fragments of RIP60 polypeptides can be tested by cloning the gene encoding the altered RIP60 polypeptide into a bacterial or mammalian expression vector, introducing the vector into an appropriate host cell, expressing the altered RIP60 polypeptide, and testing for a functional capability of the RIP60 polypeptides as disclosed herein, e.g., testing for the ability of RIP60 to bind to and condense large i.e., greater than 50 kb nucleic acid sequences.

The invention as described herein has a number of uses, some of which are described elsewhere herein. First, the invention permits isolation of RIP60 nucleic acid molecules which code for a RIP60 polypeptide. As described above, nucleic acid isolation can be performed using hybridization under stringent conditions. A second use of the invention is the isolation of RIP60 polypeptides, using a variety of methodologies well-known to the skilled practitioner. The RIP60 polypeptide may be purified from cells which naturally produce it by chromatographic means or immunological recognition. Alternatively, an expression vector which incorporates a coding RIP60 nucleic acid molecule, such as SEQ ID NO:1 and perhaps preferably SEQ ID NO:3, SEQ ID NO:5 or SEQ ID NO:50, may be introduced into cells to cause production of the RIP60 polypeptide. In another method, mRNA transcripts may be microinjected or otherwise introduced into cells to cause production of the encoded polypeptide. Translation of RIP60 mRNA in cell-free extracts such as the reticulocyte lysate system also may be used to produce RIP60 polypeptides. Those skilled in the art also can readily follow known methods for isolating RIP60 polypeptides. These include, but are not limited to, immunochromatography, HPLC, size-exclusion chromatography, ion-exchange chromatography and immune-affinity chromatography.

The invention also embraces agents that bind to the RIP60 polypeptides. One category of such agents is isolated peptide binding agents which, for example, can be antibodies or fragments of antibodies ("binding polypeptides"), having the ability to selectively bind to RIP60 polypeptides. Antibodies include polyclonal and monoclonal antibodies and can be prepared according to conventional methodology. Such antibodies can be further manipulated to create chimeric or humanized antibodies as was discussed in greater detail above.

Thus, the invention provides a variety of polypeptides of varying size and type that bind specifically to RIP60 polypeptides, and complexes of both RIP60 polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries of peptides containing one or more amino acids also can be synthesized. Similarly, libraries of peptides and non-peptide synthetic moieties can be synthesized.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the RIP60 polypeptide or a complex of a RIP60 polypeptide and a binding partner. This process can be repeated through several cycles of reselection of phage that bind to the RIP60 polypeptide or complex. Repeated rounds lead to enrichment of phage bearing particular sequences. DNA sequence analysis can be performed to identify the sequences of the expressed polypeptides. The minimal linear portion of the sequence that binds to the RIP60 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the RIP60 polypeptides. Thus, the RIP60 polypeptides of the invention, or a fragment thereof, or complexes of RIP60 polypeptides and a binding partner can be used to screen peptide libraries, including phage display libraries, to identify and select peptide binding partners of the RIP60 polypeptides of the invention. Such molecules can be used, as described, for screening assays, for purification protocols, for interfering directly with the functioning of RIP60 polypeptides and for other purposes apparent to those of ordinary skill in the art. Such assays would be useful in identifying binding partners for RIP60 which are present in either or both replication or transcriptional machinery complexes.

A RIP60 polypeptide, or a fragment thereof, also can be used to isolate RIP60 native binding partners, according to one aspect of the invention. Isolation of binding partners may be performed according to well-known methods. For example, isolated RIP60 polypeptides can be attached to a substrate, and then a solution suspected of containing a RIP60 binding partner may be applied to the substrate. If the binding partner for RIP60 polypeptides is present in the solution, then it will bind to the substrate-bound RIP60 polypeptide. The binding partner then may be isolated. Other proteins capable of binding to RIP60 polypeptides may be similarly isolated using no more than routine experimentation.

An agent that binds RIP60 polypeptides, such as an antibody, may be conjugated to a detectable label. Conjugation of the agent to a detectable label facilitates, among other things, the use of such agents in diagnostic assays. A detectable label is a moiety, the presence of which can be ascertained directly or indirectly. Generally, detection of the label involves an emission of energy by the label. The label can be detected directly by its ability to emit and/or absorb light of a particular wavelength. A label can be detected indirectly by its ability to bind, recruit and, in some cases, cleave another moiety which itself may emit or absorb light of a particular wavelength. An example of indirect detection is the use of a first enzyme label which cleaves a substrate into visible products. The label may be of a chemical, peptide or nucleic acid nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin and enzyme tags such as horseradish peroxidase, β-galactosidase, etc.

The invention further provides efficient methods of identifying agents or lead compounds for agents active at the level of a RIP60 or RIP60 fragment dependent cellular function. Generally, the screening methods involve assaying for compounds which enhance RIP60 activity. Such methods are adaptable to automated, high throughput screening of compounds.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acids on the intracellular binding of RIP60 or RIP60 fragments to intracellular targets. The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a RIP60 polypeptide fused to a GAL4 DNA binding domain and a nucleic acid encoding a reporter gene operably linked to a gene expression regulatory region, such as one or more GAL4 binding sites. Activation of reporter gene transcription occurs when the RIP60 and reporter fusion polypeptides bind such as to enable transcription of the reporter gene. Agents which modulate a RIP60 polypeptide mediated cell function are then detected through a change in the expression of reporter gene. Methods for determining changes in the expression of a reporter gene are known in the art.

RIP60 fragments used in the methods, when not produced by a transfected nucleic acid are added to an assay mixture as an isolated polypeptide. RIP60 polypeptides preferably are produced recombinantly, although such polypeptides may be isolated from biological extracts. Recombinantly produced RIP60 polypeptides include chimeric proteins comprising a fusion of a RIP60 protein with another polypeptide, e.g., a polypeptide capable of providing or enhancing protein-protein binding, sequence specific nucleic acid binding (such as GAL4), enhancing stability of the RIP60 polypeptide under assay conditions, or providing a detectable moiety, such as green fluorescent protein or Flag epitope.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

The invention provides RIP60-specific binding agents, methods of identifying and making such agents, and their use in diagnosis, therapy and pharmaceutical development. For example, RIP60-specific pharmacological agents are useful in a variety of diagnostic and therapeutic applications, especially where disease or disease prognosis is associated with altered RIP60 binding characteristics. Novel RIP60-specific binding agents include RIP60-specific antibodies, and natural intracellular binding agents identified with assays such as two hybrid screens, and non-natural intracellular and extracellular binding agents identified in screens of chemical libraries and the like.

The invention also provides novel kits which could be used to measure the levels of the nucleic acids of the invention or expression products of the invention, or anti-RIP60 antibodies. In the case of nucleic acid detection, pairs of primers for amplifying RIP60 nucleic acids can be included. The preferred kits would include controls such as known amounts of nucleic acid probes, RIP60 epitopes (such as RIP60 expression products) or anti-RIP60 antibodies, as well as instructions or other printed material. The reagents may be packaged in containers and/or coated on wells in predetermined amounts, and the kits may include standard materials such as labeled immunological reagents (such as labeled anti-IgG antibodies) and the like. As an example. One kit may contain a packaged polystyrene microtiter plated coated with RIP60 polypeptide and a container housing labeled anti-human IgG antibodies. A well of the plate is contacted with for example, serum, washed and then contacted with the anti-IgG antibody. The label is then detected.

In another aspect, the invention provides a method for determining the level of RIP60 expression in a sample. The method involves measuring the expression of RIP60 in a test sample and comparing the level of expression in the test to a control. RIP60 expression can refer to expression RIP60 nucleic acid molecules which hybridizes under stringent conditions to a complement of a molecule comprising SEQ ID NO:1, SEQ ID NO:3, SEQ ID NO:5 or SEQ ID NO:50 and which codes for a polypeptide having RIP60 activity. Such nucleic acid expression products include mRNA species and 2nd strand cDNA species synthesized from the mRNA. RIP60 expression can also refer to a expression of RIP60 polypeptide, or a fragment thereof. Usually the RIP60 expression is measured using an agent which binds to either the RIP60 nucleic acid or the RIP60 polypeptide. If the level of nucleic acid expression is being measured, such a determination can be carried out via any standard nucleic acid determination assay, including the polymerase chain reaction, or assaying with labeled hybridization probes, as in a Northern analysis. In these latter embodiments, the agent is preferably a nucleic acid molecule. If the level of RIP60 polypeptide expression is being measured, such a determination can be carried out via any standard immunological assay using, for example, polyclonal or monoclonal antibodies or antisera which bind to the secreted RIP60 protein. The level of interaction between the agent and either the RIP60 nucleic acid or the RIP60 polypeptide is determined and compared with a control.

The sample can be a tissue or a biological fluid. Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. In certain embodiments, test samples originate from colon, breast and prostate tissues, and biological fluids include blood, saliva and urine. Both invasive and non-invasive techniques can be used to obtain such samples and are well documented in the art.

A control can include a known amount of a nucleic acid probe or a RIP60 epitope (such as a RIP60 polypeptide or fragment thereof). In preferred embodiments the control is a similar tissue sample from a subject with a control or 'normal' level of RIP60 expression. The invention is also useful in the generation of knock-out and/or transgenic non-human animals. As used herein, "knock-out non-human animals" include animals in which the endogenous RIP60 genomic locus has been mutated to an extent that it either can no longer be transcribed to produce mRNA, or any mRNA so produced does not lead to the production of wild-type RIP60 polypeptide. Such knock-outs are generally referred to as nulls, since neither wild-type nor mutant RIP60 polypeptides are detectably produced by the cells after mutation. Other "knock-out" animals embraced by the invention are those in which mutation and/or deletion of one or more coding regions within a genomic locus still results in the production of a protein species, albeit one which is mutant usually in the form of a truncation. This latter type of mutation, in some instances, results in the production of dominant negative forms of RIP60 polypeptide. Dominant negative forms of RIP60 polypeptides, as described herein, are mutants which still possess function, usually in the form of a negative function. An example of a dominant negative mutation is one which promotes the binding of mutant RIP60 polypeptide to its natural wild-type binding partners but prevents the natural association of the wild-type RIP60 with DNA. Such animals are useful since they can simulate varying degrees of null mutations, based on the proportion of wild-type RIP60 polypeptides which exist in the cell unassociated with the dominant negative forms of the RIP60 polypeptide.

As used herein, "transgenic non-human animals" includes non-human animals having one or more exogenous nucleic acid molecules incorporated in germ line cells and/or somatic cells. Thus transgenic animals include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to RIP60 nucleic acid molecules to increase expression of RIP60 in a regulated or conditional manner. Trans-acting negative regulators of RIP60 activity or expression also can be operably linked to a conditional promoter as described above. Such trans-acting regulators include antisense RIP60 nucleic acids molecules, nucleic acid molecules which encode dominant negative RIP60 molecules, ribozyme molecules specific for RIP60 nucleic acids, and the like. The transgenic non-human animals are useful in experiments directed toward testing biochemical or physiological effects of diagnostics or therapeutics for conditions characterized by increased or decreased RIP60 expression. Other uses will be apparent to one of ordinary skill in the art.

When the modular polypeptide is administered to a subject, the mode of administration and dosage of the modular polypeptide of the invention will vary with the particular stage of the condition being treated, the age and physical condition of the subject being treated, the duration of the treatment, the nature of the concurrent therapy (if any), the specific route of administration, and the like factors within the knowledge and expertise of the health practitioner.

When administered to a subject the modular polypeptide of the invention is administered in a pharmaceutical preparation. The pharmaceutical preparations, as described above, are administered in effective amounts. The effective amount will depend, as discussed above, upon the mode of administration, the particular condition being treated and the desired outcome. For therapeutic applications, it is that amount sufficient to cause expression of the nucleic acid being delivered at a level to achieve a medically desirable result. For instance, if the nucleic acid being delivered when expressed causes a decrease in cell proliferation, then an effective mount would be an amount that causes any decrease in cell proliferation as compared to a control. This would be useful, for instance, in the treatment of cancer.

Generally, doses of active compounds of the present invention would be from about 0.01 mg/kg per day to 1000 mg/kg per day. It is expected that doses ranging from 50–500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are commonly used for gene delivery now, inhalation e.g., by pulmonary aerosol is also used for delivery of genes to cystic fibrosis patients. Techniques for preparing aerosol delivery systems containing peptides are well known to those of skill in the art. Generally, such systems should utilize components which will not significantly impair the biological properties of the nucleic acid delivery complex (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing aerosols without resort to undue experimentation.

Compositions suitable for oral administration may be presented as discrete units, such as capsules, tablets, lozenges, each containing a predetermined amount of the nucleic acid delivery complex of the invention. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the nucleic acid if systemic delivery is desirable.

The RIP60 polypeptides or fragments thereof may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the nucleic acid delivery complex of the invention is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to deliver therapeutic levels of the nucleic acid delivery complex of the invention for at least 30 days, and preferably 60 days. Long-term sustained release implants are well-known to those of ordinary skill in the art and include some of the release systems described above.

The following examples are provided to illustrate specific instances of the practice of the present invention and are not to be construed as limiting the present invention to these examples. As will be apparent to one of ordinary skill in the art, the present invention will find application in a variety of compositions and methods.

TABLE 1

Sequence Homologies

SEQ ID NO: 1

X82192, AF000560, AF000560, M20679|HUMHKR42, AF031955|AF031955, AC005500|AC005500,
M88374|HUMZNFR, AB002324|AB002324, X71623|HSZNF741, U82672|HSU82672, X92715|HSZNF742,
M20678|HUMHKR41, X15538|GGCKR1, AC002310|HUAC002310, X63182|HSHZNF722,
AF060503|AF060503, M98502|MUSPLMZ4X, M58297|HUMMZF1, X56805|GGCKR2,
AB007407|AB007407, AF060865|AF060865, AJ003147|HSAJ03147, AC004877|AC004877,
M92433|RATNGFIC3E, M65008|RATNGFIC, X55126|MMZFP29, AB011129|AB011129,
U38864|HSU38864, M20758|MUSKROX9, X600074|HSHZNF522, U56732|RNU56732, D30612|D30612,
X60152|HSZNF2, U73479|HUMU138C3, M88360|HUMZNFD, Z30174|MDZFP30, X60154|HSZNF2B,
U39746|DVU39746, AF091512|AF091512, L01596|EUCZFB, AF017433|AF017433, Y14591|HSFUSION,
Y10898|GGGFIZINC, AC000393|AC000393, Y09723|HSMIZ1, M88357|HUMZNFA, AF017275|AF017275,
U09366|HSU09366, M19440|MUSKROX8, U14555|GGU14555, X16282|HSZFP647, M88371|HUMZNFO,
U78130|RNU78130, U46186|MMU46186, AB011665|AB011665, Y11066|DMKLUGEN,
Z25520|DVHRYWNGA, U78126|RNU78126, U67369|HSU67369, X15400|DMGLASS,
X96517|CAEFIBGEN, L01616|TCAZFB, L01594|CUPZFA, AJ131498|HSA131498, Z69720|HSRA36,
X12593|MMMKR4R, X69438|HSPAT133, U78312|MMU78312, AF084830, U49856|DVU49856,
AF086831|AF086831, Z92250|HSN86D4, AC004280|AC004280, X60104|HSZFPR, X92192|HSG5
AI019803|AI019803    AA981950|AA981950, W77266|W77266, W75846|W75846, AA396777|AA396777,
AI324137|AI324137, AA537216|AA537216, AA475809|AA475809, AA764447|AA764447,
AA960278|AA960278, AA064411|AA064411, AA013581|AA013581, AA107248|AA107248,
AA153300|AA153300, AA219819|AA219819, AA920602|AA920602, AA763378|AA763378,
W08741|W08741, AA798321|AA798321, W08046|W08046, AA03120|AA03120, AA738624|AA738624,
AA920304|AA920304, AA960001|AA960001, A1326112|A1326112, AA670744|AA670744,
AA555714|AA555714, AA184177|AA184177, A1322499|A1322499, AA562594|AA562594,
AA044497|AA044497, A1036166|A1036166, AA155283|AA155283, AA184558|AA184558, W14162|W14162,
AA266357|AA266357, AA138214|AA138214, AA797641|AA797641, AA063762|AA063762,
AA968057|AA968057, AA760366|AA760366, AA546021|AA546021, AA967007|AA967007,
AA142806|AA142806, AA137979|AA137979, AA110661|AA110661, AA939444|AA939444,
AA289228|AA289228, AI181765|AI181765, AA144904|AA144904, AA966987|AA966987,
AU014686|AU014686, AA060190|AA060190, AA097760|AA097760, AA067034|AA067034,
AA499468|AA499468, AA014148|AA014148, AI019803|AI019803 AA129215|AA129215,
AA059375|AA059375, AI087880|AI087880, AA532736|AA532736, W72943|W72943,
AA482420|AA482420, W73252|W73252, AA552911|AA552911, AA521257|AA521257,
AA012935|AA012935, AA482570|AA482570, AA888083|AA888083, N22860|N22860, AI144211|AI144211,
AA481966|AA481966, AA129342|AA129342, AI147082|AI147082, AA595548|AA595548,
AA053337|AA053337, AI183666|AI183666, AI192197|AI192197, T63243|T63243, AA465421|AA465421,
AI283669|AI283669, AI298507|AI298507, N36800|N36800, W72398|W72398, AA019573|AA019573,
AI143694|AI143694, AI014570|AI014570, AI076848|AI076848, AA126427|AA126427,
AA830292|AA830292, AA039655|AA039655, AA291840|AA291840, AI041762|AI041762,
AA282943|AA282943, AI147698|AI147698, AI086022|AI086022, AA594236|AA594236, R70860|R70860,
AA149896|AA149896, AA019713|AA019713, AA535033|AA535033, AI221122|AI221122, R72488"R72488,
AA478214|AA478214, AA293589|AA293589, AI283986|AI283986, AA766739|AA766739,
AA255706|AA255706, AA002141|AA002141, AA737654|AA737654, AA059321|AA059321,
H04064|H04064, AA121027|AA121027, N98438|N98438, AA605259|AA605259, AI244223|AI244223,
AI041422|AI041422, AA017306|AA017306 AA782169|AA782169, AA280069|AA280069,
AA742589|AA742589, AA976469|AA976469, W03591|W03591, AA282942|AA282942, N67787|N67787,
W76524|W76524, T90391|T90391, AA040587|AA040587, AA251406|AA251406, R71717|R71717,
AA053336|AA053336, AI304367|AI304367, AI003771|AI003771, AI014691|AI014691, AI017454|AI017454,
AI261391|AI261391, AI141000|AI141000, AA742283|AA742283, AA806412|AA806412,
AI076084|AI076084, AA805661|AA805661, AI304445|AI304445, AA478052|AA478052,
AA573390|AA573390, AI186888|AI186888, AI274899|AI274899, AI199967|AI199967, AI201644|AI201644,
AA478979|AA478979, AA806466|AA806466, AA768352|AA768352, AA813947|AA813947,
AI055918|AI055918, AA806927|AA806927, AA806406|AA806406,
AA914848|AA914848, AA969355|AA969355, AA129215|AA129215 C83534|C83534, C82678|C82678,
AI111565|AI111565, AA944289|AA944289, AI012263|AI012263, AI230160|AI230160, AI145532|AI145532,
AA892659|AA892659, AI232306|AI232306, AI058582|AI058582, AA891600|AA891600,
AI146184|AI146184, AI228034|AI228034, AI259059|AI259059, AA943021|AA943021, AI292769|AI292769,
AA264571|AA264571, AA536612|AA536612, AA441431|AA441431, AA695157|AA695157,
AI124327|AI124327, AI071940|AI071940, AA965102|AA965102, AA964334|AA964334,
AI011406|AI011406, AI011407|AI011407, AA957978|AA957978, AI071157|AI071157,
AA957614|AA957614, AA264471|AA264471, AA820561|AA820561, AI043656|AI043656, C83534|C83534,
SEQ ID NO: 3

I35492|I35492, I09284|, E03569|E03569, AR012092|AR012092, AR012093|AR012093,
AR009845|AR009845, AR000495|AR000495, AR009846|AR009846, I35492|I35492
AC005500|AC005500, X92715|HSZNF742, X71623|HSZNF741, AF000560|AF000560,
AC002310|HUAC002310, X63182|HSHZNF722, AB002324|AB002324, M20678|HUMHKR41,
AC004877|AC004877, M92433|RATNGFIC3E, M65008|RATNGFIC, AB011129|AB011129,
M20758|MUSKROX9, M20679|HUMHKR42, AJ003147|HSAJ03147, U82672|HSU82672,
AF060865|AF060865, M98502|MUSPLMZ4X, U39746|DVU39746, M88360|HUMZNFD, Z30174|MDZFP30,
AF031955|AF031955, AF060503|AF060503, M88357|HUMZNFA, X15538|GGCKR1, X16282|HSZFP647,

TABLE 1-continued

Sequence Homologies

X15400|DMGLASS, M88374|HUMZNFR, AB011665|AB011665, U73479|HUMU138C3,
U78126|RNU78126, M88371|HUMZNFO, Z25520|DVHRYWNGA, U78130|RNU78130,
Y11066|DMKLUGEN, L01594|CUPZFA, U1455|GGU14555, X55126|MMZFP29, M58297|HUMMZF1,
AC005732|AC005732, L01616|TCAZFB, M19440|MUSKROX8, X60104|HSZFPR, U56732|RNU56732,
AB007407|AB007407, X69438|HSPAT133, U49856|DVU49856, D30612|D30612, Y09723|HSMIZ1,
X12593|MMMKR4R, Z69363|HSL60G9B, U78139|RNU78139, AF086831|AF086831, U79264|HSU79264,
U47104|MMU47104, D76435|HUMZICP, AF00561|AF00561, M20676|HUMHKR2, D78174|D78174,
S56884|S56884, Z47205|MMPLZFGEN, AF097916|AF097916, AJ005440|DMAJ5440,
AJ002056|DMRNAD19A, AJ005441|DMAJ5441, U78119|RNU78119, AF025422|AF025422,
X63747|MMZFPTA, AF091512|AF091512, D10630|MUSZFP51, U90919|HSU90919, AE001221|AE001221,
X89483|HSP18SRNA, U41671|MMU41671, U65141|HSU65141, AF049658|AF049658,
AC004797|AC004797, M14940|DROKRA, AL008967|MTV002, AC004639|AC004639, AF017433|AF017433,
AC005500|AC005500 AI019803|AI019803, AA064411|AA064411, AA960278|AA960278, W08741|W08741,
AA798321|AA798321, AA153300|AA153300, AA555714|AA555714, AA920304|AA920304,
AA738624|AA738624, AA184177|AA184177, AI326112|AI326112, AA670744|AA670744,
AA044497|AA044497, W14162|W14162, AA138214|AA138214, AA797641|AA797641,
AA155283|AA155283, AI036166|AI036166, AA562594|AA562594,
AA968057|AA968057, AA967007|AA967007, AA760366|AA760366, AA184558|AA184558,
AA063762|AA063762, AA546021|AA546021, AA142806|AA142806, AA110661|AA110661,
AA137979|AA137979, AA097760|AA097760, AI181765|AI181765, AA067034|AA067034, W64800|W64800,
AA966987|AA966987, AA499468|AA499468, AA511236|AA511236, AA930937|AA930937,
AA144904|AA144904, AA003172|AA003172, AI182611|AI182611, W75597|W75597, AI324733|AI324733,
W17956|W17956, AA543703|AA543703, AI042688|AI042688, AI324158|AI324158, AA940187|AA940187,
AI322515|AI322515, AA637200|AA637200, AA416019|AA416019, AA289228|AA289228,
AI019803|AI019803, AA262035|AA262035, AA478052|AA478052, AI199967|AI199967,
AI141000|AI141000, AI186888|AI186888, AI280034|AI280034, AI274899|AI274899, AI221122|AI221122,
AI261391|AI261391, AI014691|AI014691, AI014570|AI014570, AI076084|AI076084, AI201644|AI201644,
AA279844|AA279844, AI304445|AI304445, AA573390|AA573390, AA662653|AA662653,
AI003771|AI003771, AA478979|AA478979, AA806466|AA806466, AA808272|AA808272,
AA768352|AA768352, AA570329|AA570329, AA810104|AA810104, AA971950|AA971950,
AI055918|AI055918, AA935598|AA935598, AA831920|AA831920, AA768007|AA768007,
AA828009|AA828009, AA806406|AA806406, AA813953|AA813953, AA742283|AA742283,
AA813947|AA813947, AA806412|AA806412, AI304607|AI304607, AI304367|AI304367,
AA814848|AA814848, H96782|H96782, AA969355|AA969355, AA922715|AA922715, AA909314|AA909314,
W93039|W93039, AI017454|AI017454, AA730282|AA730282, AI242577|AI242577, AA805661|AA805661,
AA730135|AA730135, AA975613|AA975613, AA814031|AA814031, AI050923|AI050923,
AA806927|AA806927, R06319|R06319, AA807052|AA807052, AA824558|AA824558, AI290425|AI290425,
AA731638|AA731638, R71664|R71664, AA916973|AA916973, AA837494|AA837494, AA765039|AA765039,
AA730150|AA730150, AI147698|AI147698, AI086022|AI086022, AI087880|AI087880, AI143694|AI143694,
AI283669|AI283669, AI192197|AI192197, AA290891|AA290891, AA306871|AA306871,
AI265914|AI265914, AI092709|AI092709, H43850|H43850, H47792|H47792, AI014849|AI014849,
AA960897|AA960897, AA582914|AA582914, AI038991|AI038991, AI198109|AI198109,
AI144562|AI144562, AI083715|AI083715, AI083737|AI083737, AI085490|AI085490, AA151749|AA151749,
AI192290|AI192290, AI217717|AI217717, AI264056|AI264056, AI200231|AI200231, AI239929|AI239929,
AI217783|AI217783, AI199178|AI199178, AI039895|AI039895,
AI239766|AI239766, AA972300|AA972300, AA262564|AA262564, AA994625|AA994625,
AA757828|AA757828, AI147302|AI147302, AA120778|AA120778, AI125457|AI125457,
AA262035|AA262035, AI111565|AI111565, AI012263|AI012263, AI230160|AI230160, AI058582|AI058582,
AI146184|AI146184, AA891600|AA891600, C82678|C82678, AA943021|AA943021, C83534|C83534,
AI259059|AI259059, AA264571|AA264571, AI292769|AI292769, AA264471|AA264471,
AA820561|AA820561, AI228034|AI228034, AI137516|AI137516, AI228353|AI228353, AA536612|AA536612,
AA965203|AA965203, AI237920|AI237920, AI179640|AI179640, C82417|C82417, AI146014|AI146014,
AA957288|AA957288, C83273|C83273, C12917|C12917, AI111565

EXAMPLES

The cloning and initial characterization of RIP60 is described herein. Because RIP60 binds the DSR as a homodimer (Mastrangelo, I. A., et al, (1993) J. Mol. Biol. 232, 766–778), a one hybrid screen in yeast was chosen as the cloning method due to the specificity required to distinguish RIP60 from the hundreds of other ZF proteins expressed in mammalian cells. Indeed, the one hybrid screen proved remarkably efficient, resulting in the isolation of multiple overlapping cDNAs for RIP60, each of which encoded fusion proteins that included hand Z2 (ZFs 6–8) and the PRR. More important, no other ZF protein was recovered in the screen, suggesting that the screen was both sensitive and specific.

RIP60 purified from HeLa cell nuclear extract produces a footprint of about 20 bp over both strands of the DSR (Held, P., et al, (1992) DNA Replication and the Cell Cycle, Springer-Verlag, Berlin; Dailey, L., et al, (1990) Mol. Cell. Biol. 10, 6225–6235). Footprinting and gel shift experiments indicate that the amino terminal 5 ZFs of hand Z1 and the central three ZFs of hand Z2 are sufficient for specific binding to both the DSR and USR sites in oriβ. While GST-Z1 and GST-Z2 independently recapitulate many of the features of the RIP60 footprint on the DSR, binding of GST-Z1 to either the USR or the DSR is unstable. Relative to GST-Z2, GST-Z1 does not form multimers on DNA or mediate DNA looping, and GST-Z1 has no activity in ligation enhancement assays. In contrast, the GST-Z2 fusion that contains 37 amino acids from the PRR is capable of binding both the USR and DSR in vitro, multimerizing on DNA, and forming a DNA loop in excess of 6 kB. GST-Z3 binds DNA, but does not bind the USR or DSR in vitro.

Based on the studies with the GST fusion proteins, it was concluded that GST-Z2 supports both the sequence-specific recognition of the USR and DSR and the protein-protein interactions required for looping in vitro. Deletion of the PRR reduces the stability of DNA binding by hand Z2 as well as eliminates looping. The PRR contains three consensus sequences for polyproline helices, which have been implicated in protein-protein interactions (Williamson, M. P. (1994) Biochem. J. 297, 249–260). The mechanism by which binding to DNA facilitates the protein-protein interactions required for looping is currently being investigated. Because the PRR appears to be required for both stable binding and multimerization on DNA, the present data suggest binding and looping begins with GST-Z2 first binding the USR and DSR sites in a site-specific manner and then nucleating the assembly of protein multimers on neighboring DNA sequences. It is evident from the footprinting experiments that ZFs 6–8 in hand Z2 are able to stably bind DNA sequences that border the DSR once Z2 has bound the DSR; these multimers may occupy several hundred bp of DNA. A specific binding site appears to be required for nucleating multimerization, as addition of specific DSR competitor to the ligation enhancement assays inhibits looping. Second, because GST-Z2 does not aggregate in solution, DNA binding may alter the conformation of ZFs 6–8 and/or the PRR such that the inter-molecular protein-protein interactions between distantly bound multimers required for DNA looping are favored. Finally, competition assays suggest formation of the DNA loop stabilizes both protein-DNA and protein-protein interactions in the loop, as has been observed for EBNA1 (Frappier, L., and O'Donnell, M. (1 991) Proc. Natl. Acad. Sci. USA 88, 10875–10879; 52, 53).

RIP60 has several properties similar to the origin binding protein EBNA1, which is required for the replication and maintenance of Epstein Barr Virus (EBV). EBNA1 binds as a homodimer to two sets of related sequences in EBV oriP in vitro and fosters the formation of a 900 bp DNA loop (Frappier, L., and O'Donnell, M. (1991) Proc. Natl. Acad. Sci. USA 88, 10875–10879; Su, W., et al, (1991) Proc. Natl. Acad. Sci. USA 88, 10870–10874). EBNA1 may act in replication by interacting with cellular replication factors such as RPA (Zhang, D., et al, . (1998) Nucl. Acids Res. 26, 631–637). Like EBNA1, RIP60 binds as a homodimer to two sets of sequences within an origin region, and induces the formation of a 720 bp DNA loop. While originally described as a DNA binding motif, ZFs have been implicated in binding RNA, binding RNA/DNA hybrids, and protein-protein interactions (Mackay, J. P., and Crossley, M. (1998) Trends Biochem. Sci. 23, 1–4). A homodimer of RIP60 bound to DNA would include thirty ZFs, only a portion of which are likely to be in contact with DNA. The remaining ZFs could be involved in binding RNA, other distal DNA sequences, or even other proteins.

Example 1

One Hybrid Screen for RIP60

Materials and Methods. All oligonucleotides to be used as probes or primers were synthesized and purified by a combination of denaturing gel electrophoresis and gel elution. Plasmid pBM2389 contains a histidine reporter gene regulated by an enhancerless $P_{GAL1-UAS}$ promoter (Liu, J., et al, (1993) Meth. Enzymol. 6, 1–13). pBM2389 contains a TRP1 selectable marker and CEN/ARS sequences for plasmid maintenance. Plasmid pJL638 contains a lacZ reporter gene that also is regulated by an enhancerless $P_{Gal1-uasA}^-$ promoter (Li, J. J., and Herskowitz, I. (1993) Science 262, 1870–1874). pJL638 contains a URA3 selectable marker but lacks a yeast origin to facilitate chromosomal integration. The pACT expression library contains random human B-cell cDNAs fused to sequences encoding the GAL4 activation domain under the control of an constitutive ADH promoter (Durfee, T., et al, (1993) Genes Dev. 7, 555–559). The vector pACT contains a selectable LEU2 marker and the $2\mu$ origin of replication. Two oligonucleotides representing the downstream RIP60-binding site (OCH7 and OCH8) were annealed, multimerized by ligation, and cloned into the Bam HI site located upstream of the HIS3 reporter gene in pBM2389. Clone pCH14 contains eight repeats of OCH7/OCH8 at the Bam HI site of pBM2389. Five tandem repeats of OCH7/OCH8 (5x-DSR) were removed from pCH14 as a Bam HI/Bgl II fragment and inserted into the Bam HI site of pBM2389 to generate pCH25. The TRP1 marker gene was removed from pCH25 as a Nco I fragment and replaced with the ADE2 marker from pADE2 to generate pCH47. The 5x-DSR fragment was cloned into the Bgl II site located upstream of the lacZ reporter gene in pJL638 to generate pCH33. Fragment E, which contains the downstream RIP60 binding site and surrounding bent DNA sequences (nucleotides 3382–3536 in Caddie, M. S., et al, (1990) J. Mol. Biol. 211, 19–33), was amplified by PCR cloned into the Bam HI and Bgl II sites of pUC 19 to generate pUC/E. Fragment E was removed from pUC/E as a Bam HI/Bgl II fragment and inserted into the Bgl II site of pJL638 to generate pCH36. pJL638, pCH33, and pCH36 were each linearized at the Stu I site located in the URA3 marker and integrated at the URA3 gene in yeast strain GGY1 (MATα Δgal80 Δura3 leu2 his3 ade2 tyr) by homologous recombination to generate yeast strains YCH3, YCH4, and YCH5, respectively. Integration of the lacZ reporter plasmids were confirmed by Southern blot analysis. YCH4 was transformed with pCH47 to generate the yeast one hybrid reporter strain, YCH4/pCH47.

YEPD (rich media) and SD (synthetic dropout media) were prepared as described (Gutherie, C., and Fink, G. R. (1991) *Guide to Yeast Genetics and Molecular Biology*, Academic Press, San Diego, Calif.). High efficiency yeast transformations were performed by the method of Scheistel and Geitz (Schiestl, R. H., and Gietz, R. D. (1989) Curr. Genet. 16, 339–346). YCH4/pCH47 was transformed with B-cell pACT library DNA and transformants were selected on SD plates lacking histidine, adenine, and leucine. Histidine prototrophs from the transformation ($1.9 \times 10^7$ total) were assayed for β-galactosidase production (Breeden, L., and Nasmyth, K. (1985) Cold Spring Harb. Symp. Quant. Biol. 50, 643–650) on Protran nitrocellulose filters (Schleicher and Schuell). Transformants which tested positive for lacZ expression were isolated on SD plates lacking leucine and retested for β-galactosidase production. pACT plasmids were isolated from lacZ-positive transformants and purified through bacterial transformation and plasmid isolation. The purified pACT plasmids were retested in YCH4 for beta-galactosidase production and assayed for target sequence specificity in YCH3 and YCH5. Isolated plasmids that tested positive for lacZ expression in YCH4 and/or YCH5, but not YCH3, were sequenced and analyzed in further detail. Clone 146A-1, isolated in the one hybrid screen with YCH4/pCH47, was sequenced on both strands with custom oligonucleotide primers.

Results: RIP60 was originally purified from HeLa cell nuclear extract as a DNA-binding activity that specifically recognized an ATT-rich sequence located within the Chinese hamster cell dhfr origin of replication, oriβ (Dailey, L., et al, (1990) Mol. Cell. Biol. 10, 6225–6235). Sequence analysis of tryptic RIP60 fragments identified two amino acid sequences, VAEALEEAAAK (SEQ ID NO:30), and NLVSHRRIHTGERPYA (SEQ ID NO:31), the second of which is similar to a Kruppel C2H2-type zinc finger (ZF)

DNA-binding motif. Because scanning transmission electron microscopy indicated RIP60 binds DNA as a homodimer (Mastrangelo, I. A., et al, (1993) J. Mol. Biol. 232, 766–778), a one hybrid screen in yeast was used since it was believed to provide the specificity necessary to clone the RIP60 cDNA. A genetic screen in S. cerevisiae was used to identify cDNA-encoded fusion proteins that bind the RIP60 target sequence (DSR) and activate expression of a linked reporter gene (LacZ or histidine) by recruiting a fused GAL4 activation domain (GAD) to the promoter. LacZ reporter strains were used in which lacZ expression is controlled either by five copies of the DSR target sequence (YCH4) or a single copy of the DSR embedded in its native flanking sequences (YCH5). YCH3 which did not contain a DSR sequence was used as a control.

From $14 \times 10^6$ primary transformants, 37 fusion proteins that specifically activate lacZ expression in yeast strains YCH4 and YCH5, but not YCH3, were identified. As summarized in Table 2, sequence analysis indicated that 16 overlapping clones (clone class 134B) share significant similarity to a cDNA for an HMG protein expressed in a mouse carcinoma cell line, two encode the human Oct2 transcription factor, and eight overlapping clones (class 146A) encode a protein with multiple C2H2 ZF motifs. Specificity tests indicated that each of the eight clones from the latter group encode fusion proteins that require RIP60 target sequences to induce lacZ reporter expression from YCH4 and YCH5 but not YCH3, and that each contained the Z2 and PRR region of RIP60.

TABLE 2

One Hybrid Screen Results

| Clone # | Multiplicity | YCH3 | YCH4 | YCH5 | Homologies |
|---|---|---|---|---|---|
| 134B-1 | 16 | − | + | + | mouse carcinoma cDNA |
| 146A-1 | 8 | − | + | + | human C2H2 zinc fingers |
| 122D-1 | 2 | − | + | + | human OCT-2 |
| 148A-1 | 2 | − | + | + | unique |
| 148B-2 | 3 | − | + | + | unique |
| 119B-1 | 1 | − | − | + | unique |
| 122B-1 | 1 | − | + | + | unique |
| 146D-1 | 1 | − | − | + | unique |
| 161B-2 | 1 | − | + | + | unique |
| 148C-3 | I | − | − | + | unique |
| 143B-1 | 1 | − | + | + | unique |

Example 2

Isolation of Full-length RIP60 cDNA

Materials and Methods: To isolate full-length clones that encompass the 146A-1 cDNA, XL1-Blue bacterial cells (Stratagene) were infected with a HeLa cDNA library constructed in Lamda Zap (Stratagene) and viral plaques were transferred to Hybond N+ nylon membranes (Amersham). The filters were probed with a random-primed (Life Technologies) radiolabeled probe from the 143A-1 cDNA, which overlaps clone 146A-1. Positive plaques were purified in a secondary screen and pBluescript plasmids excised from isolated Lamda Zap viral particles were sequenced with M13/pUC forward and reverse primers. Of several positive full length clones, pBS-27 was sequenced on both strands (Genbank accession # AF201303).

Results: Using clone 146A-1 as probe, a HeLa cDNA phage library was used to isolate the full length cDNA for the ZF protein. Two clones with polyA tails of different lengths but otherwise identical cDNA sequence were isolated. The 2.9 kb cDNA of pBS-27 has 129 bp of untranslated 5' sequence, an open reading frame that encodes a 567 amino acid protein of 63 kD (shown in Table 3), and 1124 bp of 3' non-translated sequence including the poly A tail. Sequence analysis shows the open reading frame includes the two RIP60 peptides (underlined), 15 Kruppel-like C2H2 ZF motifs (bolded), and a proline-rich region between ZFs 8 and 9. Table 4 shows the alignment of the zinc fingers of RIP60, as well as the corresponding consensus sequence. The 15 ZFs are organized in three clusters, which are referred to as hand Z1 (ZF 1–5), Z2 (ZF 6–8) and Z3 (ZF 9–15). The Z1 domain corresponds to amino acids 1–231, the Z2 domain corresponds to amino acids 225–349 and the Z3 domain corresponds to amino acids 343–567. Other than the ZF motifs, no regions of homology to other proteins were identified. A proline-rich region (PRR) predicted to form three polyproline helices separates hands Z2 and Z3. Based on the DNA binding specificity, predicted molecular weight, and the presence of the two novel peptide sequences, it was concluded that the 2.9 kb cDNA of clone pBS-27 encodes RIP60.

TABLE 3

Amino Acid Sequence of RIP60

MLERRCRGPLAMGLAQPRLLSGPSQESPQTLGKESRGLRQQGTSVAQSGA
              1                                                        2

QAPGRAHRCAHCRRHFPGWBALWLHTRRCQARLPLPCPECGRRFRHAPFL
        3                                             4

ALHRQVHAAATPDLGFACHLCGQSFRGWVALVLHLLAHSAAKQPIACPKC
                           5

ERRFWRRKQLRAHLRRCHPPAPEARPFICGNCGRSFAQWDQLVAHKRVHV
                           6

AEALEEAAAKALGPRPRGRPAVTAPRPGGDAVDRPFQCACCGKRFRHKPN
               7                                      8

LIAHRRVHTGERPHQCPECGKRFTNKPYLTSHRRIHTGEKPYPCKECGRR

FRHKPNLLSHSKIHKRSEGSAQAAPGPGSPQLPAGPQESAAEPTPAVPLK
                           9

PAQEPPPGAPPEHPQDPIEAPPSLYSCDDCGRSFRLERFLRAHQRHDTGE
               10                                11

RPFTCAECGKNFGKKTHLVAHSPVHSGERPFACEECGRRFSQGSHLAAHR
               12                                13

PDHAPDRPFVCPDCGKAFRHKPYLARHRRIHTGEKPYVCPDCGKAFSGKS
               14                                15

NLVSHRRIHTGERPYACPDCDRSFSQKSNLITHRKSHIRDGAFCCAICGQ

TFDDEERLLAHQKKHDV (SEQ ID NO:2)

TABLE 4

Alignment of RIP60 Zinc Finger Amino Acid Sequence

| Hand | Zinc Finger | β1 β2 α helix | |
|---|---|---|---|
| Hand Z1 | 1 | HRCAHCRRHFPGWVALWLHTRRCQ | (SEQ ID NO:32) |
| | 2 | LPCPECGRRFRHAPFLALHRQVHA | (SEQ ID NO:33) |
| | 3 | FACHLCGQSFRGWVALVLHLLAHS | (SEQ ID NO:34) |
| | 4 | IACPKCERRFWRRKQLRAHLRRCH | (SEQ ID NO:35) |
| | 5 | FICGNCGRSFAQWDQLVAHKRVHV | (SEQ ID NO:36) |

TABLE 4-continued

Alignment of RIP60 Zinc Finger Amino Acid Sequence

| Hand | Zinc Finger | β1 β2 α helix | |
|---|---|---|---|
| Hand Z2 | 6 | FQCACCGKRFRHKPNLIAHRRVHT | (SEQ ID NO:37) |
| | 7 | HQCPECGKRFTNKPYLTSHRRIHT | (SEQ ID NO:38) |
| | 8 | YPCKECGRRFRHKPNLLSHSKIHK | (SEQ ID NO:39) |
| Hand Z3 | 9 | YSCDDCGRSFRLERFLRAHQR-HD | (SEQ ID NO:40) |
| | 10 | FTCAECGKNFGKKTHLVAHSPVHS | (SEQ ID NO:41) |
| | 11 | FACEECGRRFSQGSHLAAHRPDHA | (SEQ ID NO:42) |
| | 12 | FVCPDCGKAFRHKPYLARHRRIHT | (SEQ ID NO:43) |
| | 13 | YVCPDCGKAFSQKSNLVSHRRIHT | (SEQ ID NO:44) |
| | 14 | YACPDCDRSFSQKSNLITHRKSHI | (SEQ ID NO:45) |
| | 15 | FCCAICGQTFDDEERLLAHQKKHD | (SEQ ID NO:46) |
| consensus | | --C--C---F-----L--H---H- | (SEQ ID NO:47) |

Example 3

Construction of Expression Plasmids for GST-, HA-, and GFP-tagged Fusion Proteins Materials and Methods: pGEX-2T and pGEX-5X-1 (Pharmacia Biotech) were used for expressing GST-tagged fusion proteins, pCMV-HA (Baker, S. J., et al, (1990) Science 249, 912–915) for expressing HA-tagged fusion proteins, and pK7-GFP for expressing GFP-tagged fusion proteins. The following RIP60 cDNA fragments were amplified by PCR with the indicated primer sets using pBS-27 as a template: Z123 (RIP1/RIP4, nucleotides 1–1704), Z12 (RIP1/RIP5, nucleotides 1–1058), Z1 (RIP1/RIP6, nucleotides 1–702), Z23 (RIP2/RIP4, nucleotides 682–1704), Z3 (RIP3/RIP4, nucleotides 1039–1704), Z2 (RIP2/RIP5, nucleotides 682–1058), Z12P (RIP1/RIP9, nucleotides 1–1122), Z12ΔP (RIP1/RIP7, nucleotides 1–948). Z2P (RIP2/RIP9, nucleotides 682–1122), Z2ΔP (RIP2/RIP7, nucleotides 682–948), PZ3 (RIP8/RIP4, nucleotides 949–1704), and ΔPZ3 (RIP10/RIP4, nucleotides 1123–1704). The following PCR products were digested with Bam HI and inserted in frame into the Bam HI site of pGEX-2T to generate the indicated plasmids for the purification of GST fusion proteins: Z123 (pCH59), Z23 (pCH61), Z3 (pCH126), Z12 (pCH65), Z2 (pCH67), and Z1 (pCH69). The following PCR products were digested with Bam HI and inserted in frame into the Bam HI site of pCMV-HA to generate the indicated plasmids for the expression of HA-tagged fusion proteins: Z123 (pCH71), Z23 (pCH73), Z3 (pCH75), Z12 (pCH76), Z2 (pCH78), Z1 (pCH79), Z12ΔP (pCH89), Z12P (pCH91), Z2ΔP (pCH93), Z2P (pCH94), ΔPZ3 (pCH96), and PZ3 (pCH108). The following PCR products were digested with Bam HI and inserted in frame into the Bam HI site of pK7-GFP to generate the indicated plasmids for the expression of GFP fusion proteins: Z12 (pCH83), Z1 (pCH84), Z2 (pCH85), Z123 (pCH86), and Z23 (pCH88).

Results: The RIP60 cDNA and various truncated versions of the RIP60 open reading frame were inserted into several expression vectors for production of GST fusion proteins in bacteria, and HA and GFP-tagged proteins in mammalian cells. The expression and localization of the HA- and GFP-tagged fusion proteins in mammalian cells were first examined. Western blot analysis demonstrated that each recombinant HA-tagged fusion protein was expressed in mouse NIH 3T3 cells in accord with its predicted size. Despite the lack of an obvious nuclear localization signal, fluorescence microscopy of transfected CHOC 400 and NIH 3T3 cells also showed each RIP60 GFP fusion protein was localized primarily in the cell nucleus.

Example 4

Purification of GST-tagged RIP60 Fusion Proteins

Materials and Methods. BL21 bacterial cultures (400 ml) were grown in LB media containing ampicillin (100 ug/ml) in the presence of 50 µM ZnCl2 to 1.0 OD600 and 1 mM IPTG was then added for 5 hours at 37° C. Cells were pelleted by centrifugation, resuspended in 10 ml lysis buffer (1×PBS, 10 mM β-mercaptoethanol, 1 mM PMSF, 25 ug/ml aprotinin, 25 ug/ml leupeptin, 1 mg/ml lysozyme), and incubated on ice for 20 minutes. Cells were lysed by sonication on ice, Triton X-100 was added to 1%, and the cell lysate was cleared by centrifugation before addition of glutathione SEPHAROSE™ beads (Pharmacia Biotech) for 2 hours on ice with rocking. The beads were washed several times with ice-cold PBS with 1% Triton X-100 and then PBS before elution with ten serial additions of glutathione elution buffer (20 mM reduced glutathione, 100 mM Tris-HCl (pH 8.0), 120 mM NaCl, 0.1% Triton X-100). Protein fractions were flash frozen in liquid nitrogen and stored at −80° C. Protein concentrations were estimated by comparison to known protein standards on Coomasie Blue stained protein gels.

Mouse NIH 3T3 cells were maintained in Dulbecco's Modified Eagle Medium (DMEM) supplemented with 10% calf serum. CHOC 400 and HeLa cells were maintained in DMEM media supplemented with 5% fetal bovine serum. CHO K1 cells were maintained in F12 media supplemented with 5% fetal bovine serum. Cells were at 50% density and incubated for 24 hours prior to transfection by calcium phosphate coprecipitation as described previously (Magae, J., et al, (1996) J. Cell Sci. 109, 1717–1726).

Mammalian nuclear extracts were prepared as described (Staal, F. J., et al, (1990) Proc. Natl. Acad. Sci. USA 87, 9943–9947). Briefly, cells on 100 mM dishes were washed 2× with ice-cold PBS and buffer A (10 mM HEPES (pH 8.0), 10 mM KCl, 2 mM MgCl2, 0.1 mM EDTA (pH 8.0), 1 mM DTT, 0.2 mM sodium vanadate, 0.4 mM PMSF, 0.3 ug/ml leupeptin, 0.2 mM NaF) was added. The cells were scraped with buffer into microfuge tubes and incubated on ice for 15 minutes. Buffer B (10% Nonidet P40) was added, the cell lysate was vortexed for 15 seconds, and then centrifuged for 30 seconds at 14,000 rpm in a microfuge at 4° C. The supernatant (cytoplasmic fraction) was discarded and the intact nuclei pellet was resuspended in an ice-cold mixture of 800 ul buffer A and 50 ul buffer B. The nuclear suspension was vortexed for 15 seconds, centrifuged for 30 seconds at 14,000 rpm in a microfuge at 4° C., and the supernatant was removed. The nuclear pellet was resuspended in 100 ul ice-cold buffer C (50 mM HEPES (pH 7.8), 50 mM KCl, 300 mM NaCl, 0.1 M EDTA (pH 8.0), 10% glycerol, 1 mM DTT, 0.2 mM sodium vanadate, 0.667 mM PMSF, 0.2 mM NaF), mixed gently at 4° C. for 20 min, and centrifuged for 5 min at 14,000 rpm in a microfuge at 4° C. The supernatant (nuclear extract) was transferred to a new microfuge tube, flash frozen in liquid nitrogen, and stored at −80° C.

Results: RIP60 purified from HeLa nuclear extract binds specifically to two inverted ATT-rich sequences within oriβ, as determined by DNaseI footprinting, competitive gel shift analysis, and scanning transmission electron microscopy (Dailey, L., et al, (1990) Mol. Cell. Biol. 10, 6225–6235; Mastrangelo, I. A., et al, (1993) J. Mol. Biol. 232, 766–778). To map the DNA binding domains of RIP60, GST fusion proteins containing hands Z1, Z2, and Z3 (and combinations thereof) were used in gel mobility shift and DNase I footprinting assays. Binding studies were performed with nuclear extracts from A) bacterial cells expressing full length RIP60 GST-fusion protein mouse, and b) NIH 3T3 cells transfected with a mammalian expression vector containing the human RIP60 coding sequence (pCMV-HA-Z123).

Example 5

Electrophoretic Gel Mobility Shift Assays

Materials and Methods: The following oligonucleotides were annealed (10 pmole/ul final concentration) in the presence of 1×STE buffer (100 mM NaCl, 10 mM Tris-Cl (pH 8.0), 1 mM EDTA) to generate the indicated double-stranded probes: OCH7/OCH8 (DSR), OCH13/OCH14 (IBF), OCH35/OCH36 (SV-AT), OCH37/OCH38 (Py-AT), and OCH39/OCH40 (USR). DSR (50 pmole) was labeled by Klenow fill-in reaction of 5' overhangs in the presence of [$\alpha$-$^{32}$P]-dATP. Other probes were end-labeled with polynucleotide kinase and [$\gamma$-$^{32}$P]. Binding reactions (30 ul) contained 0.05 pmole labeled DSR probe, 40 mM KCl, 10 mM HEPES (pH 8.0), 4% Ficoll, 33 ng/ul poly dIdC, 1 mM DTT, 16.7 uM $ZnCl_2$, and 0.5–10 ug of protein. Binding reactions were incubated for 20 minutes at 37° C., 15 min on ice, and then resolved on 6% native polyacrylamide gels in 0.25×TBE buffer. Gels were dried, exposed to Kodak XAR film at −80° C., and signals were detected by autoradiography. Competition binding reactions were assembled as described above with the addition of 0.5, 5, or 50 pmole of unlabeled double-stranded competitor DNA to the reactions prior to the addition of protein. For time course competition assays, 60 ul binding reactions were assembled and incubated as above. Following the incubation step on ice, 50 pmole of unlabeled DSR competitor DNA was added to the binding reactions and samples where removed at the indicated time points, loaded on a 6% native PAGE gel, and resolved by electrophoresis at 25V until all samples were loaded. After the final sample was loaded, the voltage was increased to 100V and samples were resolved by electrophoresis for an additional 1.5 hours. Signals on the dried gels were quantified on a phosphoimager (BioRad model GS 525). A value for % probe bound was calculated as a ratio of protein-bound probe to total probe (bound and unbound probe) per sample and values were plotted against time.

Results: Competitive gel shift analyses showed that full-length RIP60 (HA-Z123) binds to the DSR probe in the presence of a 1000-fold molar excess of an intron binding factor site (IBF), and/or the AT-rich regions from either the SV40 or polyomavirus origins of replication (SV-AT and Py-AT, respectively), and that binding is competed by a 10-fold excess of DSR DNA. Because the AT-rich sequences from the SV40 and polyomavirus origins of replication (SV-AT and Py-AT) failed to compete for binding, it was concluded that full-length RIP60 binds the ATT-rich DSR specifically, and is not a general AT-rich DNA binding protein. Addition of anti-HA monoclonal antibody 12CA5 to nuclear extract from cells transfected with pCMV-HA-Z123 supershifted the putative HA-Z123/DSR complex, verifying that the specific DNA-binding activity resulted from expression of HA-tagged RIP60.

Binding of GST-Z1 to the DSR probe was eliminated by a 100-fold excess of DSR competitor DNA, but was not significantly affected by large molar excesses of the IBF, SV-AT, or Py-AT competitors. A slight competitive effect was observed in the presence of 1000-fold excess of Py-AT competitor DNA. Binding of the GST-Z2 to the DSR probe was stable in the presence of 1000-fold excess of IBF, SV-AT, or Py-AT competitors, but was competed with 100-fold excess of unlabeled DSR DNA. Similar binding specificities were observed for GST-Z12 and GST-Z23. In contrast, binding of GST-Z3 to the DSR probe was eliminated by a 1000-fold excess of all unlabelled competitors tested. From these results, it was concluded that GST-Z123, GST-Z12, GST-Z2 and GST-Z23 all bind specifically to the DSR from oriβ. In a like manner, the USR was also able to compete for binding of these proteins to the DSR. These results are consistent with findings using purified RIP60 and indicate that full length RIP60 binds specifically to the USR and DSR ATT-rich target sites, but not all AT-rich sequences.

Example 6

In vitro DNase I Footprinting

Materials and Methods: Probe DHFR-E-top was generated by digesting pUC/E with Bam HI, end-labeling by Klenow fill-in in the presence of [$\alpha$-$^{32}$P]-dATP, and digesting with Bgl II. Probe DHFR-E-bottom was generated by digesting pUC/E with Bgl II, end-labeling by Klenow fill-in in the presence of [$\alpha$-$^{32}$P]-dATP, and digesting with Bam HI. Footprinting probes were purified by gel electrophoresis and Geneclean (Bio 101), and resuspended in distilled water at a specific activity of 50,000 dpm/ul. Binding reactions (50 ul) that contained 50,000 dpm of labeled probe were assembled as for gel mobility shift assays. After incubation at 37° C. for 20 min and on ice for 15 min, one volume of a 5 mM $CaCl_2$, 10 mM MgCl2 solution was added for one minute at room temperature, followed by the addition of 0.02 units of DNase I for 1 min. Footprinting reactions were stopped with the addition of 90 ul prewarmed stop buffer (200 mM NaCl, 30 mM EDTA, 1% SDS), extracted with phenol, ethanol precipitated, and resuspended in sequencing dye buffer. Samples were resolved by electrophoresis at 65 W for 1.5 to 3.0 hours on denaturing 8% polyacrylamide gels. The gel was dried, exposed to Kodak XAR film at −80° C., and signals were detected by autoradiography.

Results. To examine the interaction of RIP60 and hands Z1 and Z2 with the DSR in more detail, in vitro DNase I footprinting assays were performed with end-labeled DHFR-E, a 250 bp bent DNA fragment which contains the DSR and a neighboring consensus AP-1 binding site. DNase I footprinting assays with RIP60 purified from HeLa cell nuclear extract showed that the protein protects the ATT-rich DSR sequence on the top strand of DHFR-E from nucleotide position 3461 to position 3481, and from position 3476 to position 3461 on the bottom strand (Dailey, L., et al, (1990) Mol. Cell. Biol. 10, 6225–6235). Binding of RIP60 to the DSR also induces a characteristic nuclease hypersensitive site at position 3483 that borders the protected sequences on the top strand.

GST-RIP60 protected the DSR sequences from DNase I digestion on both the top strand (positions 3461 to 3481) and bottom strand (positions 3476 to 3461) of the DHFR-E probe, while little protection from nuclease cleavage was observed outside of the DSR target. While the region of nuclease protection provided by GST-RIP60 mapped to the same nucleotide residues observed in footprinting experiments using native RIP60, the recombinant fusion protein did not induce hypersensitive sites within flanking sequences on either the top or bottom strands of the DHFR-E probe.

GST fusion proteins possessing either the Z1 or Z2 domains (GST-Z1, GST-Z2, GST-Z12, GST-Z23) protected the same DSR sequences on both strands of the DHFR-E probe from nuclease digestion as did GST-RIP60 and native RIP60 (Dailey, L., et al, (1990) Mol. Cell. Biol. 10, 6225–6235). Fusion proteins containing hand Z2 induced multiple hypersensitive sites on the top strand of DHFR-E, including the prominent site at position 3483. At higher protein concentrations both GST-Z2 and GST-Z23 protected sequences extending through the AP-1 site toward the end of DHFR-E. In contrast, GST-Z3 did not protect any sequence on either strand of the DHFR-E probe from DNase I cleavage. These results are consistent with the gel shift experiments which indicate that Z3 domain of RIP60 does not recognize the DSR. GST-Z12 bound the DSR and produced the same nuclease protection patterns as GST-Z1 or GST-Z2, but it did not induce nuclease hypersensitive sites on either strand of the DHFR-E probe that were observed with GST-Z2 or GST-Z23. Rather the pattern of nuclease protection and hypersensitivity induced by GST-Z12 was virtually identical to that of GST-RIP60 (or Z123).

The footprinting results demonstrated that GST-RIP60, and truncated forms of RIP60 that contained either domains Z1 or Z2, bound specifically to the DSR target, protecting both strands of the bent DNA region from DNase I cleavage in a manner similar to the full length protein. The observation that GST-Z2 and GST-Z23, at higher protein concentrations, protected sequences adjacent to the DSR also suggests that sequences within the hand Z2 construct are sufficient for multimerization of RIP60 on DNA. Specific binding of GST-Z2 is more stable than that of GST-Z1.

Both GST-Z1 and GST-Z2 bound the DSR and USR specifically in footprinting and gel shift experiments, suggesting that RIP60 contains two independent domains capable of recognizing ATT-rich binding sites. To ascertain if Z1 and Z2 show any differences in binding activity, the stability of Z1 and Z2 complexes with the DSR was examined in competition gel shift assays. Identical amounts of GST-Z1 and GST-Z2 were incubated with $^{32}$P-labeled probe for 20 min, and then a 1000-fold molar excess of unlabeled competitor DSR was added. Samples were removed from the binding reactions at various times thereafter and loaded directly onto non-denaturing gels running at low voltage. After all the samples were loaded, the voltage was increased to 100V for 1 hr. After drying the gels, the signals in the shifted complexes were quantified by phosphoimaging. As shown in FIG. 3, the CPM within the protein/DNA complexes are expressed as a percentage of the total signal per lane (i.e. bound probe over bound plus free probe). Under these binding conditions, binding of GST-Z2 to the DSR appeared significantly more stable over time than that of GST-Z1.

Example 7

Ligation Enhancement Assays

Materials and Methods: Ligation enhancement assays were performed as described (Goldsmith, K., et al, (1993) J. Virol. 67, 3418–3426), with some modifications. Primers p512 and p521 were used to amplify a 1118 bp fragment of dhfr oriβ from pMC-D (nucleotides 2434–3536 in Caddle, M. S., et al, (1990) J. Mol. Biol. 211, 19–33). The oriβ fragment was cut with Bam HI and Bgl II and cloned into the Bgl II site of pPyOICAT to generate pCH127. pCH127 was linearized at the Acc I site and purified to generate the pCH127 (Acc I) substrate. Where indicated, pCH127(Acc I) was dephosphorylated by treatment with calf intestine alkaline phosphatase (CIP). Binding reactions (50 ul) were assembled that contained 100 ng pCH127(Acc I), 2 mM DTT, 2 mM ATP, 20 uM ZnCl2, 20 mM MgCl2, 40 mM KCl, 10 mM HEPES (pH 8.0), 4% Ficoll, and 100 ng GST-fusion protein (where indicated, 5.0 pmole of competitor DNA was added prior to the addition of protein). Binding reactions were incubated at room temperature for 15 min and diluted with the addition of 50 ul distilled water. One Weiss unit of T4 DNA ligase was added and reactions were incubated for 5 minutes at 15° C. An equal volume of PK buffer (10 mM Tris-HCl (pH 7.8), 5 mM EDTA, 0.5% SDS) containing 20 ug Proteinase K was then added to the samples and protein was digested for one hour at 37° C. Samples were extracted with phenol, ethanol precipitated, resuspended in 30 ul distilled water, resolved on 1% agarose gels in TAE buffer, transferred to nitrocellulose, and probed with radiolabeled pPyOICAT. Blots were washed and exposed to Kodak XAR film for 1 to 10 minutes at room temperature.

Results: Hand Z2 is sufficient for DNA looping by RIP60. DNA looping by origin binding proteins has been shown to be functionally important in both plasmid and viral DNA replication. To begin mapping of the domains involved in DNA looping by RIP60, a ligation enhancement assay was used. The assay detects changes in the efficiency of end-to-end ligation of a linear plasmid when proteins bound near the ends of the DNA template interact to bring the plasmid ends in close proximity to one another (Goldsmith, K., et al, (1993) J. Virol. 67, 3418–3426). For ligation enhancement assays, the URS and DRS RIP60 binding sites were separated by approximately 6 kb by linearizing pCH127 with Acc I. In the linear pCH127 substrate, the USR and DSR sites are located 300 and 450 bp from the DNA ends, respectively.

In the absence of protein or ligase, only the linear pCH127 plasmid template was observed, while the addition of ligase alone for 5 min generated two ligation products. The addition of GST-Z1 or GST-Z3 had little effect on the plasmid ligation products when compared to ligase alone. The addition of GST-Z2, GST-Z12, or GST-RIP60 altered the distribution of ligation products, resulting in the formation of more slowly migrating bands. The addition of GST-Z23 had no effect in this experiment. The presence of DSR competitor inhibited the ability of GST-Z2 to enhance plasmid ligation, while the presence of an excess amount of the SV-AT competitor DNA had no effect. These results indicate that binding of GST-Z2 to the linear pCH127 plasmid at the USR and DSR was required to enhance ligation of the template under these conditions. The ligation products induced by GST-Z2 also required 5'-phosphates on the substrate, as prior dephosphorylation of the linear pCH127 template with calf intestinal phosphatase prevented GST-Z2 ability to enhance plasmid ligation.

To assess the role of the PRR in DNA looping, the binding activity of GST-Z2 was compared to GST-Z2ΔP in gel mobility shift, ligations enhancement and atomic force microscopy DNA looping assays. At equivalent protein concentrations GST-Z2 bound the DSR probe more avidly then did GST-Z2ΔP. While the weak binding of GST-Z2ΔP was specific, it did not form multimers on the gel shift probe as did GST-Z2. In ligation enhancement assays, addition of ligase alone for 20 min resulted in a broader spectrum of ligation productions as compared to the addition of ligase for 5 min. As before, addition of GST-Z2 markedly increased the efficiency of end-to end ligation of linear pCH127, yielding products similar to those observed with ligase alone after 20 min. GST-Z2ΔP, at any protein concentration tested, had no effect. These results suggest that the PRR is involved in protein-DNA and/or protein-protein interactions required for DNA looping by RIP60. Table 5 summarizes the functional properties of RIP60 domains.

TABLE 5

Functional Analysis of RIP60 Domains
The proline-rich region is required for protein multimerization and DNA looping

| | GST-Z2ΔP | GST-Z2P1 | GST-Z2(P12) | GST-Z2-P123 |
|---|---|---|---|---|
| DNA Binding | + | ++ | +++ | +++ |
| Gel shift Multimers | − | − | ++ | +++ |
| DNA Looping | − | − | ++ | +++ |

Example 8

Atomic Force Microscopy

Materials and Methods: The ability of GST-Z2 to bind and condense BAC 269 was evaluated by atomic force microscopy (AFM). The binding and imaging conditions for AFM of GST-Z2-DNA complexes are described briefly. Atomic force microscopy studies were performed using a Nanoscope III AFM (Digital Instruments) equipped with a Plexiglass tapping-mode fluid cell. The microscope was operated in fluid tapping mode using cantilever frequencies between 12 and 24 kHz. Triangular silicon nitride cantilevers (100 μm) with oxide sharpened oriented twin-tips having a normal spring constant of 0.1 N/m were used. Linear and supercoiled DNA was diluted to 100 ng/ul in TE. Binding reactions (5 ul) were assembled that contained 1–2 ul template DNA, 1 ul GST-fusion protein (50–100 ng/ul), and 2 ul holding buffer (20 mM Tris-HCl, pH 8, 50 mM KCl, 5 mM $MgCl_2$, 1 mM β-mercaptoethanol) then incubated for 20 minutes at room temperature and then stored on ice until imaged. Binding reactions were diluted (1:16) in deposition buffer (20 mM Tris-HCl (pH 7.5), 5 mM KCl, 5 mM $MgCl_2$, 1 mM β-mercaptoethanol, 2 mM $ZnCl_2$) and 7 ul was deposited on freshly cleaved mica chips. Samples were imaged by AFM while still wett using silicon nitride probes in the fluid tapping mode. DNA concentrations of 2–10 ng/ul proved optimal for high resolution imaging.

Results: AFM of BAC 269 showed large contiguous circular or linear molecules with structural features similar to other DNA molecules which have been imaged under similar conditions. The DNA is extended, twisted and looped in a random fashion, with free ends apparent in several preparations (FIG. 4A). When incubated with GST-Z2, BAC 269 DNA becomes condensed, with one or more protein multimers per molecule (FIG. 4B). These results show that GST-Z2 is able to bind, condense, and/or link linear, circular and supercoiled plasmid DNA molecules in vitro.

To confirm the results of the DNA looping studies, DNA binding of GST-Z2 (FIG. 5A) and GST-Z2ΔP (FIG. 5B) to linear pCH127 was analyzed by AFM. In the presence of GST-Z2, looping between the upstream and downstream binding sites was readily evident. In several instances the ends of the linear pCH127 DNA were observed to protrude from the looped DNA complex. When GST-Z2ΔP was used in AFM experiments, stable binding to the USR or DSR on the linear DNA substrate was rarely observed, and loops between the two sites were not detected.

These experiments demonstrate that GST-Z2 can be used to condense DNA prior to the introduction of the DNA into mammalian cells. Condensation of DNA represents an important step in the capture of DNA for introduction into the cell.

Example 9

Polyoma Virus Origin-dependent Replication Assays

Materials and Methods. The following reporter plasmids were used in replication assays: pPyOICAT is a reporter plasmid that contains the polyomavirus core origin of replication but lacks the enhancer region (Murakami, Y., et al, (1991) Proc. Natl. Acad. Sci. USA 88, 3947–3951); pPy (AM)6OICAT contains six AP-1 binding sites in the enhancer region of pPyOICAT (Ito, K., et al, (1996) EMBO J. 15, 5636–5646); pBOS-LT is a polyomavirus large T-antigen expression (Ito, K., et al, (1996) EMBO J. 15, 5636–5646). Plasmids pRSV-FOS and pRSV-JUN are mammalian expression plasmids for the c-Fos and c-Jun proteins. Fragment E was removed from pUC/E as a Bam HI/Bgl II fragment and inserted into the Bgl II site of pPyOICAT to generate pPy(DHFR-E)OICAT. 5×-DSR was removed from pCH14 as a Bam HI/Bgl II fragment and inserted into the Bgl II site of pPyOICAT to generate pCH30. Unmethylated pUC19 was isolated and purified from pUC19 transformed dam-E. coli cells. For replication assays, NIH 3T3 cells were transfected by calcium phosphate coprecipitation with DNA samples that contained reporter plasmid DNA (500 ng), pEF-BOS-LT (4 ug), effector plasmid DNA (4 ug), unmethylated pUC19 (200 ng), and sheared salmon sperm DNA (12.7 ug total DNA). Forty-eight hours after transfection, cells were scraped into 15 ml polypropylene tubes, pelleted by centrifugation, and washed twice with PBS. Cells were resuspended in PBS and a sample of the cell suspension was removed for protein analysis. The cell samples for protein analysis were pelleted by centrifugation, resuspended in SDS gel-loading buffer, boiled for 10 minutes, and assayed for protein expression by Western blot analysis using anti-HA monoclonal antibody 12CA5. The remainder of the cell samples for DNA analysis were pelleted by centrifugation, and lysed by pipetting in the presence of 500 ul HIRT neutral lysis buffer (0.5% SDS, 100 mM NaCl, 5 mM EDTA (pH 8.0), 10 mM Tris-Cl (pH 8.0) (Hirt, B. (1967) J. Mol. Biol. 26, 365–369). The samples stored overnight at 4° C., the precipitate then was pelleted by centrifugation for 30 minutes at 14,000 rpm at 4° C., and the soluble DNA in the supernatant was extracted with phenol and chloroform, precipitated with ethanol, and resuspended in 60 ul distilled water. DNA samples (20 ul) were digested for 2 hours with Eco RI and Dpn I and resolved by electrophoresis on a 1% agarose in 1×TBE. DNA was transferred to a nitrocellulose membrane by Southern blotting. The Southern blots were probed with a random-primed radiolabeled pPyOICAT probe specific for the reporter plasmid and pUC19, washed, and exposed to Kodak XAR film. Probe-specific signals were quantified by phosphoimager analysis and a replication efficiency value was determined from two independent transfections as the ratio of signal from replicated reporter DNA relative to pUC19 DNA.

Results: In an attempt to study the effects of RIP60 expression on DNA replication, a polyomavirus (Py)-based transient plasmid replication assay was used. The Py core origin requires an enhancer for activity (reviewed in Hassell, J. A., and Brinton, B. T. (1996) *DNA Replication in Eukaryotic Cells*, Cold Spring Harbor Laboratory, Cold Spring Harbor, N.Y., pp. 639–677). When the enhancer element is replaced with binding sites for a variety transcription factors, the cognate transcription factors are able to stimulate Py origin-dependent plasmid replication, providing the transcription factors contain a transcriptional activation domain (Hassell, J. A., and Brinton, B. T. (1996) *DNA Replication in Eukaryotic Cells*, Cold Spring Harbor Laboratory, Cold Spring Harbor, N.Y., pp. 639–677). For example, the heterodimeric transcription factor complex of Fos and Jun (AP-1) has been shown to enhance replication from the polyomavirus origin of replication through the agency of AP-1 binding sites located in the enhancer (Ito, K., et al, (1996) EMBO J. 15, 5636–5646; Guo, Z. S., and DePamphilis, M. L. (1992) Mol. Cell. Biol. 12, 2514–2524). The polyomavirus origin-dependent plasmid replication assay utilized four plasmid components: (a) a reporter plasmid containing the Py core origin of replication that harbors protein recognition sequences in place of the native viral enhancer region, (b) a Py large T-antigen expression plasmid required for replication of the reporter plasmid, (c) effector plasmids expressing HA-tagged RIP60 fusion proteins or control transcription factors and (d) unmethylated pUC19 plasmid DNA (pUC19⁻) which serves as an internal control for transfection efficiency and plasmid recovery. The reporter plasmids used here were derived from pPyOICAT (Ito, K., et al, (1996) EMBO J. 15, 5636–5646) and contained either six AP-1 binding sites (pPy-AM6OICAT), the 250 bp DHFR-E fragment (pPy-DHFR-E-OICAT), or the 5×DSR fragment (pCH30).

As a positive control, NIH 3T3 cells were transfected with the pPy(AM)6OICAT reporter plasmid in the absence or presence of Fos and Jun effector plasmids. Consistent with the results of others (Ito, K., et al, (1996) EMBO J. 15, 5636–5646; Guo, Z. S., and DePamphilis, M. L. (1992) Mol. Cell. Biol. 12, 2514–2524), coexpression of Fos and Jun stimulated replication of the pPy(AM)6OICAT reporter by approximately 40-fold over control. In contrast, expression of RIP60 increased replication of a reporter plasmid with 5 copies of the DSR in the enhancer region (pCH30) only about 3.5 fold. RIP60 had no effect on replication of the enhancerless plasmid OICAT or on the DHFR-E plasmid with a single binding site in context of the bent DNA sequence.

Example 10

Efficient Transfer of BAC269 Into CHOC400 Cells by GST-Z2 and Lipofectamine

Material and Methods: For transfection, CHOC 400 cells were plated on glass coverslips in 60 mM plastic culture dishes at low density in DMEM with 1×Non-essential amino acids and 10% fetal bovine serum (FBS). After growth overnight, the medium was removed and replaced with 0.5 ml serum-free DMEM with 1×Non-essential amino acids (SFM) for 20 min. DNA with Lipofectamine and Plus reagent or protein DNA complexes with Lipofectamine were then added (200 uls per plate).

Formation of transfection complexes was achieved in two steps. For transfection by the Lipofectamine and Plus reagent method, in the first step 2 ug of each DNA was mixed into 190 ul SFM, 6 ul of Plus reagent was added, and the samples were incubated at room temperature for 20 minutes. In step 2, an equal volume of SFM containing Lipofectamine as suggested by the manufacturer was added to yield a final volume of 400 ul. For the GST-Z2 and Lipofectamine method, 2 ug of DNA was mixed with 40 ul imaging buffer and GST-Z2 was added for 20 minutes. After 20 minutes the samples were diluted with 160 ul of SFM. In step 2, an equal volume (200 ul) of SFM containing Lipofectamine as suggested by the manufacturer was added to yield a final volume of 400 ul, exactly as for the Lipofectamine with Plus reagent method outlined above. To prepare duplicate samples for each condition, the 400 ul samples were divided into two tubes.

Each sample was then added to replicate plate of cells containing SFM. In each experiment, two plates received no DNA. After 3 hrs, 1.5 ml of DMEM with 1×Non-essential amino acids and 10% FBS and antibiotics was added. Coverslips were removed after four days, washed in phosphate buffered saline (PBS) twice, and then fixed in PBS with 3% paraformaldehye. The coverslips were inverted and mounted on microscope slides with Vectasheild, and GFP expression was visualized by confocal microscopy.

As controls for GFP expression, a plasmid containing a GFP reporter gene under the control of the CMV promoter (pK7-GFP) was introduced into CHOC 400 cells by the Lipofectamine with Plus reagent method alone. The ability of GST-Z2 alone to introduce pK7-GFP into cells was also tested.

Results: To test the ability of GST-Z2 to enhance the delivery of BAC 269 DNA into cells, the number of GFP positive cells obtained by Lipofectamine and Plus reagent (Life Technologies) was compared to the number of GFP positive cells obtained by GST-Z2 and Lipofectamine 4 days post-transfection. Earlier work indicated that Lipofectamine alone supported transfer of BAC DNA into tissue culture cells at a rate of 1–10 GFP positive cells per 200,000 cells when cells were scored for GFP expression after 4 days.

Plates receiving no GFP reporter DNA display random, infrequent fluorescence that is not associated with cells. Plates receiving pK7-GFP by the Plus reagent and Lipofectamine method showed high levels of GFP expression in greater than 50% of the cells, as has been demonstrated previously by the manufacturer. Plates receiving BAC 269 by the Plus reagent and Lipofectamine method showed low levels of GFP expression in 5–15 cells per field, a result in agreement with previous observations. Plates receiving BAC 269 by the GST-Z2 and Lipofectamine method showed low to intermediate levels of GFP expression in 200–300 cells per field, an increase in transfection efficiency of at least 20-fold over the Plus reagents and Lipofectamine method under these experimental conditions. Plates receiving pK7-GFP with GST-Z2 alone showed low levels of GFP expression in 30–50 cells per field.

Using the number of GFP positive cells as a measure of the efficiency of transfer of the GFP reporter genes in the test nucleic acid molecules into CHOC 400 cells, these experiments provide several conclusions. GST-Z2 alone is able to introduce plasmid DNA into CHOC 400 cells, showing that GST-Z2/DNA complexes are able to enter into cells independently of other agents. GST-Z2 lacks any obvious cell recognition domain, so these data indicate that condensation of BAC 269 by GST-Z2 represents an important step in optimizing transfection procedures. GST-Z2 markedly potentiates the ability of Lipofectamine to introduce BAC 269 into CHOC 400 cells, indicating condensation of the BAC DNA by GST-Z2 represents an important step for improving the entry of large DNA molecules into mammalian cells in culture. The presence of the 26 kD GST purification tag at the amino terminus of the RIP60 Z2 DNA binding domain does not prevent Z2 from binding and condensing BAC 269 DNA. Thus, fusion proteins containing other protein sequences fused to the Z2 DNA binding and multimerization domains of RIP60 retain the ability to condense DNA molecules into GST-Z2/DNA complexes. Exposure of CHOC 400 cells to BAC 269/GST-Z2 complexes does not result in significant cytotoxicity. In its present configuration, the GST-Z2 in combination with Lipofectamine transfection method provides a simple and highly efficient manner by which to introduce large DNA molecules into tissue culture cells. This work therefore supports the rationale for DNA delivery by fusion proteins containing the Z2 DBD and multimerization domains of RIP60.

Example 11

The Proline-rich Region of RIP60

Table 6 shows the amino acid sequence of RIP60 between zinc finger 8 of hand Z2 and zinc finger 9 of hand Z3 (see Houchens et al., Nucleic Acids Research, in press). This sequence corresponds to the proline rich region of RIP60, which contains three proline helices (denoted helix 1, 2 and 3), one casein kinase II phosphorylation site (denoted CK II site), and a SH3-binding domain (denoted SH3 site). Of 58 amino acid residues which constitute the proline rich region, 18 are proline (bold). This region contains repeated P-X-X motifs associated with polyproline type II helices (underlined), a consensus SH3 binding domain (italic) and a consensus casein kinase II phosphorylation site, SAAE (italic). The 3' termini of GST fusion proteins (GST-Z2 P, GST-Z2-P1, GST-Z2 (also denoted GST-Z2-P1w), and GST-Z2-P123 that have been expressed in bacteria and purified for DNA binding and phosphorylation studies are at positions 6, 31, 43 and 66 respectively.

Example 12

SDS Polyacrylamide Gel Electrophoresis of GST-Z2 Fusion Proteins

GST-Z2ΔP, GST-Z2-P1, GST-Z2 (also denoted GST-Z2-P12), and GST-Z2-P123 were expressed in BL21 E. coli cells and purified as described by Houchens et al. (Nucleic Acids Research, in press). Ten micrograms of each purified protein was denatured in SDS sample buffer and subjected to electrophoresis in an 8.0% SDS polyacrylamide gel under denaturing conditions. The gel then was stained with Coomassie Blue dye and photographed. BRL prestained protein ladder as electrophoresis markers. The various GST-Z2 deletions mutants migrated to the expected size with GST-Z2ΔP being the fastest migrating species (with a size of approximately less then 38 kD, and GST-Z2-P123 being the slowest migrating species (with a size of approximately 52 kD).

Example 13

Phosphorylation of GST-Z2 by Casein Kinase II in Vitro

Materials and Methods: The indicated GST fusion protein was incubated in a 10 μl reaction containing: 5 μl protein (1 μg per μl), 1 μl CKII (casein kinase II; 500 units; New England Biolabs), 1 μl α-$^{32}$P-ATP (6000 C/mmol; NEN), 1 μl 10×CK II buffer (1×buffer=200 mM Tris-HCl, pH 7.5; 50 mM KCl, 10 mM $MgCl_2$), and 2 μl double-distilled $H_2O$. The reactions were incubated at 30° C. for 30 min and terminated by the addition of 10 μl 2×SDS sample buffer plus 100 mM DTT. After heating to 95° C. for 5 min, the reactions were resolved by electrophoresis on 8.0% SDS polyacrylamide gels. The gels were dried and protein bands labeled with $^{32}$P were visualized by exposure to Kodak X-Omat X-ray film.

Results: Only the GST-Z2 polypeptide, which contains the casein kinase II phosphorylation domain was phosphorylated. In contrast, neither GST-Z1 nor GST-Z3 were phosphorylated to any great degree. GST-Z2ΔP, the deletion mutant of GST-Z2 which sequences after zinc finger 8, was not phosphorylated by casein kinase II. Both GST-Z2 and GST-Z2P123 were phosphorylated. The deletion of sequences that include the SAAE motif of the proline-rich region from GST-Z2 to generate GST-Z2ΔP markedly reduces phosphorylation by casein kinase II in vitro.

Example 14

Phosphorylation of GST-Z2 in Vitro by Casein Kinase II is Stimulated by DNA

Materials and Methods: Five micrograms of GST-Z2 was phosphorylated as in Example except that some reactions contained non-specific carrier DNA, or a double-stranded oligonucleotide representing the downstream RIP60 binding site (dsDRS oligo), or linearized plasmid pCH127, or supercoiled pCH127. As a control a reaction was run with no DNA. The reactions were incubated and processed as described above. The DNA substrates used in these reactions are described in Houchens et al. (Nucleic Acids Research, in press).

Results. GST-Z2 polypeptide was phosphorylated by casein kinase II in the absence of DNA. However, the extent of phosphorylation increased in the presence of the double stranded DRS oligo, the linearized plasmid pCH127 and the supercoiled pCH127. Thus, it appears that GST-Z2 is optimally phosphorylated by casein kinase II when bound to DNA, since the presence of DNA to which GST-Z2 can bind stimulated phosphorylation over the level achieved in the presence of non-specific DNA or in the absence of DNA.

Example 15

RIP60 Cofractionates with a Casein Kinase Activity

Materials and Methods. RIP60 was purified from HeLa cell nuclear extract exactly as described previously (L.

TABLE 6

The Proline Rich Region

```
finger 8                    CK II site      SH3 binding site
HSKIHKRSEGSAQAAPGPGSPQLPAGPQESAAEPTPAVPLKPAQEPPPGAPPEHPQDPIE
                helix 1          helix 2            helix 3
APPSLYSCDDCG
     finger 9 (SEQ ID NO:68)
```

Dailey, et al., *Mol. Cell. Biol.* 10:6225–6235, 1990). Two micrograms of purified RIP60 protein was incubated in kinase buffer with α-$^{32}$P-ATP (6000 C/mmol; NEN) without or with casein (Sigma) as substrate. The reactions were processed and examined by SDS gel electrophoresis and autoradiography as described above. A control reaction containing no RIP60 was used as the control.

Results. In the absence of either casein or RIP60, no phosphorylated bands were observed. In the presence of RIP60 and casein, phosphorylated casein bands were resolved. This indicated that RIP60 purified from HeLa cells cofractionates with an activity which is capable of phosphorylating casein in vitro. The control lacking RIP60 did not yield phosphorylation bands, eliminating the possibility that the kinase activity derived from the casein preparation.

Example 16

Phosphorylated RIP60 Does Not Bind DNA

Materials and Methods. RIP60 purified from HeLa cell nuclear extract (see above) was phosphorylated with casein kinase II with unlabeled ATP or α-$^{32}$P-ATP. The protein preparations were then evaluated for DNA binding activity with either $^{32}$P-labeled or unlabeled dsDRS oligonucleotide probe using an electrophoretic gel mobility shift assay as described by Dailey et al. (L. Dailey, et al., *Mol. Cell. Biol.* 10:6225–6235, 1990).

Results. $^{32}$-P-labeled dsDRS probe alone migrated as free probe in the absence of RIP60. Purified RIP60 which was not phosphorylated with casein kinase II in vitro when incubated with $^{32}$-P-labeled dsDRS probe migrated as a RIP60-DNA complex. When purified RIP60, which was treated with casein kinase II and either unlabeled or labeled ATP, was incubated with $^{32}$-P-labeled or unlabeled dsDRS probe less, if any, RIP60-DNA complex was formed. This latter observation suggested that phosphorylated RIP60 was less effective at binding dsDRS DNA as compared to unphosphorylated RIP60.

These results have led to a model for the proposed role of GST-Z2 phosphorylation by casein kinase II in gene delivery. Protein-GST-Z2 complexes may be adsorbed to the cell surface, internalized, and shuttled to the nucleus. Upon nuclear entry phosphorylation of the SAAE casein kinase II site in the proline-rich region of RIP60 or its derivatives by casein kinase II (or other kinase) may disrupt the binding of RIP60 or its derivatives to DNA, thereby facilitating the release of the DNA for transcription and other steps in gene expression.

Example 17

Sequence Specificity of Z2 Domain of RIP60

Three rounds of PCR selection from an oligonucleotide library containing 16 bp of randomized sequence resulted in the identification of sequences that were preferentially bound by Z2. These sequences are enriched in ATT triplets and/or T-rich sequences. The original DSR binding site to which full length RIP60 preferentially binds is TTTTTT-TATTATTATTATTAGT (SEQ ID NO:67). GST-Z2 will bind both the DSR and related sequences. Degenerate sequences related to the DSR such as those identified in this PCR screen would be expected to occur frequently in large DNA molecules. As shown in the footprinting data above, once GST-Z2 is bound to the DSR, it will multimerize on DNA and protect unrelated sequences. The binding specificity of Z2 appears to be relaxed as compared to the full length RIP60 protein.

TABLE 7

| Sequences From Z2 Mediated PCR | |
|---|---|
| AATTTACCGTTTCTAT | (SEQ ID NO:52) |
| CCTTCCTTCTTATTCA | (SEQ ID NO:53) |
| TTCATTTGATTTTATT | (SEQ ID NO:54) |
| TTTTATAATTCCTATT | (SEQ ID NO:55) |
| TCTAATTTTCTTTTTA | (SEQ ID NO:56) |
| TGTTTTGATTTTTAT | (SEQ ID NO:57) |
| TATTTTATTTATTAAT | (SEQ ID NO:58) |
| TTCTTTTTTCATAAAT | (SEQ ID NO:59) |
| TATTATTTTATGTTGA | (SEQ ID NO:60) |
| TTTTTAAATTTTTTA | (SEQ ID NO:61) |
| GATGAATTTTTTTTA | (SEQ ID NO:62) |
| TACTTTATGGTTAAGC | (SEQ ID NO:63) |
| CTATTACTGTTTTCTG | (SEQ ID NO:64) |
| TTTTTTTAGTTTCTTA | (SEQ ID NO:65) |
| TACTTTATGGTTAACG | (SEQ ID NO:66) |

Equivalents

Those skilled in the art will recognize, or be able to ascertain using no more than routine experimentation, many equivalents to the specific embodiments of the invention described herein. Such equivalents are intended to be encompassed by the following claims.

All references, patents, and patent applications disclosed herein are incorporated by reference in their entirety.

What is claimed is presented below and is followed by a sequence listing:

---

I claim:

1. A non-viral nucleic acid delivery complex comprising a modular polypeptide comprising a nucleic acid binding domain that binds a nucleic acid molecule of more than 50 kilobases in length and is selected from the group consisting of Z1 (amino acids 1–231 of SEQ ID NO:2), Z2 (amino acids 225–349 of SEQ ID NO:2), Z2ΔP (amino acids 225–313 of SEQ ID NO:2), Z3 (amino acids 343–567 of SEQ ID NO:2), SEQ ID NO:4, SEQ ID NO:49, SEQ ID NO:51, and zinc finger domains that are coded by nucleic acid molecules that hybridize under stringent conditions to complements of nucleic acid molecules having a nucleotide sequence selected from the group consisting of nucleotides 1–702 of SEQ ID NO:1, nucleotides 682–1058 of SEQ ID NO:1, nucleotides 682–948 of SEQ ID NO:1, and nucleotides 1039–1704 of SEQ ID NO:1, SEQ ID NO:3, SEQ ID NO:48, and SEQ ID NO:50; and a nucleic acid condensation domain that condenses a nucleic acid molecule of more than 50 kilobases in length and is a proline rich region of RIP60 selected from the group consisting of SEQ ID NO:4, SEQ ID NO:6, SEQ ID NO:51, SEQ ID NO:68, amino acids 316–374 of SEQ ID NO:2, and domains that are coded by nucleic acid molecules that hybridize under stringent conditions to complements of nucleic acid molecules having a nucleotide sequence selected from the group consisting of SEQ ID NO:3, SEQ ID NO:5, SEQ ID NO:50, and nucleotides 682–948 of SEQ ID NO:1; and one or more polypeptides selected from the group consisting of a cell recognition domain, a protein transduction domain, a protein degradation domain, an intracellular targeting domain, a protein interaction domain, an epitope domain, and a protein purification domain, wherein the stringent conditions are hybridization at 65° C. in hybridization buffer (3.5×SSC, 0.02% Ficoll, 0.02% polyvinyl pyrolidone, 0.02% Bovine Serum Albumin, 2.5 mM NaH$_2$PO$_4$(pH7), 0.5% SDS, 2 mM EDTA); wherein SSC is 0.15M sodium chloride/ 0.015M sodium citrate, pH7; SDS is sodium dodecyl sulphate; and EDTA is ethylenediaminetetracetic acid.

2. The nucleic acid delivery complex of claim 1, wherein the modular polypeptide contains two or more polypeptides selected from the group consisting of a cell recognition domain, a protein transduction domain, a protein degradation domain, an intracellular targeting domain, a protein interaction domain, an epitope domain, and a protein purification domain.

3. The nucleic acid delivery complex of claim 1, wherein the modular polypeptide is complexed with a nucleic acid.

4. The nucleic acid delivery complex of claim 1, wherein the modular polypeptide delivers to a cell a nucleic acid equal to or more than 100 kilobases in length.

5. The nucleic acid delivery complex of claim 1, wherein the nucleic acid binding domain recognizes and binds a nucleic acid in a sequence independent manner.

6. The nucleic acid delivery complex of claim 1, wherein the nucleic acid binding domain interacts with an ATT-rich sequence of the nucleic acid.

7. The nucleic acid delivery complex of claim 3, wherein the nucleic acid is an antisense nucleic acid molecule.

8. The nucleic acid delivery complex of claim 3, wherein the nucleic acid is a DNA molecule.

9. The nucleic acid delivery complex of claim 3, wherein the nucleic acid is an RNA molecule.

10. The nucleic acid delivery complex of claim 3, wherein the nucleic acid is a DNA/RNA hybrid molecule.

11. The nucleic acid delivery complex of claim 3, wherein the nucleic acid is an unmodified fragment of chromosomal DNA.

12. The nucleic acid delivery complex of claim 3, wherein the nucleic acid is a BAC.

13. The nucleic acid delivery complex of claim 3, wherein the nucleic acid is a YAC.

14. The nucleic acid delivery complex of claim 3, wherein the nucleic acid is single stranded.

15. The nucleic acid delivery complex of claim 3, wherein the nucleic acid is double stranded.

16. The nucleic acid delivery complex of claim 1, wherein the nucleic acid binding domain and the nucleic acid condensation domain are a Z2 domain of a zinc finger protein RIP60 selected from the group consisting of Z2 (amino acids 225–349 of SEQ ID NO:2), Z2ΔP (amino acids 225–313 of SEQ ID NO:2), SEQ ID NO:4, SEQ ID NO:50, and zinc finger domains that are coded by nucleic acid molecules that hybridize under stringent conditions to complements of nucleic acid molecules having a nucleotide sequence selected from the group consisting of nucleotides 682–1058 of SEQ ID NO:1, nucleotides 682–948 of SEQ ID NO:1, SEQ ID NO:3 and SEQ ID NO:51.

17. The nucleic acid delivery complex of claim 1, wherein the nucleic acid binding domain is a Z2 domain of a zinc finger protein RIP60 selected from the group consisting of Z2 (amino acids 225–349 of SEQ ID NO:2), Z2ΔP (amino acids 225–313 of SEQ ID NO:2), SEQ ID NO:4, SEQ ID NO:50, and zinc finger domains that are coded by nucleic acid molecules that hybridize under stringent conditions to complements of nucleic acid molecules having a nucleotide sequence selected from the group consisting of nucleotides 682–1058 of SEQ ID NO:1, nucleotides 682–948 of SEQ ID NO:1, SEQ ID NO:3 and SEQ ID NO:51.

18. The nucleic acid delivery complex of claim 1, wherein the nucleic acid condensation domain comprises an amino acid sequence selected from the group consisting of SEQ ID NO:6, SEQ ID NO:51, and SEQ ID NO:68.

19. The nucleic acid delivery complex of claim 1, wherein the proline rich region of RIP60 comprises an amino acid sequence of SEQ ID NO:6, amino acids 12–23 of SEQ ID NO:6, amino acids 28–38 of SEQ ID NO:6, amino acids 46–54 of SEQ ID NO:6, and amino acids 10–57 of SEQ ID NO:6.

20. The nucleic acid delivery complex of claim 1, wherein the nucleic acid condensation domain comprises a phosphorylation site.

21. The nucleic acid delivery complex of claim 1, wherein the cell recognition domain binds to a cell surface receptor.

22. The nucleic acid delivery complex of claim 1, wherein the cell recognition domain binds to an extracellular matrix molecule.

23. The nucleic acid delivery complex of claim 1, wherein the cell recognition domain binds to a carbohydrate moiety.

24. The nucleic acid delivery complex of claim 1, wherein the cell recognition domain is an antibody or an antibody fragment.

25. The nucleic acid delivery complex of claim 1, wherein the protein degradation domain is a PEST sequence.

26. The nucleic acid delivery complex of claim 1, wherein the intracellular targeting domain is a nuclear localization signal sequence.

27. The nucleic acid delivery complex of claim 1, wherein the intracellular targeting domain causes the release of the nucleic acid delivery complex from an endosome.

28. The nucleic acid delivery complex of claim 1, wherein the protein interaction domain associates with a polypeptide selected from the group consisting of a signal transduction molecule, a carbohydrate expressing polypeptide, a hormone, a hormone receptor, and a transcription factor.

29. The nucleic acid delivery complex of claim 1, wherein the protein interaction domain is a proline rich domain that comprises at least 30% prolines.

30. The nucleic acid delivery complex of claim 1, wherein the epitope domain is selected from the group consisting of a hemaglutinnin tag, a FLAG tag, a V5 tag, a myc tag, and a T7 tag.

31. The nucleic acid delivery complex of claim 1, wherein the protein purification domain is selected from a group consisting of a GST sequence tag, a hexahistidine tag, a polyhistidine tag, a Protein A tag, a biotin tag, a chitin tag, and a maltose binding protein.

32. A non-viral nucleic acid delivery complex comprising
a modular polypeptide comprising
a nucleic acid binding domain that binds a nucleic acid molecule of more than 50 kilobases in length and that is selected from the group consisting of a zinc finger domain, a basic helix-loop-helix domain, a homeodomain, and an nucleic acid specific antibody or fragment thereof; and
a nucleic acid condensation domain that condenses a nucleic acid molecule of more than 50 kilobases in length and is selected from the group consisting of SEQ ID NO:4, SEQ ID NO:6, SEQ ID NO:51, SEQ ID NO:68, amino acids 316–374 of SEQ ID NO:2, and domains that are coded by nucleic acid molecules that hybridize under stringent conditions to complements of nucleic acid molecules having a nucleotide sequence selected from the group consisting of SEQ ID NO:3, SEQ ID NO:5, SEQ ID NO:50, and nucleotides 682–948 of SEQ ID NO:1; and
one or more polypeptides selected from the group consisting of a cell recognition domain, a protein transduction domain, a protein degradation domain, an intracellular targeting domain, a protein interaction domain, an epitope domain, and a protein purification domain,
wherein the stringent conditions are hybridization at 65° C. in hybridization buffer (3.5×SSC, 0.02% Ficoll, 0.02% polyvinyl pyrolidone, 0.02% Bovine Serum Albumin, 2.5 mM NaH$_2$PO$_4$(pH7), 0.5% SDS, 2 mM EDTA); wherein SSC is 0.15M sodium chloride/ 0.015M sodium citrate, pH7; SDS is sodium dodecyl sulphate; and EDTA is ethylenediaminetetracetic acid.

33. A composition comprising:
an agent comprising the nucleic acid delivery complex of claim 1 or 32, and
a pharmaceutically acceptable carrier.

34. A kit comprising
the composition of claim 33, and
a package.

35. A method of delivering to a cell a non-viral nucleic acid encoding one or more polypeptides comprising
delivering to a cell a non-viral nucleic acid in the nucleic acid delivery complex of claim 1 or 32, wherein the nucleic acid comprises two or more native regulatory and structural nucleic acid elements for at least one of the encoded polypeptides selected from the group consisting of locus control regions, 5' and 3' flanking sequences, introns, promoters, enhancers, and coding sequences,
in an amount effective to deliver the nucleic acid to the cell.

36. The method of claim 35, wherein the nucleic acid contains three or more native regulatory and structural nucleic acid elements.

37. The method of claim 35, wherein the nucleic acid is delivered to the cell in vitro.

38. A method for delivering a nucleic acid into a cell comprising
delivering to a cell the non-viral nucleic acid delivery complex of claim 1 or 32, wherein the modular polypeptide is complexed with a nucleic acid of more than 50 kilobases in length,
in an amount effective to delivery the nucleic acid into the cell.

39. The method of claim 38, wherein the non-viral nucleic acid delivery complex is the non-viral nucleic acid delivery complex of claim 1.

40. The method of claim 38, wherein the cell is a eukaryotic cell.

41. The method of claim 38, wherein the cell is a prokaryotic cell.

42. The method of claim 38, wherein the cell is in a suspension, a tissue or fragment thereof, or an organ or fragment thereof, in vitro or in vivo.

43. The method of claim 38, wherein the cell is derived from a subject with one or more genetic mutations.

44. The method of claim 38, wherein the nucleic acid is delivered to the cell by passive or active transport.

45. The non-viral nucleic acid delivery complex of claim 32, wherein the nucleic acid condensation domain comprises an amino acid sequence selected from the group consisting of SEQ ID NO:4, SEQ ID NO:6, SEQ ID NO:51, SEQ ID NO:68, and amino acids 316–374 of SEQ ID NO:2.

46. The non-viral nucleic acid delivery complex of claim 32, wherein the nucleic acid binding domain is a nucleic acid specific antibody or a fragment thereof.

47. The non-viral nucleic acid delivery complex of claim 32, wherein the nucleic acid condensation domain comprises the amino acid sequence of SEQ ID NO:6.

48. The nucleic acid delivery complex of claim 1, wherein the modular polypeptide contains three or more polypeptides selected from the group consisting of a cell recognition domain, a protein transduction domain, a protein degradation domain, an intracellular targeting domain, a protein interaction domain, an epitope domain, and a protein purification domain.

49. The nucleic acid delivery complex of claim 1, wherein the modular polypeptide contains four or more polypeptides selected from the group consisting of a cell recognition domain, a protein transduction domain, a protein degradation domain, an intracellular targeting domain, a protein interaction domain, an epitope domain, and a protein purification domain.

50. The nucleic acid delivery complex of claim 1, wherein the modular polypeptide contains five or more polypeptides selected from the group consisting of a cell recognition domain, a protein transduction domain, a protein degradation domain, an intracellular targeting domain, a protein interaction domain, an epitope domain, and a protein purification domain.

51. The nucleic acid delivery complex of claim 1, wherein the modular polypeptide contains six or more polypeptides selected from the group consisting of a cell recognition domain, a protein transduction domain, a protein degradation domain, an intracellular targeting domain, a protein interaction domain, an epitope domain, and a protein purification domain.

52. The nucleic acid delivery complex of claim 1, wherein the modular polypeptide contains seven polypeptides selected from the group consisting of a cell recognition domain, a protein transduction domain, a protein degradation domain, an intracellular targeting domain, a protein interaction domain, an epitope domain, and a protein purification domain.

53. The nucleic acid delivery complex of claim 1, wherein the modular polypeptide delivers to a cell a nucleic acid equal to or more than 200 kilobases in length.

54. The nucleic acid delivery complex of claim 1, wherein the epitope domain is a hemaglutinnin tag.

55. The nucleic acid delivery complex of claim 1, wherein the epitope domain is a FLAG tag.

56. The nucleic acid delivery complex of claim 1, wherein the protein purification domain is a GST sequence tag.

57. The nucleic acid delivery complex of claim 1, wherein the protein purification domain is a hexahistidine tag.

58. The method of claim 35, wherein the nucleic acid contains four or more native regulatory and structural nucleic acid elements.

59. The method of claim 35, wherein the nucleic acid contains five or more native regulatory and structural nucleic acid elements.

60. The method of claim 35, wherein the nucleic acid contains six native regulatory and structural nucleic acid elements.

61. The method of claim 35, wherein the nucleic acid is equal to or more than 50 kilobases in length.

62. The method of claim 38, wherein the nucleic acid is the nucleic acid of claims 13–21.

63. The method of claim 38, wherein the cell is an animal cell.

64. The method of claim 38, wherein the cell is a human cell.

65. The method of claim 38, wherein the cell is an insect cell.

66. The method of claim 38, wherein the cell is a plant cell.

67. The method of claim 38, wherein the cell is a mouse cell.

68. The method of claim 38, wherein the cell is a Drosophila cell.

* * * * *

UNITED STATES PATENT AND TRADEMARK OFFICE
CERTIFICATE OF CORRECTION

PATENT NO. : 6,903,077 B1
DATED : June 7, 2005
INVENTOR(S) : Heintz

It is certified that error appears in the above-identified patent and that said Letters Patent is hereby corrected as shown below:

Column 97,
Line 36, "delivery" should read -- deliver --.

Signed and Sealed this

Second Day of August, 2005

JON W. DUDAS
*Director of the United States Patent and Trademark Office*